US010539502B2

(12) United States Patent
Ruback et al.

(10) Patent No.: US 10,539,502 B2
(45) Date of Patent: Jan. 21, 2020

(54) MOISTURE MEASUREMENT DEVICE WITH THERMAL IMAGING CAPABILITIES AND RELATED METHODS

(71) Applicant: FLIR Systems, Inc., Wilsonville, OR (US)

(72) Inventors: Samuel Ruback, Bedford, NH (US); James Miglietta, Malden, MA (US); Michael Fox, Stillwater, OK (US)

(73) Assignee: FLIR SYSTEMS, INC., Wilsonville, OR (US)

( * ) Notice: Subject to any disclaimer, the term of this patent is extended or adjusted under 35 U.S.C. 154(b) by 61 days.

(21) Appl. No.: 15/795,002

(22) Filed: Oct. 26, 2017

(65) Prior Publication Data

US 2018/0059014 A1 Mar. 1, 2018

Related U.S. Application Data

(63) Continuation of application No. PCT/US2016/029628, filed on Apr. 27, 2016.
(Continued)

(51) Int. Cl.
*H04N 5/33* (2006.01)
*G01N 21/3554* (2014.01)
(Continued)

(52) U.S. Cl.
CPC ..... *G01N 21/3554* (2013.01); *G01N 21/3563* (2013.01); *H04N 5/23229* (2013.01); *H04N 5/23293* (2013.01); *H04N 5/33* (2013.01)

(58) Field of Classification Search
CPC ........... G01N 21/3554; G01N 21/3563; H04N 5/23229; H04N 5/23293
(Continued)

(56) References Cited

U.S. PATENT DOCUMENTS 4,661,986 A 4/1987 Adelson
4,975,864 A 12/1990 Sendall et al.
(Continued)

FOREIGN PATENT DOCUMENTS

CN 103875235 6/2014
CN 104254869 12/2014
(Continued)

OTHER PUBLICATIONS

Eminoglu, Selim, "Uncooled Infrared Focal Plane Arrays with Integrated Readout Circuitry Using MEMS and Standard CMOS Technologies," Jul. 2003, 305 Pages, The Middle East Technical University.
(Continued)

*Primary Examiner* — Nguyen T Truong
(74) *Attorney, Agent, or Firm* — Haynes and Boone, LLP

(57) ABSTRACT

Techniques are disclosed for measurement devices and methods to obtain physical parameters and thermal images associated with a scene in an integrated manner. In one embodiment, a measurement device includes an infrared (IR) imaging module configured to capture thermal images of a scene; a moisture sensor configured to detect a moisture parameter associated with an external article; a housing configured to be hand-held by a user and at least partially enclosing the IR imaging module; a display fixed relative to the housing and configured to display user-viewable thermal images; and a logic device configured to freeze a user-viewable thermal image on the display, overlay information to indicate a first detection of the moisture parameter onto the frozen user-viewable thermal image on the display, and update the overlaid information to indicate a second detection of the moisture parameter.

20 Claims, 24 Drawing Sheets

Related U.S. Application Data

(60) Provisional application No. 62/153,502, filed on Apr. 27, 2015.

(51) Int. Cl.
*H04N 5/232* (2006.01)
*G01N 21/3563* (2014.01)

(58) Field of Classification Search
USPC .................................................. 348/164
See application file for complete search history.

(56) References Cited

U.S. PATENT DOCUMENTS

| | | | |
|---|---|---|---|
| 5,140,416 A | 8/1992 | Tinkler | |
| 5,488,674 A | 1/1996 | Burt et al. | |
| 5,555,324 A | 9/1996 | Waxman et al. | |
| 5,994,699 A | 11/1999 | Akagawa | |
| 6,028,309 A | 2/2000 | Parrish et al. | |
| 6,812,465 B2 | 11/2004 | Parrish et al. | |
| 7,034,301 B2 | 4/2006 | Parrish et al. | |
| 7,237,946 B2 | 7/2007 | Lindstrom et al. | |
| 7,470,902 B1 | 12/2008 | Kraemer et al. | |
| 7,470,904 B1 | 12/2008 | Schweikert et al. | |
| 7,620,265 B1 | 11/2009 | Wolff et al. | |
| 7,679,048 B1 | 3/2010 | Aziz et al. | |
| 7,734,171 B2 | 6/2010 | Leonelli, Jr. | |
| 7,876,973 B2 | 1/2011 | Fairbanks et al. | |
| 8,049,163 B1 | 11/2011 | Granneman et al. | |
| 8,080,794 B1 | 12/2011 | Woolaway et al. | |
| 8,208,026 B2 | 6/2012 | Hogasten et al. | |
| 8,378,290 B1 | 2/2013 | Speake et al. | |
| 8,565,547 B2 | 10/2013 | Strandemar | |
| 8,727,608 B2 | 5/2014 | Blakeley, III | |
| 8,743,207 B2 | 6/2014 | Boulanger et al. | |
| 9,171,361 B2 | 10/2015 | Strandemar | |
| 9,208,542 B2 | 12/2015 | Högasten et al. | |
| 9,706,139 B2 | 7/2017 | Nussmeier et al. | |
| 9,716,843 B2 | 7/2017 | Fox et al. | |
| 9,723,228 B2 | 8/2017 | Boulanger et al. | |
| 9,900,478 B2 | 2/2018 | Fox et al. | |
| 2001/0042825 A1 | 11/2001 | Young | |
| 2002/0015536 A1 | 2/2002 | Warren et al. | |
| 2002/0058352 A1 | 5/2002 | Jacksen et al. | |
| 2003/0198400 A1 | 10/2003 | Alderson et al. | |
| 2004/0128613 A1 | 7/2004 | Sinisi | |
| 2005/0248684 A1 | 11/2005 | Machida | |
| 2006/0017821 A1 | 1/2006 | Garvey, III et al. | |
| 2006/0043296 A1 | 3/2006 | Mian et al. | |
| 2006/0132642 A1 | 6/2006 | Hosaka et al. | |
| 2006/0289772 A1 | 12/2006 | Johnson et al. | |
| 2006/0290796 A1 | 12/2006 | Nikkanen et al. | |
| 2007/0177819 A1 | 8/2007 | Ma et al. | |
| 2007/0185379 A1 | 8/2007 | Newman et al. | |
| 2008/0056606 A1 | 3/2008 | Kilgore | |
| 2008/0252775 A1 | 10/2008 | Ryu et al. | |
| 2008/0259993 A1 | 10/2008 | Blakeley | |
| 2009/0273675 A1 | 11/2009 | Jonsson | |
| 2009/0303363 A1 | 12/2009 | Blessinger | |
| 2010/0046577 A1 | 2/2010 | Sheard et al. | |
| 2010/0283890 A1 | 11/2010 | Mizumura | |
| 2010/0309315 A1 | 12/2010 | Hogasten et al. | |
| 2010/0329583 A1 | 12/2010 | Whiteside et al. | |
| 2011/0169481 A1 | 7/2011 | Nguyen et al. | |
| 2011/0221599 A1 | 9/2011 | Högasten | |
| 2012/0245878 A1 | 9/2012 | Kane et al. | |
| 2014/0104415 A1 | 4/2014 | Fox et al. | |

FOREIGN PATENT DOCUMENTS

| | | |
|---|---|---|
| CN | 204087290 | 1/2015 |
| EP | 1732314 | 12/2006 |
| EP | 2634747 | 9/2013 |
| WO | WO 2012/115881 | 8/2012 |
| WO | WO 2014/105241 | 7/2014 |
| WO | WO 2014/105993 | 7/2014 |
| WO | WO 2015/123143 | 8/2015 |

OTHER PUBLICATIONS

Gangkofner et al., "Optimizing the High-Pass Filter Addition Technique for Image Fusion," Photogrammetric Engineering & Remote Sensing, Sep. 1, 2008, pp. 1107-1118, vol. 74, No. 9.

"FLIR TG165 Imaging IR Thermometer," FLIR®, Sep. 2, 2014, 32 Pages [online], XP055296603, [retrieved on Aug. 19, 2016], Retrieved from the Internet: <https://www.instrumart.com/assets/tg165-manual.pdf>.

MOISTURE MEASUREMENT DEVICE WITH THERMAL IMAGING CAPABILITIES AND RELATED METHODS

CROSS-REFERENCE TO RELATED APPLICATIONS

This application is a continuation of International Patent Application No. PCT/US2016/029628 filed Apr. 27, 2016 and entitled "MOISTURE MEASUREMENT DEVICE WITH THERMAL IMAGING CAPABILITIES AND RELATED METHODS," which is incorporated herein by reference in its entirety.

International Patent Application No. PCT/US2016/029628 filed Apr. 27, 2016 claims priority to and the benefit of U.S. Provisional Patent Application No. 62/153,502 filed Apr. 27, 2015 and entitled "MOISTURE MEASUREMENT DEVICE WITH THERMAL IMAGING CAPABILITIES AND RELATED METHODS," which is hereby incorporated by reference in its entirety.

This application is related to U.S. patent application Ser. No. 14/034,493 filed Sep. 23, 2013 and entitled "MEASUREMENT DEVICE FOR ELECTRICAL INSTALLATIONS AND RELATED METHODS" which is hereby incorporated by reference in its entirety.

U.S. patent application Ser. No. 14/034,493 is a continuation-in-part of International Patent Application No. PCT/US2013/059831 filed Sep. 13, 2013 and entitled "MEASUREMENT DEVICE FOR ELECTRICAL INSTALLATIONS AND RELATED METHODS" which is hereby incorporated by reference in its entirety.

International Patent Application No. PCT/US2013/059831 claims the benefit of U.S. Provisional Patent Application No. 61/701,292 filed Sep. 14, 2012 and entitled "MEASUREMENT DEVICE FOR ELECTRICAL INSTALLATIONS AND RELATED METHODS" which is hereby incorporated by reference in its entirety.

This application is related to U.S. patent application Ser. No. 14/922,076 filed Oct. 23, 2015 and entitled "INFRARED RESOLUTION AND CONTRAST ENHANCEMENT WITH FUSION" which is hereby incorporated by reference in its entirety.

U.S. patent application Ser. No. 14/922,076 is a continuation of U.S. patent application Ser. No. 13/437,645 filed Apr. 2, 2012 and entitled "INFRARED RESOLUTION AND CONTRAST ENHANCEMENT WITH FUSION" which is hereby incorporated by reference in its entirety.

U.S. patent application Ser. No. 13/437,645 is a continuation-in-part of U.S. patent application Ser. No. 13/105,765 filed May 11, 2011 and entitled "INFRARED RESOLUTION AND CONTRAST ENHANCEMENT WITH FUSION" which is hereby incorporated by reference in its entirety.

U.S. patent application Ser. No. 13/437,645 also claims the benefit of U.S. Provisional Patent Application No. 61/473,207 filed Apr. 8, 2011 and entitled "INFRARED RESOLUTION AND CONTRAST ENHANCEMENT WITH FUSION" which is hereby incorporated by reference in its entirety.

U.S. patent application Ser. No. 13/437,645 is also a continuation-in-part of U.S. patent application Ser. No. 12/766,739 filed Apr. 23, 2010 and entitled "INFRARED RESOLUTION AND CONTRAST ENHANCEMENT WITH FUSION" which is hereby incorporated by reference in its entirety.

U.S. patent application Ser. No. 13/105,765 is a continuation of International Patent Application No. PCT/EP2011/056432 filed Apr. 21, 2011 and entitled "INFRARED RESOLUTION AND CONTRAST ENHANCEMENT WITH FUSION" which is hereby incorporated by reference in its entirety.

This application is related to U.S. patent application Ser. No. 14/101,245 filed Dec. 9, 2013 entitled "LOW POWER AND SMALL FORM FACTOR INFRARED IMAGING" which is hereby incorporated by reference in its entirety.

U.S. patent application Ser. No. 14/101,245 is a continuation of International Patent Application No. PCT/US2012/041744 filed Jun. 8, 2012 and entitled "LOW POWER AND SMALL FORM FACTOR INFRARED IMAGING" which is hereby incorporated by reference in its entirety.

International Patent Application No. PCT/US2012/041744 claims the benefit of U.S. Provisional Patent Application No. 61/656,889 filed Jun. 7, 2012 and entitled "LOW POWER AND SMALL FORM FACTOR INFRARED IMAGING" which is hereby incorporated by reference in its entirety.

International Patent Application No. PCT/US2012/041744 claims the benefit of U.S. Provisional Patent Application No. 61/545,056 filed Oct. 7, 2011 and entitled "NON-UNIFORMITY CORRECTION TECHNIQUES FOR INFRARED IMAGING DEVICES" which is hereby incorporated by reference in its entirety.

International Patent Application No. PCT/US2012/041744 claims the benefit of U.S. Provisional Patent Application No. 61/495,873 filed Jun. 10, 2011 and entitled "INFRARED CAMERA PACKAGING SYSTEMS AND METHODS" which is hereby incorporated by reference in its entirety.

International Patent Application No. PCT/US2012/041744 claims the benefit of U.S. Provisional Patent Application No. 61/495,879 filed Jun. 10, 2011 and entitled "INFRARED CAMERA SYSTEM ARCHITECTURES" which is hereby incorporated by reference in its entirety.

International Patent Application No. PCT/US2012/041744 claims the benefit of U.S. Provisional Patent Application No. 61/495,888 filed Jun. 10, 2011 and entitled "INFRARED CAMERA CALIBRATION TECHNIQUES" which is hereby incorporated by reference in its entirety.

This application is related to U.S. patent application Ser. No. 14/099,818 filed Dec. 6, 2013 entitled "NON-UNIFORMITY CORRECTION TECHNIQUES FOR INFRARED IMAGING DEVICES" which is hereby incorporated by reference in its entirety.

U.S. patent application Ser. No. 14/099,818 is a continuation of International Patent Application No. PCT/US2012/041749 filed Jun. 8, 2012 and entitled "NON-UNIFORMITY CORRECTION TECHNIQUES FOR INFRARED IMAGING DEVICES" which is hereby incorporated by reference in its entirety.

International Patent Application No. PCT/US2012/041749 claims the benefit of U.S. Provisional Patent Application No. 61/545,056 filed Oct. 7, 2011 and entitled "NON-UNIFORMITY CORRECTION TECHNIQUES FOR INFRARED IMAGING DEVICES" which is hereby incorporated by reference in its entirety.

International Patent Application No. PCT/US2012/041749 claims the benefit of U.S. Provisional Patent Application No. 61/495,873 filed Jun. 10, 2011 and entitled "INFRARED CAMERA PACKAGING SYSTEMS AND METHODS" which is hereby incorporated by reference in its entirety.

International Patent Application No. PCT/US2012/041749 claims the benefit of U.S. Provisional Patent Application No. 61/495,879 filed Jun. 10, 2011 and entitled "INFRARED CAMERA SYSTEM ARCHITECTURES" which is hereby incorporated by reference in its entirety.

International Patent Application No. PCT/US2012/041749 claims the benefit of U.S. Provisional Patent Application No. 61/495,888 filed Jun. 10, 2011 and entitled "INFRARED CAMERA CALIBRATION TECHNIQUES" which is hereby incorporated by reference in its entirety.

This application is related to U.S. patent application Ser. No. 14/101,258 filed Dec. 9, 2013 entitled "INFRARED CAMERA SYSTEM ARCHITECTURES" which is hereby incorporated by reference in its entirety.

U.S. patent application Ser. No. 14/101,258 is a continuation of International Patent Application No. PCT/US2012/041739 filed Jun. 8, 2012 and entitled "INFRARED CAMERA SYSTEM ARCHITECTURES" which is hereby incorporated by reference in its entirety. International Patent Application No. PCT/US2012/041739 claims the benefit of U.S. Provisional Patent Application No. 61/495,873 filed Jun. 10, 2011 and entitled "INFRARED CAMERA PACKAGING SYSTEMS AND METHODS" which is hereby incorporated by reference in its entirety.

International Patent Application No. PCT/US2012/041739 claims the benefit of U.S. Provisional Patent Application No. 61/495,879 filed Jun. 10, 2011 and entitled "INFRARED CAMERA SYSTEM ARCHITECTURES" which is hereby incorporated by reference in its entirety.

International Patent Application No. PCT/US2012/041739 claims the benefit of U.S. Provisional Patent Application No. 61/495,888 filed Jun. 10, 2011 and entitled "INFRARED CAMERA CALIBRATION TECHNIQUES" which is hereby incorporated by reference in its entirety.

TECHNICAL FIELD

One or more embodiments of the invention relate generally to measuring instruments and more particularly, for example, to instruments providing physical and/or moisture parameter measurements.

BACKGROUND

Building inspection, repair, or maintenance work often requires building inspectors, contactors, homeowners, or other users to perform a series of inspections and measurements to find, classify, and quantify building issues such as moisture-related damage or missing insulation. Infrared cameras are becoming more and more popular as an inspection tool that can be used to scan inspection sites to locate thermal anomalies which may indicate various building issues. To classify whether the generally located thermal anomalies are moisture-related or other issues such as missing insulation and to quantify the classified issues, users typically have to perform a series of measurement using separate measurement devices such as a moisture meter.

However, performing a series of inspections and measurements with a separate infrared camera and measurement devices is not only inconvenient for users who have to carry around and switch among multiple separate devices, but also makes it difficult to obtain quick and accurate measurements because of the difficulty of associating the general location of thermal anomalies captured by an infrared camera with specific locations from which the subsequent measurements should be taken. Moreover, the thermal anomalies captured by an infrared camera and the subsequent measurements taken by a separate measurement device cannot be associated, viewed, documented, and stored together for future reference and analysis.

SUMMARY

Various techniques are disclosed for measurement devices and methods to obtain physical and/or moisture parameters and thermal images associated with a scene in an integrated manner.

In one or more embodiments, a measurement device includes an infrared (IR) imaging module configured to capture thermal images of a scene; a moisture sensor configured to detect a moisture parameter associated with an external article; a housing configured to be hand-held by a user and at least partially enclosing the IR imaging module; a display fixed relative to the housing and configured to display user-viewable thermal images; and a logic device configured to freeze a user-viewable thermal image on the display, overlay information to indicate a first detection of the moisture parameter onto the frozen user-viewable thermal image on the display, and update the overlaid information to indicate a second detection of the moisture parameter.

In one or more embodiments, a method includes capturing a thermal image of a scene, generating a user-viewable thermal image based on the thermal image, displaying the user-viewable thermal image freezing the user-viewable thermal image, determining a first measurement of a moisture parameter associated with an external article, overlaying information to indicate the first measurement of the moisture parameter onto the frozen user-viewable thermal image, determining a second measurement of the moisture parameter associated with the external article, and updating the overlaid information to indicate the second measurement of the moisture parameter.

In some embodiments, the apparatus further includes a memory, and the logic device is further configured to capture a displayed image comprising the frozen user-viewable thermal image on the display and the overlaid information and store the captured image in the memory.

In some embodiments, the apparatus further includes a laser pointer configured to emit a beam line, and the logic device is further configured to overlay a crosshair image aligned with the beam line onto the user-viewable thermal image on the display.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the invention and their advantages are best understood by referring to the detailed description that follows. It should be appreciated that like reference numerals are used to identify like elements illustrated in one or more of the figures.

DETAILED DESCRIPTION

Figure 1:
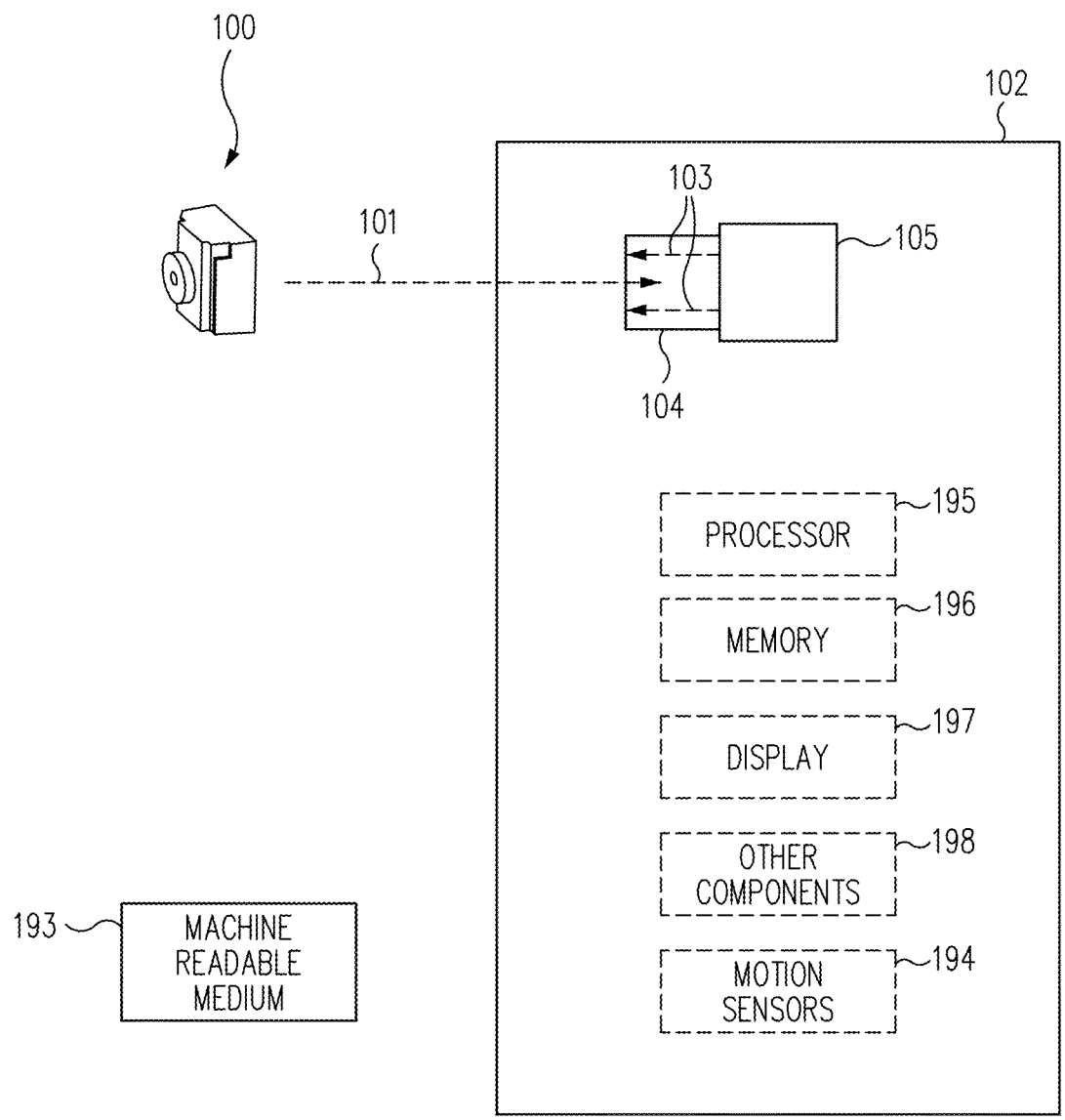
FIG. 1 illustrates an infrared imaging module configured to be implemented in a host device in accordance with an embodiment of the disclosure.

FIG. 1 illustrates an infrared imaging module 100 (e.g., an infrared camera or an infrared imaging device) configured to be implemented in a host device 102 in accordance with an embodiment of the disclosure. Infrared imaging module 100 may be implemented, for one or more embodiments, with a small form factor and in accordance with wafer level packaging techniques or other packaging techniques.

In one embodiment, infrared imaging module 100 may be configured to be implemented in a small portable host device 102, such as a mobile telephone, a tablet computing device, a laptop computing device, a personal digital assistant, a visible light camera, a music player, or any other appropriate mobile device. In this regard, infrared imaging module 100 may be used to provide infrared imaging features to host device 102. For example, infrared imaging module 100 may be configured to capture, process, and/or otherwise manage infrared images and provide such infrared images to host device 102 for use in any desired fashion (e.g., for further processing, to store in memory, to display, to use by various applications running on host device 102, to export to other devices, or other uses).

In various embodiments, infrared imaging module 100 may be configured to operate at low voltage levels and over a wide temperature range. For example, in one embodiment, infrared imaging module 100 may operate using a power supply of approximately 2.4 volts, 2.5 volts, 2.8 volts, or lower voltages, and operate over a temperature range of approximately −20 degrees C. to approximately +60 degrees C. (e.g., providing a suitable dynamic range and performance over an environmental temperature range of approximately 80 degrees C.). In one embodiment, by operating infrared imaging module 100 at low voltage levels, infrared imaging module 100 may experience reduced amounts of self heating in comparison with other types of infrared imaging devices. As a result, infrared imaging module 100 may be operated with reduced measures to compensate for such self heating.

Figure 2:
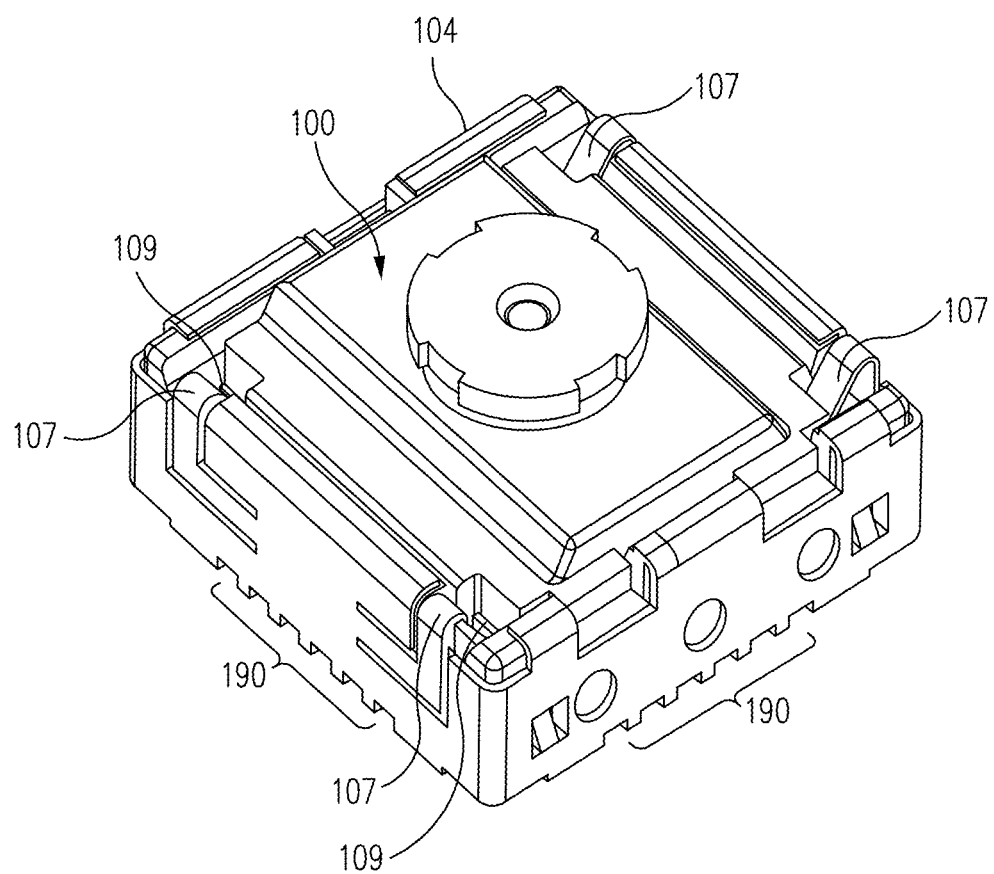
FIG. 2 illustrates an assembled infrared imaging module in accordance with an embodiment of the disclosure.

As shown in FIG. 1, host device 102 may include a socket 104, a shutter 105, motion sensors 194, a processor 195, a memory 196, a display 197, and/or other components 198. Socket 104 may be configured to receive infrared imaging module 100 as identified by arrow 101. In this regard, FIG. 2 illustrates infrared imaging module 100 assembled in socket 104 in accordance with an embodiment of the disclosure.

Motion sensors 194 may be implemented by one or more accelerometers, gyroscopes, or other appropriate devices that may be used to detect movement of host device 102. Motion sensors 194 may be monitored by and provide information to processing module 160 or processor 195 to detect motion. In various embodiments, motion sensors 194 may be implemented as part of host device 102 (as shown in FIG. 1), infrared imaging module 100, or other devices attached to or otherwise interfaced with host device 102.

Processor 195 may be implemented as any appropriate device (e.g., programmable logic device, microcontroller, processor, application specific integrated circuit (ASIC), or other device) that may be used by host device 102 to execute appropriate instructions, such as software instructions provided in memory 196. Display 197 may be used to display captured and/or processed infrared images and/or other images, data, and information. Other components 198 may be used to implement any features of host device 102 as may be desired for various applications (e.g., clocks, temperature sensors, a visible light camera, or other components). In addition, a machine readable medium 193 may be provided for storing non-transitory instructions for loading into memory 196 and execution by processor 195.

In various embodiments, infrared imaging module 100 and socket 104 may be implemented for mass production to facilitate high volume applications, such as for implementation in mobile telephones or other devices (e.g., requiring small form factors). In one embodiment, the combination of infrared imaging module 100 and socket 104 may exhibit overall dimensions of approximately 8.5 mm by 8.5 mm by 5.9 mm while infrared imaging module 100 is installed in socket 104.

Figure 3:
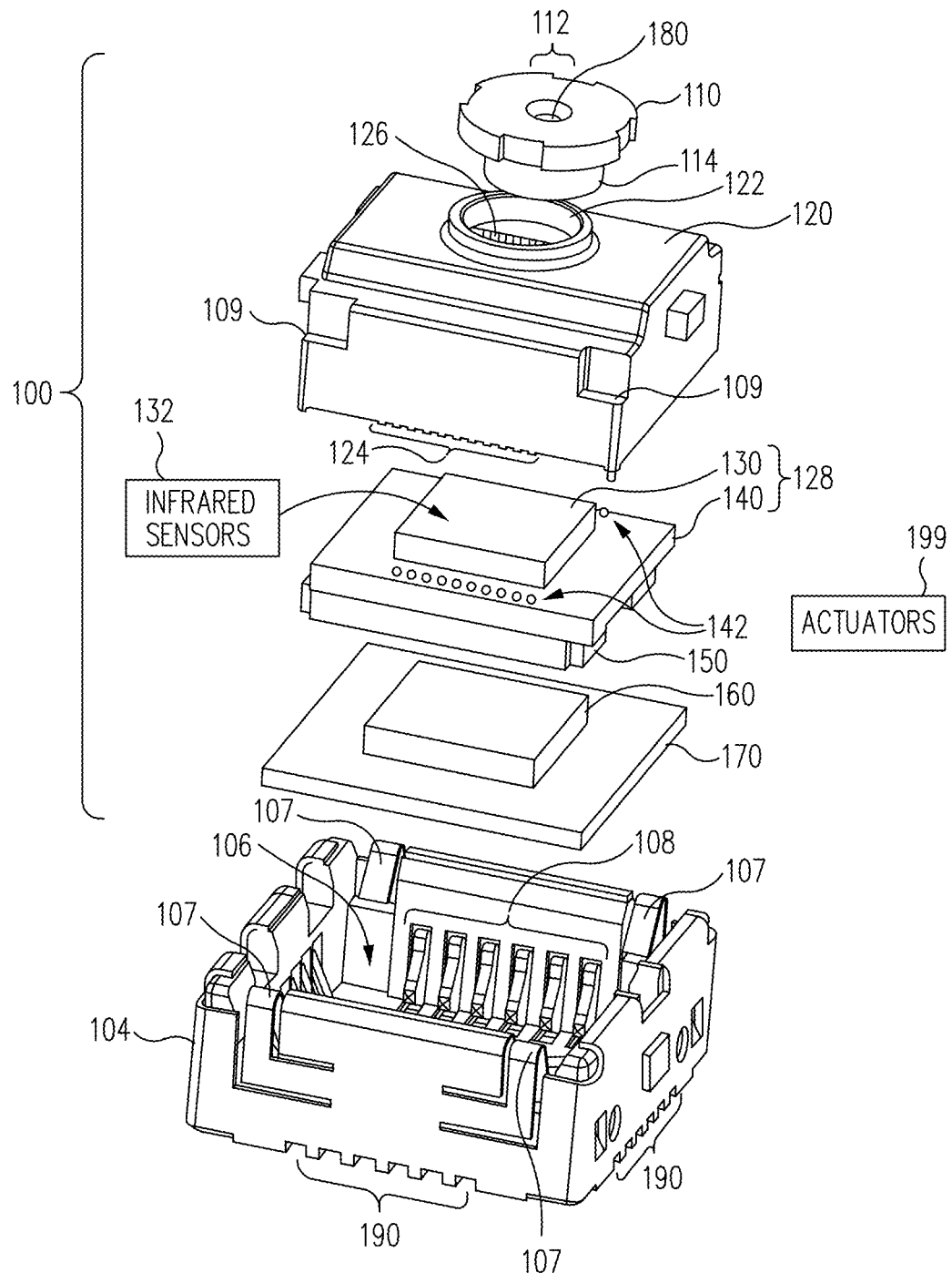
FIG. 3 illustrates an exploded view of an infrared imaging module juxtaposed over a socket in accordance with an embodiment of the disclosure.

FIG. 3 illustrates an exploded view of infrared imaging module 100 juxtaposed over socket 104 in accordance with an embodiment of the disclosure. Infrared imaging module 100 may include a lens barrel 110, a housing 120, an infrared sensor assembly 128, a circuit board 170, a base 150, and a processing module 160.

Lens barrel 110 may at least partially enclose an optical element 180 (e.g., a lens) which is partially visible in FIG. 3 through an aperture 112 in lens barrel 110. Lens barrel 110 may include a substantially cylindrical extension 114 which may be used to interface lens barrel 110 with an aperture 122 in housing 120.

Infrared sensor assembly 128 may be implemented, for example, with a cap 130 (e.g., a lid) mounted on a substrate 140. Infrared sensor assembly 128 may include a plurality of infrared sensors 132 (e.g., infrared detectors) implemented in an array or other fashion on substrate 140 and covered by cap 130. For example, in one embodiment, infrared sensor assembly 128 may be implemented as a focal plane array (FPA). Such a focal plane array may be implemented, for example, as a vacuum package assembly (e.g., sealed by cap 130 and substrate 140). In one embodiment, infrared sensor assembly 128 may be implemented as a wafer level package (e.g., infrared sensor assembly 128 may be singulated from a set of vacuum package assemblies provided on a wafer). In one embodiment, infrared sensor assembly 128 may be implemented to operate using a power supply of approximately 2.4 volts, 2.5 volts, 2.8 volts, or similar voltages.

Infrared sensors 132 may be configured to detect infrared radiation (e.g., infrared energy) from a target scene including, for example, mid wave infrared wave bands (MWIR), long wave infrared wave bands (LWIR), and/or other thermal imaging bands as may be desired in particular implementations. In one embodiment, infrared sensor assembly 128 may be provided in accordance with wafer level packaging techniques.

Infrared sensors 132 may be implemented, for example, as microbolometers or other types of thermal imaging infrared sensors arranged in any desired array pattern to provide a plurality of pixels. In one embodiment, infrared sensors 132 may be implemented as vanadium oxide (VOx) detectors with a 17 μm pixel pitch. In various embodiments, arrays of approximately 32 by 32 infrared sensors 132, approximately 64 by 64 infrared sensors 132, approximately 80 by 64 infrared sensors 132, or other array sizes may be used.

Substrate 140 may include various circuitry including, for example, a read out integrated circuit (ROIC) with dimensions less than approximately 5.5 mm by 5.5 mm in one embodiment. Substrate 140 may also include bond pads 142 that may be used to contact complementary connections positioned on inside surfaces of housing 120 when infrared imaging module 100 is assembled as shown in FIGS. 5A, 5B, and 5C. In one embodiment, the ROIC may be implemented with low-dropout regulators (LDO) to perform voltage regulation to reduce power supply noise introduced to infrared sensor assembly 128 and thus provide an improved power supply rejection ratio (PSRR). Moreover, by implementing the LDO with the ROIC (e.g., within a wafer level package), less die area may be consumed and fewer discrete die (or chips) are needed.

Figure 4:
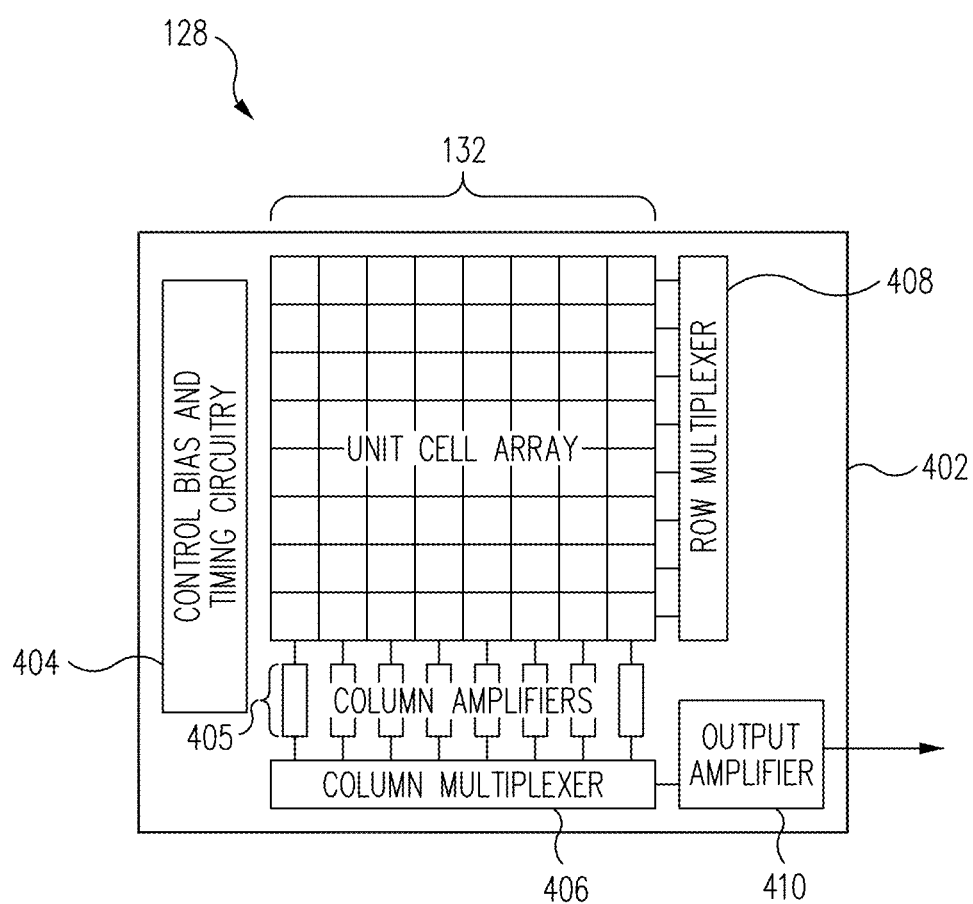
FIG. 4 illustrates a block diagram of an infrared sensor assembly including an array of infrared sensors in accordance with an embodiment of the disclosure.

FIG. 4 illustrates a block diagram of infrared sensor assembly 128 including an array of infrared sensors 132 in accordance with an embodiment of the disclosure. In the illustrated embodiment, infrared sensors 132 are provided as part of a unit cell array of a ROIC 402. ROIC 402 includes bias generation and timing control circuitry 404, column amplifiers 405, a column multiplexer 406, a row multiplexer 408, and an output amplifier 410. Image frames (e.g., thermal images) captured by infrared sensors 132 may be provided by output amplifier 410 to processing module 160, processor 195, and/or any other appropriate components to perform various processing techniques described herein. Although an 8 by 8 array is shown in FIG. 4, any desired array configuration may be used in other embodiments. Further descriptions of ROICs and infrared sensors (e.g., microbolometer circuits) may be found in U.S. Pat. No. 6,028,309 issued Feb. 22, 2000, which is incorporated herein by reference in its entirety.

Infrared sensor assembly 128 may capture images (e.g., image frames) and provide such images from its ROIC at various rates. Processing module 160 may be used to perform appropriate processing of captured infrared images and may be implemented in accordance with any appropriate architecture. In one embodiment, processing module 160 may be implemented as an ASIC. In this regard, such an ASIC may be configured to perform image processing with high performance and/or high efficiency. In another embodiment, processing module 160 may be implemented with a general purpose central processing unit (CPU) which may be configured to execute appropriate software instructions to perform image processing, coordinate and perform image processing with various image processing blocks, coordinate interfacing between processing module 160 and host device 102, and/or other operations. In yet another embodiment, processing module 160 may be implemented with a field programmable gate array (FPGA). Processing module 160 may be implemented with other types of processing and/or logic circuits in other embodiments as would be understood by one skilled in the art.

In these and other embodiments, processing module 160 may also be implemented with other components where appropriate, such as, volatile memory, non-volatile memory, and/or one or more interfaces (e.g., infrared detector interfaces, inter-integrated circuit (I2C) interfaces, mobile industry processor interfaces (MIPI), joint test action group (JTAG) interfaces (e.g., IEEE 1149.1 standard test access port and boundary-scan architecture), and/or other interfaces).

In some embodiments, infrared imaging module 100 may further include one or more actuators 199 which may be used to adjust the focus of infrared image frames captured by infrared sensor assembly 128. For example, actuators 199 may be used to move optical element 180, infrared sensors 132, and/or other components relative to each other to selectively focus and defocus infrared image frames in accordance with techniques described herein. Actuators 199 may be implemented in accordance with any type of motion-inducing apparatus or mechanism, and may positioned at any location within or external to infrared imaging module 100 as appropriate for different applications.

When infrared imaging module 100 is assembled, housing 120 may substantially enclose infrared sensor assembly 128, base 150, and processing module 160. Housing 120 may facilitate connection of various components of infrared imaging module 100. For example, in one embodiment, housing 120 may provide electrical connections 126 to connect various components as further described.

Electrical connections 126 (e.g., conductive electrical paths, traces, or other types of connections) may be electrically connected with bond pads 142 when infrared imaging module 100 is assembled. In various embodiments, electrical connections 126 may be embedded in housing 120, provided on inside surfaces of housing 120, and/or otherwise provided by housing 120. Electrical connections 126 may terminate in connections 124 protruding from the bottom surface of housing 120 as shown in FIG. 3. Connections 124 may connect with circuit board 170 when infrared imaging module 100 is assembled (e.g., housing 120 may rest atop circuit board 170 in various embodiments). Processing module 160 may be electrically connected with circuit board 170 through appropriate electrical connections. As a result, infrared sensor assembly 128 may be electrically connected with processing module 160 through, for example, conductive electrical paths provided by: bond pads 142, complementary connections on inside surfaces of housing 120, electrical connections 126 of housing 120, connections 124, and circuit board 170. Advantageously, such an arrangement may be implemented without requiring wire bonds to be provided between infrared sensor assembly 128 and processing module 160.

In various embodiments, electrical connections 126 in housing 120 may be made from any desired material (e.g., copper or any other appropriate conductive material). In one embodiment, electrical connections 126 may aid in dissipating heat from infrared imaging module 100.

Other connections may be used in other embodiments. For example, in one embodiment, sensor assembly 128 may be attached to processing module 160 through a ceramic board that connects to sensor assembly 128 by wire bonds and to processing module 160 by a ball grid array (BGA). In another embodiment, sensor assembly 128 may be mounted directly on a rigid flexible board and electrically connected with wire bonds, and processing module 160 may be mounted and connected to the rigid flexible board with wire bonds or a BGA.

The various implementations of infrared imaging module 100 and host device 102 set forth herein are provided for purposes of example, rather than limitation. In this regard, any of the various techniques described herein may be applied to any infrared camera system, infrared imager, or other device for performing infrared/thermal imaging.

Substrate 140 of infrared sensor assembly 128 may be mounted on base 150. In various embodiments, base 150 (e.g., a pedestal) may be made, for example, of copper formed by metal injection molding (MIM) and provided with a black oxide or nickel-coated finish. In various embodiments, base 150 may be made of any desired material, such as for example zinc, aluminum, or magnesium, as desired for a given application and may be formed by any desired applicable process, such as for example aluminum casting, MIM, or zinc rapid casting, as may be desired for particular applications. In various embodiments, base 150 may be implemented to provide structural support, various circuit paths, thermal heat sink properties, and other features where appropriate. In one embodiment, base 150 may be a multi-layer structure implemented at least in part using ceramic material.

In various embodiments, circuit board 170 may receive housing 120 and thus may physically support the various components of infrared imaging module 100. In various embodiments, circuit board 170 may be implemented as a printed circuit board (e.g., an FR4 circuit board or other types of circuit boards), a rigid or flexible interconnect (e.g., tape or other type of interconnects), a flexible circuit substrate, a flexible plastic substrate, or other appropriate structures. In various embodiments, base 150 may be implemented with the various features and attributes described for circuit board 170, and vice versa.

Socket 104 may include a cavity 106 configured to receive infrared imaging module 100 (e.g., as shown in the assembled view of FIG. 2). Infrared imaging module 100 and/or socket 104 may include appropriate tabs, arms, pins, fasteners, or any other appropriate engagement members which may be used to secure infrared imaging module 100 to or within socket 104 using friction, tension, adhesion, and/or any other appropriate manner. Socket 104 may include engagement members 107 that may engage surfaces 109 of housing 120 when infrared imaging module 100 is inserted into a cavity 106 of socket 104. Other types of engagement members may be used in other embodiments.

Infrared imaging module 100 may be electrically connected with socket 104 through appropriate electrical connections (e.g., contacts, pins, wires, or any other appropriate connections). For example, socket 104 may include electrical connections 108 which may contact corresponding electrical connections of infrared imaging module 100 (e.g., interconnect pads, contacts, or other electrical connections on side or bottom surfaces of circuit board 170, bond pads 142 or other electrical connections on base 150, or other connections). Electrical connections 108 may be made from any desired material (e.g., copper or any other appropriate conductive material). In one embodiment, electrical connections 108 may be mechanically biased to press against electrical connections of infrared imaging module 100 when infrared imaging module 100 is inserted into cavity 106 of socket 104. In one embodiment, electrical connections 108 may at least partially secure infrared imaging module 100 in socket 104. Other types of electrical connections may be used in other embodiments.

Socket 104 may be electrically connected with host device 102 through similar types of electrical connections. For example, in one embodiment, host device 102 may include electrical connections (e.g., soldered connections, snap-in connections, or other connections) that connect with electrical connections 108 passing through apertures 190. In various embodiments, such electrical connections may be made to the sides and/or bottom of socket 104.

Various components of infrared imaging module 100 may be implemented with flip chip technology which may be used to mount components directly to circuit boards without the additional clearances typically needed for wire bond connections. Flip chip connections may be used, as an example, to reduce the overall size of infrared imaging module 100 for use in compact small form factor applications. For example, in one embodiment, processing module 160 may be mounted to circuit board 170 using flip chip connections. For example, infrared imaging module 100 may be implemented with such flip chip configurations.

In various embodiments, infrared imaging module 100 and/or associated components may be implemented in accordance with various techniques (e.g., wafer level packaging techniques) as set forth in U.S. patent application Ser. No. 12/844,124 filed Jul. 27, 2010, and U.S. Provisional Patent Application No. 61/469,651 filed Mar. 30, 2011, which are incorporated herein by reference in their entirety. Furthermore, in accordance with one or more embodiments, infrared imaging module 100 and/or associated components may be implemented, calibrated, tested, and/or used in accordance with various techniques, such as for example as set forth in U.S. Pat. No. 7,470,902 issued Dec. 30, 2008, U.S. Pat. No. 6,028,309 issued Feb. 22, 2000, U.S. Pat. No. 6,812,465 issued Nov. 2, 2004, U.S. Pat. No. 7,034,301 issued Apr. 25, 2006, U.S. Pat. No. 7,679,048 issued Mar. 16, 2010, U.S. Pat. No. 7,470,904 issued Dec. 30, 2008, U.S. patent application Ser. No. 12/202,880 filed Sep. 2, 2008, and U.S. patent application Ser. No. 12/202,896 filed Sep. 2, 2008, which are incorporated herein by reference in their entirety.

Referring again to FIG. 1, in various embodiments, host device 102 may include shutter 105. In this regard, shutter 105 may be selectively positioned over socket 104 (e.g., as identified by arrows 103) while infrared imaging module 100 is installed therein. In this regard, shutter 105 may be used, for example, to protect infrared imaging module 100 when not in use. Shutter 105 may also be used as a temperature reference as part of a calibration process (e.g., a NUC process or other calibration processes) for infrared imaging module 100 as would be understood by one skilled in the art.

In various embodiments, shutter 105 may be made from various materials such as, for example, polymers, glass, aluminum (e.g., painted or anodized) or other materials. In various embodiments, shutter 105 may include one or more coatings to selectively filter electromagnetic radiation and/or adjust various optical properties of shutter 105 (e.g., a uniform blackbody coating or a reflective gold coating).

In another embodiment, shutter 105 may be fixed in place to protect infrared imaging module 100 at all times. In this case, shutter 105 or a portion of shutter 105 may be made from appropriate materials (e.g., polymers or infrared transmitting materials such as silicon, germanium, zinc selenide, or chalcogenide glasses) that do not substantially filter desired infrared wavelengths. In another embodiment, a shutter may be implemented as part of infrared imaging module 100 (e.g., within or as part of a lens barrel or other components of infrared imaging module 100), as would be understood by one skilled in the art.

Alternatively, in another embodiment, a shutter (e.g., shutter 105 or other type of external or internal shutter) need not be provided, but rather a NUC process or other type of calibration may be performed using shutterless techniques. In another embodiment, a NUC process or other type of calibration using shutterless techniques may be performed in combination with shutter-based techniques.

Infrared imaging module 100 and host device 102 may be implemented in accordance with any of the various techniques set forth in U.S. Provisional Patent Application No. 61/495,873 filed Jun. 10, 2011, U.S. Provisional Patent Application No. 61/495,879 filed Jun. 10, 2011, and U.S. Provisional Patent Application No. 61/495,888 filed Jun. 10, 2011, which are incorporated herein by reference in their entirety.

In various embodiments, the components of host device 102 and/or infrared imaging module 100 may be implemented as a local or distributed system with components in communication with each other over wired and/or wireless networks. Accordingly, the various operations identified in this disclosure may be performed by local and/or remote components as may be desired in particular implementations.

Figure 5:
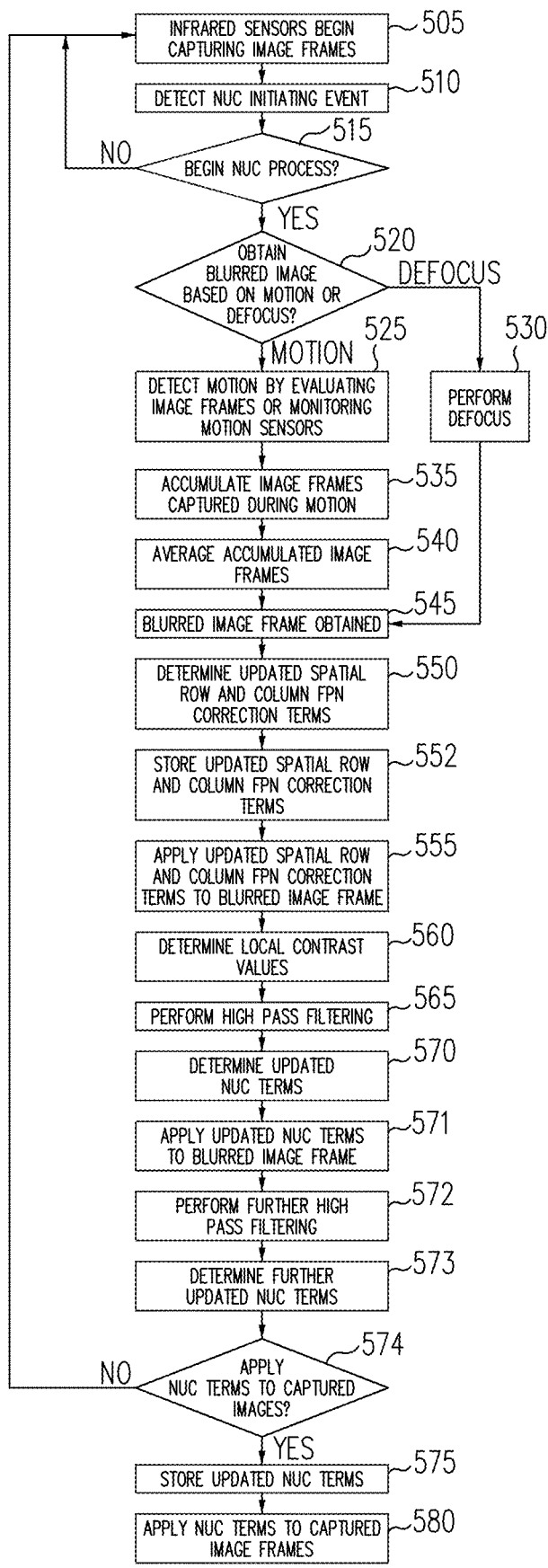
FIG. 5 illustrates a flow diagram of various operations to determine NUC terms in accordance with an embodiment of the disclosure.

FIG. 5 illustrates a flow diagram of various operations to determine NUC terms in accordance with an embodiment of the disclosure. In some embodiments, the operations of FIG. 5 may be performed by processing module 160 or processor 195 (both also generally referred to as a processor) operating on image frames captured by infrared sensors 132.

In block 505, infrared sensors 132 begin capturing image frames of a scene. Typically, the scene will be the real world environment in which host device 102 is currently located. In this regard, shutter 105 (if optionally provided) may be opened to permit infrared imaging module to receive infrared radiation from the scene. Infrared sensors 132 may continue capturing image frames during all operations shown in FIG. 5. In this regard, the continuously captured image frames may be used for various operations as further discussed. In one embodiment, the captured image frames may be temporally filtered (e.g., in accordance with the process of block 826 further described herein with regard to FIG. 8) and be processed by other terms (e.g., factory gain terms 812, factory offset terms 816, previously determined NUC terms 817, column FPN terms 820, and row FPN terms 824 as further described herein with regard to FIG. 8) before they are used in the operations shown in FIG. 5.

In block 510, a NUC process initiating event is detected. In one embodiment, the NUC process may be initiated in response to physical movement of host device 102. Such movement may be detected, for example, by motion sensors 194 which may be polled by a processor. In one example, a user may move host device 102 in a particular manner, such as by intentionally waving host device 102 back and forth in an "erase" or "swipe" movement. In this regard, the user may move host device 102 in accordance with a predetermined speed and direction (velocity), such as in an up and down, side to side, or other pattern to initiate the NUC process. In this example, the use of such movements may permit the user to intuitively operate host device 102 to simulate the "erasing" of noise in captured image frames.

In another example, a NUC process may be initiated by host device 102 if motion exceeding a threshold value is exceeded (e.g., motion greater than expected for ordinary use). It is contemplated that any desired type of spatial translation of host device 102 may be used to initiate the NUC process.

In yet another example, a NUC process may be initiated by host device 102 if a minimum time has elapsed since a previously performed NUC process. In a further example, a NUC process may be initiated by host device 102 if infrared imaging module 100 has experienced a minimum temperature change since a previously performed NUC process. In a still further example, a NUC process may be continuously initiated and repeated.

In block 515, after a NUC process initiating event is detected, it is determined whether the NUC process should actually be performed. In this regard, the NUC process may be selectively initiated based on whether one or more additional conditions are met. For example, in one embodiment, the NUC process may not be performed unless a minimum time has elapsed since a previously performed NUC process. In another embodiment, the NUC process may not be performed unless infrared imaging module 100 has experienced a minimum temperature change since a previously performed NUC process. Other criteria or conditions may be used in other embodiments. If appropriate criteria or conditions have been met, then the flow diagram continues to block 520. Otherwise, the flow diagram returns to block 505.

In the NUC process, blurred image frames may be used to determine NUC terms which may be applied to captured image frames to correct for FPN. As discussed, in one embodiment, the blurred image frames may be obtained by accumulating multiple image frames of a moving scene (e.g., captured while the scene and/or the thermal imager is in motion). In another embodiment, the blurred image frames may be obtained by defocusing an optical element or other component of the thermal imager.

Accordingly, in block 520 a choice of either approach is provided. If the motion-based approach is used, then the flow diagram continues to block 525. If the defocus-based approach is used, then the flow diagram continues to block 530.

Referring now to the motion-based approach, in block 525 motion is detected. For example, in one embodiment, motion may be detected based on the image frames captured by infrared sensors 132. In this regard, an appropriate motion detection process (e.g., an image registration process, a frame-to-frame difference calculation, or other appropriate process) may be applied to captured image frames to determine whether motion is present (e.g., whether static or moving image frames have been captured). For example, in one embodiment, it can be determined whether pixels or regions around the pixels of consecutive image frames have changed more than a user defined amount (e.g., a percentage and/or threshold value). If at least a given percentage of pixels have changed by at least the user defined amount, then motion will be detected with sufficient certainty to proceed to block 535.

In another embodiment, motion may be determined on a per pixel basis, wherein only pixels that exhibit significant changes are accumulated to provide the blurred image frame. For example, counters may be provided for each pixel and used to ensure that the same number of pixel values are accumulated for each pixel, or used to average the pixel values based on the number of pixel values actually accumulated for each pixel. Other types of image-based motion detection may be performed such as performing a Radon transform.

In another embodiment, motion may be detected based on data provided by motion sensors 194. In one embodiment, such motion detection may include detecting whether host device 102 is moving along a relatively straight trajectory through space. For example, if host device 102 is moving along a relatively straight trajectory, then it is possible that certain objects appearing in the imaged scene may not be sufficiently blurred (e.g., objects in the scene that may be aligned with or moving substantially parallel to the straight trajectory). Thus, in such an embodiment, the motion detected by motion sensors 194 may be conditioned on host device 102 exhibiting, or not exhibiting, particular trajectories.

In yet another embodiment, both a motion detection process and motion sensors 194 may be used. Thus, using any of these various embodiments, a determination can be made as to whether or not each image frame was captured while at least a portion of the scene and host device 102 were in motion relative to each other (e.g., which may be caused by host device 102 moving relative to the scene, at least a portion of the scene moving relative to host device 102, or both).

It is expected that the image frames for which motion was detected may exhibit some secondary blurring of the captured scene (e.g., blurred thermal image data associated with the scene) due to the thermal time constants of infrared sensors 132 (e.g., microbolometer thermal time constants) interacting with the scene movement.

In block 535, image frames for which motion was detected are accumulated. For example, if motion is detected for a continuous series of image frames, then the image frames of the series may be accumulated. As another example, if motion is detected for only some image frames, then the non-moving image frames may be skipped and not included in the accumulation. Thus, a continuous or discontinuous set of image frames may be selected to be accumulated based on the detected motion.

In block 540, the accumulated image frames are averaged to provide a blurred image frame. Because the accumulated image frames were captured during motion, it is expected that actual scene information will vary between the image frames and thus cause the scene information to be further blurred in the resulting blurred image frame (block 545).

In contrast, FPN (e.g., caused by one or more components of infrared imaging module 100) will remain fixed over at least short periods of time and over at least limited changes in scene irradiance during motion. As a result, image frames captured in close proximity in time and space during motion will suffer from identical or at least very similar FPN. Thus, although scene information may change in consecutive image frames, the FPN will stay essentially constant. By averaging, multiple image frames captured during motion will blur the scene information, but will not blur the FPN. As a result, FPN will remain more clearly defined in the blurred image frame provided in block 545 than the scene information.

In one embodiment, 32 or more image frames are accumulated and averaged in blocks 535 and 540. However, any desired number of image frames may be used in other embodiments, but with generally decreasing correction accuracy as frame count is decreased.

Referring now to the defocus-based approach, in block 530, a defocus operation may be performed to intentionally defocus the image frames captured by infrared sensors 132. For example, in one embodiment, one or more actuators 199 may be used to adjust, move, or otherwise translate optical element 180, infrared sensor assembly 128, and/or other components of infrared imaging module 100 to cause infrared sensors 132 to capture a blurred (e.g., unfocused) image frame of the scene. Other non-actuator based techniques are also contemplated for intentionally defocusing infrared image frames such as, for example, manual (e.g., user-initiated) defocusing.

Although the scene may appear blurred in the image frame, FPN (e.g., caused by one or more components of infrared imaging module 100) will remain unaffected by the defocusing operation. As a result, a blurred image frame of the scene will be provided (block 545) with FPN remaining more clearly defined in the blurred image than the scene information.

In the above discussion, the defocus-based approach has been described with regard to a single captured image frame. In another embodiment, the defocus-based approach may include accumulating multiple image frames while the infrared imaging module 100 has been defocused and averaging the defocused image frames to remove the effects of temporal noise and provide a blurred image frame in block 545.

Thus, it will be appreciated that a blurred image frame may be provided in block 545 by either the motion-based approach or the defocus-based approach. Because much of the scene information will be blurred by either motion, defocusing, or both, the blurred image frame may be effectively considered a low pass filtered version of the original captured image frames with respect to scene information.

In block 550, the blurred image frame is processed to determine updated row and column FPN terms (e.g., if row and column FPN terms have not been previously determined then the updated row and column FPN terms may be new row and column FPN terms in the first iteration of block 550). As used in this disclosure, the terms row and column may be used interchangeably depending on the orientation of infrared sensors 132 and/or other components of infrared imaging module 100.

In one embodiment, block 550 includes determining a spatial FPN correction term for each row of the blurred image frame (e.g., each row may have its own spatial FPN correction term), and also determining a spatial FPN correction term for each column of the blurred image frame (e.g., each column may have its own spatial FPN correction term). Such processing may be used to reduce the spatial and slowly varying (1/f) row and column FPN inherent in thermal imagers caused by, for example, 1/f noise characteristics of amplifiers in ROIC 402 which may manifest as vertical and horizontal stripes in image frames.

Advantageously, by determining spatial row and column FPN terms using the blurred image frame, there will be a reduced risk of vertical and horizontal objects in the actual imaged scene from being mistaken for row and column noise (e.g., real scene content will be blurred while FPN remains unblurred).

Figure 6:
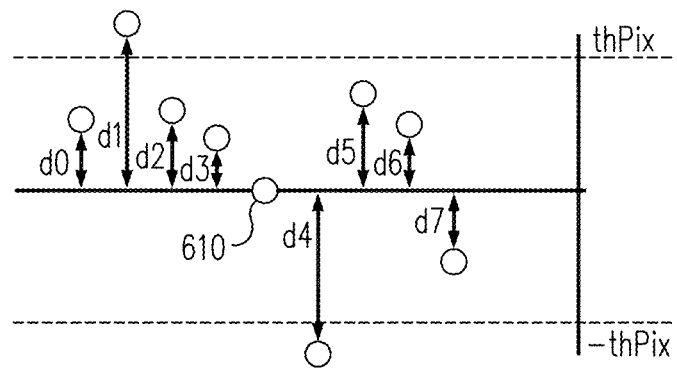
FIG. 6 illustrates differences between neighboring pixels in accordance with an embodiment of the disclosure.

In one embodiment, row and column FPN terms may be determined by considering differences between neighboring pixels of the blurred image frame. For example, FIG. 6 illustrates differences between neighboring pixels in accordance with an embodiment of the disclosure. Specifically, in FIG. 6 a pixel 610 is compared to its 8 nearest horizontal neighbors: d0-d3 on one side and d4-d7 on the other side. Differences between the neighbor pixels can be averaged to obtain an estimate of the offset error of the illustrated group of pixels. An offset error may be calculated for each pixel in a row or column and the average result may be used to correct the entire row or column.

To prevent real scene data from being interpreted as noise, upper and lower threshold values may be used (thPix and −thPix). Pixel values falling outside these threshold values (pixels d1 and d4 in this example) are not used to obtain the offset error. In addition, the maximum amount of row and column FPN correction may be limited by these threshold values.

Further techniques for performing spatial row and column FPN correction processing are set forth in U.S. patent application Ser. No. 12/396,340 filed Mar. 2, 2009 which is incorporated herein by reference in its entirety.

Referring again to FIG. 5, the updated row and column FPN terms determined in block 550 are stored (block 552) and applied (block 555) to the blurred image frame provided in block 545. After these terms are applied, some of the spatial row and column FPN in the blurred image frame may be reduced. However, because such terms are applied generally to rows and columns, additional FPN may remain such as spatially uncorrelated FPN associated with pixel to pixel drift or other causes. Neighborhoods of spatially correlated FPN may also remain which may not be directly associated with individual rows and columns. Accordingly, further processing may be performed as discussed below to determine NUC terms.

In block 560, local contrast values (e.g., edges or absolute values of gradients between adjacent or small groups of pixels) in the blurred image frame are determined. If scene information in the blurred image frame includes contrasting areas that have not been significantly blurred (e.g., high contrast edges in the original scene data), then such features may be identified by a contrast determination process in block 560.

For example, local contrast values in the blurred image frame may be calculated, or any other desired type of edge detection process may be applied to identify certain pixels in the blurred image as being part of an area of local contrast. Pixels that are marked in this manner may be considered as containing excessive high spatial frequency scene information that would be interpreted as FPN (e.g., such regions may correspond to portions of the scene that have not been sufficiently blurred). As such, these pixels may be excluded from being used in the further determination of NUC terms. In one embodiment, such contrast detection processing may rely on a threshold that is higher than the expected contrast value associated with FPN (e.g., pixels exhibiting a contrast value higher than the threshold may be considered to be scene information, and those lower than the threshold may be considered to be exhibiting FPN).

In one embodiment, the contrast determination of block 560 may be performed on the blurred image frame after row and column FPN terms have been applied to the blurred image frame (e.g., as shown in FIG. 5). In another embodiment, block 560 may be performed prior to block 550 to determine contrast before row and column FPN terms are determined (e.g., to prevent scene based contrast from contributing to the determination of such terms).

Following block 560, it is expected that any high spatial frequency content remaining in the blurred image frame may be generally attributed to spatially uncorrelated FPN. In this regard, following block 560, much of the other noise or actual desired scene based information has been removed or excluded from the blurred image frame due to: intentional blurring of the image frame (e.g., by motion or defocusing in blocks 520 through 545), application of row and column FPN terms (block 555), and contrast determination (block 560).

Thus, it can be expected that following block 560, any remaining high spatial frequency content (e.g., exhibited as areas of contrast or differences in the blurred image frame) may be attributed to spatially uncorrelated FPN. Accordingly, in block 565, the blurred image frame is high pass filtered. In one embodiment, this may include applying a high pass filter to extract the high spatial frequency content from the blurred image frame. In another embodiment, this may include applying a low pass filter to the blurred image frame and taking a difference between the low pass filtered image frame and the unfiltered blurred image frame to obtain the high spatial frequency content. In accordance with various embodiments of the present disclosure, a high pass filter may be implemented by calculating a mean difference between a sensor signal (e.g., a pixel value) and its neighbors.

In block 570, a flat field correction process is performed on the high pass filtered blurred image frame to determine updated NUC terms (e.g., if a NUC process has not previously been performed then the updated NUC terms may be new NUC terms in the first iteration of block 570).

Figure 7:
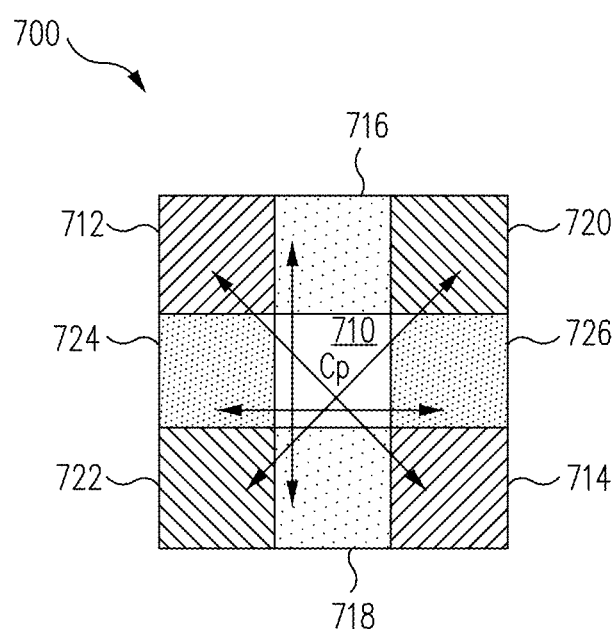
FIG. 7 illustrates a flat field correction technique in accordance with an embodiment of the disclosure.

For example, FIG. 7 illustrates a flat field correction technique 700 in accordance with an embodiment of the disclosure. In FIG. 7, a NUC term may be determined for each pixel 710 of the blurred image frame using the values of its neighboring pixels 712 to 726. For each pixel 710, several gradients may be determined based on the absolute difference between the values of various adjacent pixels. For example, absolute value differences may be determined between: pixels 712 and 714 (a left to right diagonal gradient), pixels 716 and 718 (a top to bottom vertical gradient), pixels 720 and 722 (a right to left diagonal gradient), and pixels 724 and 726 (a left to right horizontal gradient).

These absolute differences may be summed to provide a summed gradient for pixel 710. A weight value may be determined for pixel 710 that is inversely proportional to the summed gradient. This process may be performed for all pixels 710 of the blurred image frame until a weight value is provided for each pixel 710. For areas with low gradients (e.g., areas that are blurry or have low contrast), the weight value will be close to one. Conversely, for areas with high gradients, the weight value will be zero or close to zero. The update to the NUC term as estimated by the high pass filter is multiplied with the weight value.

In one embodiment, the risk of introducing scene information into the NUC terms can be further reduced by applying some amount of temporal damping to the NUC term determination process. For example, a temporal damping factor λ between 0 and 1 may be chosen such that the new NUC term ($NUC_{NEW}$) stored is a weighted average of the old NUC term ($NUC_{OLD}$) and the estimated updated NUC term ($NUC_{UPDATE}$). In one embodiment, this can be expressed as $NUC_{NEW}=\lambda \cdot NUC_{OLD}+(1-\lambda) \cdot (NUC_{OLD}+NUC_{UPDATE})$.

Although the determination of NUC terms has been described with regard to gradients, local contrast values may be used instead where appropriate. Other techniques may also be used such as, for example, standard deviation calculations. Other types flat field correction processes may be performed to determine NUC terms including, for example, various processes identified in U.S. Pat. No. 6,028,309 issued Feb. 22, 2000, U.S. Pat. No. 6,812,465 issued Nov. 2, 2004, and U.S. patent application Ser. No. 12/114,865 filed May 5, 2008, which are incorporated herein by reference in their entirety.

Referring again to FIG. 5, block 570 may include additional processing of the NUC terms. For example, in one embodiment, to preserve the scene signal mean, the sum of all NUC terms may be normalized to zero by subtracting the NUC term mean from each NUC term. Also in block 570, to avoid row and column noise from affecting the NUC terms, the mean value of each row and column may be subtracted from the NUC terms for each row and column. As a result, row and column FPN filters using the row and column FPN terms determined in block 550 may be better able to filter out row and column noise in further iterations (e.g., as further shown in FIG. 8) after the NUC terms are applied to captured images (e.g., in block 580 further discussed herein). In this regard, the row and column FPN filters may in general use more data to calculate the per row and per column offset coefficients (e.g., row and column FPN terms) and may thus provide a more robust alternative for reducing spatially correlated FPN than the NUC terms which are based on high pass filtering to capture spatially uncorrelated noise.

In blocks 571-573, additional high pass filtering and further determinations of updated NUC terms may be optionally performed to remove spatially correlated FPN with lower spatial frequency than previously removed by row and column FPN terms. In this regard, some variability in infrared sensors 132 or other components of infrared imaging module 100 may result in spatially correlated FPN noise that cannot be easily modeled as row or column noise. Such spatially correlated FPN may include, for example, window defects on a sensor package or a cluster of infrared sensors 132 that respond differently to irradiance than neighboring infrared sensors 132. In one embodiment, such spatially correlated FPN may be mitigated with an offset correction. If the amount of such spatially correlated FPN is significant, then the noise may also be detectable in the blurred image frame. Since this type of noise may affect a neighborhood of pixels, a high pass filter with a small kernel may not detect the FPN in the neighborhood (e.g., all values used in high pass filter may be taken from the neighborhood of affected pixels and thus may be affected by the same offset error). For example, if the high pass filtering of block 565 is performed with a small kernel (e.g., considering only immediately adjacent pixels that fall within a neighborhood of pixels affected by spatially correlated FPN), then broadly distributed spatially correlated FPN may not be detected.

Figure 11:
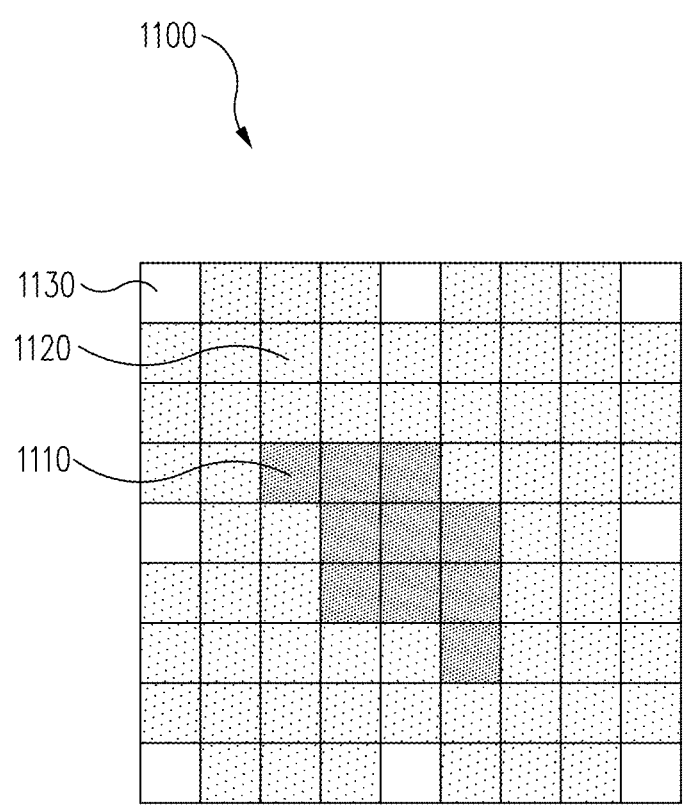
FIG. 11 illustrates spatially correlated FPN in a neighborhood of pixels in accordance with an embodiment of the disclosure.

For example, FIG. 11 illustrates spatially correlated FPN in a neighborhood of pixels in accordance with an embodiment of the disclosure. As shown in a sample image frame 1100, a neighborhood of pixels 1110 may exhibit spatially correlated FPN that is not precisely correlated to individual rows and columns and is distributed over a neighborhood of several pixels (e.g., a neighborhood of approximately 4 by 4 pixels in this example). Sample image frame 1100 also includes a set of pixels 1120 exhibiting substantially uniform response that are not used in filtering calculations, and a set of pixels 1130 that are used to estimate a low pass value for the neighborhood of pixels 1110. In one embodiment, pixels 1130 may be a number of pixels divisible by two in order to facilitate efficient hardware or software calculations.

Referring again to FIG. 5, in blocks 571-573, additional high pass filtering and further determinations of updated NUC terms may be optionally performed to remove spatially correlated FPN such as exhibited by pixels 1110. In block 571, the updated NUC terms determined in block 570 are applied to the blurred image frame. Thus, at this time, the blurred image frame will have been initially corrected for spatially correlated FPN (e.g., by application of the updated row and column FPN terms in block 555), and also initially corrected for spatially uncorrelated FPN (e.g., by application of the updated NUC terms applied in block 571).

In block 572, a further high pass filter is applied with a larger kernel than was used in block 565, and further updated NUC terms may be determined in block 573. For example, to detect the spatially correlated FPN present in pixels 1110, the high pass filter applied in block 572 may include data from a sufficiently large enough neighborhood of pixels such that differences can be determined between unaffected pixels (e.g., pixels 1120) and affected pixels (e.g., pixels 1110). For example, a low pass filter with a large kernel can be used (e.g., an N by N kernel that is much greater than 3 by 3 pixels) and the results may be subtracted to perform appropriate high pass filtering.

In one embodiment, for computational efficiency, a sparse kernel may be used such that only a small number of neighboring pixels inside an N by N neighborhood are used. For any given high pass filter operation using distant neighbors (e.g., a large kernel), there is a risk of modeling actual (potentially blurred) scene information as spatially correlated FPN. Accordingly, in one embodiment, the temporal damping factor λ may be set close to 1 for updated NUC terms determined in block 573.

In various embodiments, blocks 571-573 may be repeated (e.g., cascaded) to iteratively perform high pass filtering with increasing kernel sizes to provide further updated NUC terms further correct for spatially correlated FPN of desired neighborhood sizes. In one embodiment, the decision to perform such iterations may be determined by whether spatially correlated FPN has actually been removed by the updated NUC terms of the previous performance of blocks 571-573.

After blocks 571-573 are finished, a decision is made regarding whether to apply the updated NUC terms to captured image frames (block 574). For example, if an average of the absolute value of the NUC terms for the entire image frame is less than a minimum threshold value, or greater than a maximum threshold value, the NUC terms may be deemed spurious or unlikely to provide meaningful correction. Alternatively, thresholding criteria may be applied to individual pixels to determine which pixels receive updated NUC terms. In one embodiment, the threshold values may correspond to differences between the newly calculated NUC terms and previously calculated NUC terms. In another embodiment, the threshold values may be independent of previously calculated NUC terms. Other tests may be applied (e.g., spatial correlation tests) to determine whether the NUC terms should be applied.

If the NUC terms are deemed spurious or unlikely to provide meaningful correction, then the flow diagram returns to block 505. Otherwise, the newly determined NUC terms are stored (block 575) to replace previous NUC terms (e.g., determined by a previously performed iteration of FIG. 5) and applied (block 580) to captured image frames.

Figure 8:
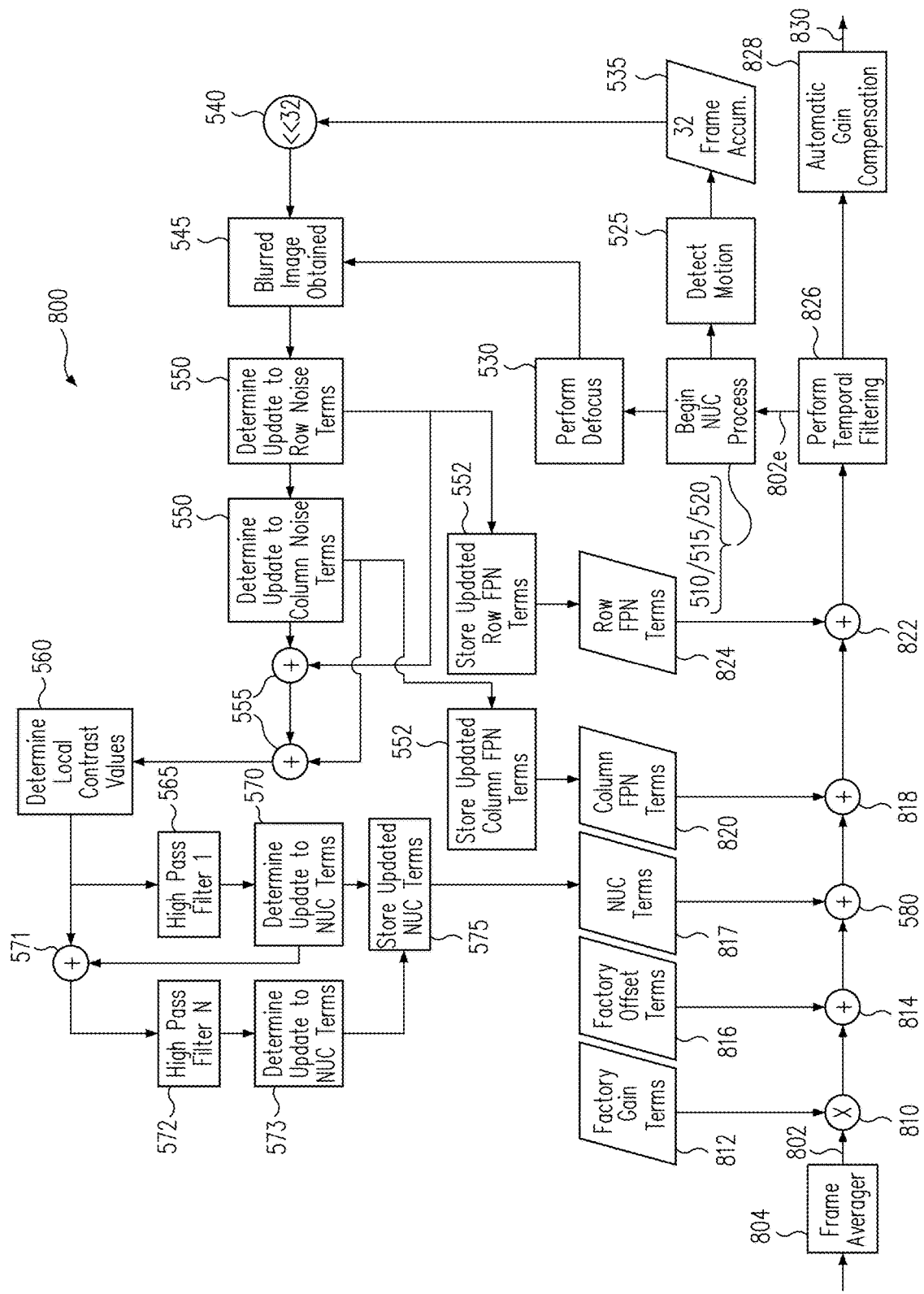
FIG. 8 illustrates various image processing techniques of FIG. 5 and other operations applied in an image processing pipeline in accordance with an embodiment of the disclosure.

FIG. 8 illustrates various image processing techniques of FIG. 5 and other operations applied in an image processing pipeline 800 in accordance with an embodiment of the disclosure. In this regard, pipeline 800 identifies various operations of FIG. 5 in the context of an overall iterative image processing scheme for correcting image frames provided by infrared imaging module 100. In some embodiments, pipeline 800 may be provided by processing module 160 or processor 195 (both also generally referred to as a processor) operating on image frames captured by infrared sensors 132.

Image frames captured by infrared sensors 132 may be provided to a frame averager 804 that integrates multiple image frames to provide image frames 802 with an improved signal to noise ratio. Frame averager 804 may be effectively provided by infrared sensors 132, ROIC 402, and other components of infrared sensor assembly 128 that are implemented to support high image capture rates. For example, in one embodiment, infrared sensor assembly 128 may capture infrared image frames at a frame rate of 240 Hz (e.g., 240 images per second). In this embodiment, such a high frame rate may be implemented, for example, by operating infrared sensor assembly 128 at relatively low voltages (e.g., compatible with mobile telephone voltages) and by using a relatively small array of infrared sensors 132 (e.g., an array of 64 by 64 infrared sensors in one embodiment).

In one embodiment, such infrared image frames may be provided from infrared sensor assembly 128 to processing module 160 at a high frame rate (e.g., 240 Hz or other frame rates). In another embodiment, infrared sensor assembly 128 may integrate over longer time periods, or multiple time periods, to provide integrated (e.g., averaged) infrared image frames to processing module 160 at a lower frame rate (e.g., 30 Hz, 9 Hz, or other frame rates). Further information regarding implementations that may be used to provide high image capture rates may be found in U.S. Provisional Patent Application No. 61/495,879 previously referenced herein.

Image frames 802 proceed through pipeline 800 where they are adjusted by various terms, temporally filtered, used to determine the various adjustment terms, and gain compensated.

In blocks 810 and 814, factory gain terms 812 and factory offset terms 816 are applied to image frames 802 to compensate for gain and offset differences, respectively, between the various infrared sensors 132 and/or other components of infrared imaging module 100 determined during manufacturing and testing.

In block 580, NUC terms 817 are applied to image frames 802 to correct for FPN as discussed. In one embodiment, if NUC terms 817 have not yet been determined (e.g., before a NUC process has been initiated), then block 580 may not be performed or initialization values may be used for NUC terms 817 that result in no alteration to the image data (e.g., offsets for every pixel would be equal to zero).

In blocks 818 and 822, column FPN terms 820 and row FPN terms 824, respectively, are applied to image frames 802. Column FPN terms 820 and row FPN terms 824 may be determined in accordance with block 550 as discussed. In one embodiment, if the column FPN terms 820 and row FPN terms 824 have not yet been determined (e.g., before a NUC process has been initiated), then blocks 818 and 822 may not be performed or initialization values may be used for the column FPN terms 820 and row FPN terms 824 that result in no alteration to the image data (e.g., offsets for every pixel would be equal to zero).

Figure 9:
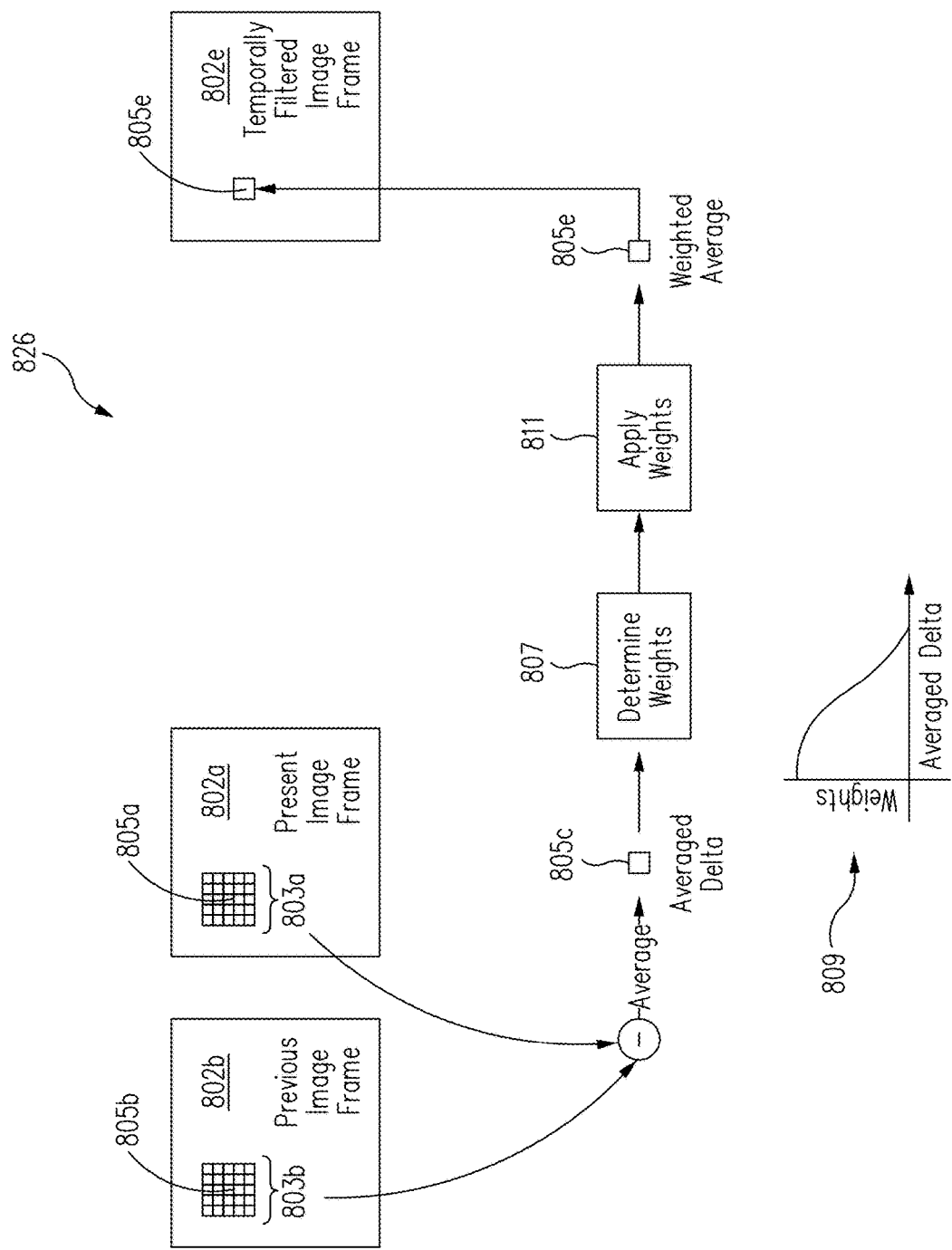
FIG. 9 illustrates a temporal noise reduction process in accordance with an embodiment of the disclosure.

In block 826, temporal filtering is performed on image frames 802 in accordance with a temporal noise reduction (TNR) process. FIG. 9 illustrates a TNR process in accordance with an embodiment of the disclosure. In FIG. 9, a presently received image frame 802a and a previously temporally filtered image frame 802b are processed to determine a new temporally filtered image frame 802e. Image frames 802a and 802b include local neighborhoods of pixels 803a and 803b centered around pixels 805a and 805b, respectively. Neighborhoods 803a and 803b correspond to the same locations within image frames 802a and 802b and are subsets of the total pixels in image frames 802a and 802b. In the illustrated embodiment, neighborhoods 803a and 803b include areas of 5 by 5 pixels. Other neighborhood sizes may be used in other embodiments.

Differences between corresponding pixels of neighborhoods 803a and 803b are determined and averaged to provide an averaged delta value 805c for the location corresponding to pixels 805a and 805b. Averaged delta value 805c may be used to determine weight values in block 807 to be applied to pixels 805a and 805b of image frames 802a and 802b.

In one embodiment, as shown in graph 809, the weight values determined in block 807 may be inversely proportional to averaged delta value 805c such that weight values drop rapidly towards zero when there are large differences between neighborhoods 803a and 803b. In this regard, large differences between neighborhoods 803a and 803b may indicate that changes have occurred within the scene (e.g., due to motion) and pixels 802a and 802b may be appropriately weighted, in one embodiment, to avoid introducing blur across frame-to-frame scene changes. Other associations between weight values and averaged delta value 805c may be used in various embodiments.

The weight values determined in block 807 may be applied to pixels 805a and 805b to determine a value for corresponding pixel 805e of image frame 802e (block 811). In this regard, pixel 805e may have a value that is a weighted average (or other combination) of pixels 805a and 805b, depending on averaged delta value 805c and the weight values determined in block 807.

For example, pixel 805e of temporally filtered image frame 802e may be a weighted sum of pixels 805a and 805b of image frames 802a and 802b. If the average difference between pixels 805a and 805b is due to noise, then it may be expected that the average change between neighborhoods 805a and 805b will be close to zero (e.g., corresponding to the average of uncorrelated changes). Under such circumstances, it may be expected that the sum of the differences between neighborhoods 805a and 805b will be close to zero. In this case, pixel 805a of image frame 802a may both be appropriately weighted so as to contribute to the value of pixel 805e.

However, if the sum of such differences is not zero (e.g., even differing from zero by a small amount in one embodiment), then the changes may be interpreted as being attributed to motion instead of noise. Thus, motion may be detected based on the average change exhibited by neighborhoods 805a and 805b. Under these circumstances, pixel 805a of image frame 802a may be weighted heavily, while pixel 805b of image frame 802b may be weighted lightly.

Other embodiments are also contemplated. For example, although averaged delta value 805c has been described as being determined based on neighborhoods 805a and 805b, in other embodiments averaged delta value 805c may be determined based on any desired criteria (e.g., based on individual pixels or other types of groups of sets of pixels).

In the above embodiments, image frame 802a has been described as a presently received image frame and image frame 802b has been described as a previously temporally filtered image frame. In another embodiment, image frames 802a and 802b may be first and second image frames captured by infrared imaging module 100 that have not been temporally filtered.

Figure 10:
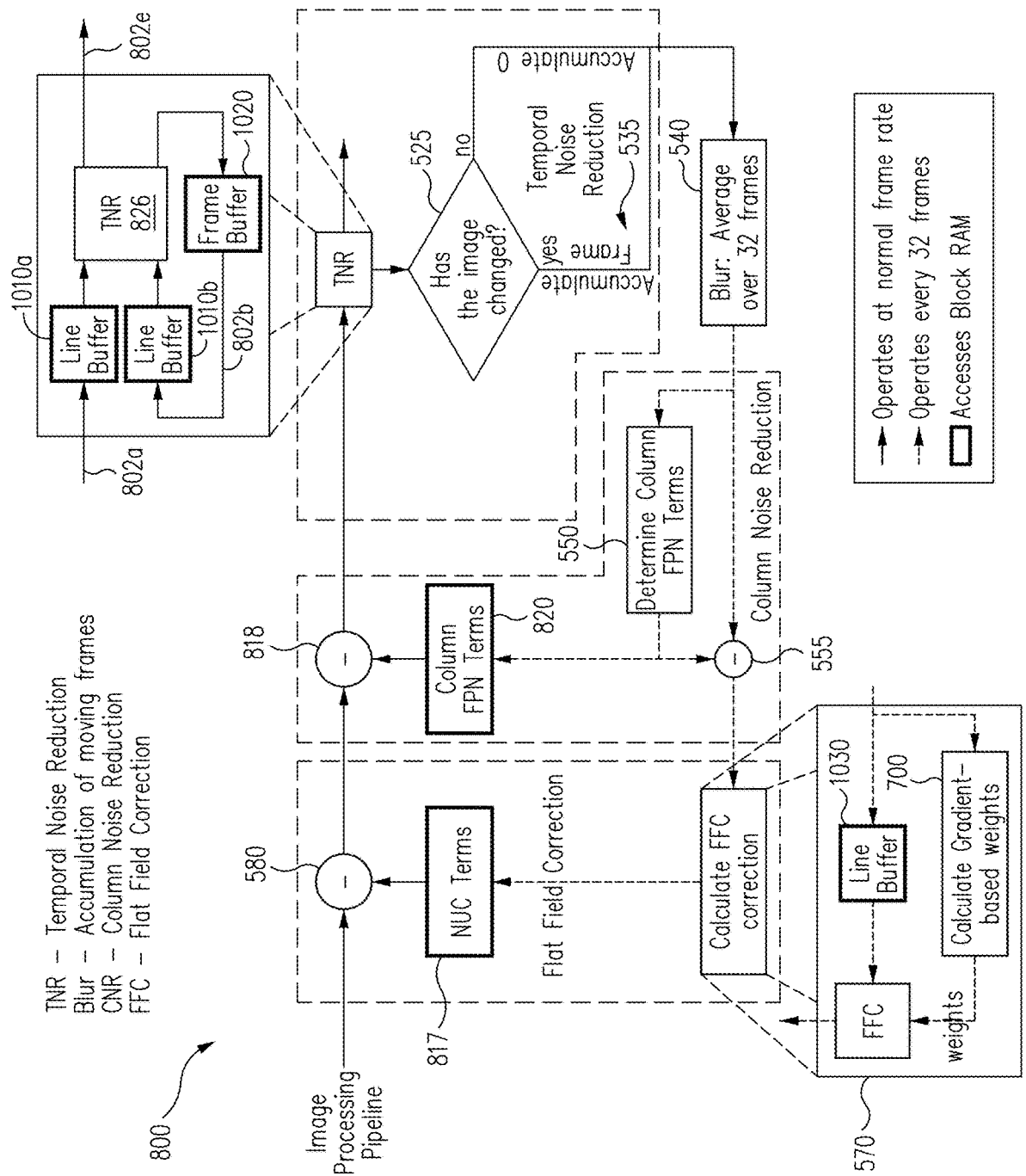
FIG. 10 illustrates particular implementation details of several processes of the image processing pipeline of FIG. 6 in accordance with an embodiment of the disclosure.

FIG. 10 illustrates further implementation details in relation to the TNR process of block 826. As shown in FIG. 10, image frames 802a and 802b may be read into line buffers 1010a and 1010b, respectively, and image frame 802b (e.g., the previous image frame) may be stored in a frame buffer 1020 before being read into line buffer 1010b. In one embodiment, line buffers 1010a-b and frame buffer 1020 may be implemented by a block of random access memory (RAM) provided by any appropriate component of infrared imaging module 100 and/or host device 102.

Referring again to FIG. 8, image frame 802e may be passed to an automatic gain compensation block 828 for further processing to provide a result image frame 830 that may be used by host device 102 as desired.

FIG. 8 further illustrates various operations that may be performed to determine row and column FPN terms and NUC terms as discussed. In one embodiment, these operations may use image frames 802e as shown in FIG. 8. Because image frames 802e have already been temporally filtered, at least some temporal noise may be removed and thus will not inadvertently affect the determination of row and column FPN terms 824 and 820 and NUC terms 817. In another embodiment, non-temporally filtered image frames 802 may be used.

In FIG. 8, blocks 510, 515, and 520 of FIG. 5 are collectively represented together. As discussed, a NUC process may be selectively initiated and performed in response to various NUC process initiating events and based on various criteria or conditions. As also discussed, the NUC process may be performed in accordance with a motion-based approach (blocks 525, 535, and 540) or a defocus-based approach (block 530) to provide a blurred image frame (block 545). FIG. 8 further illustrates various additional blocks 550, 552, 555, 560, 565, 570, 571, 572, 573, and 575 previously discussed with regard to FIG. 5.

As shown in FIG. 8, row and column FPN terms 824 and 820 and NUC terms 817 may be determined and applied in an iterative fashion such that updated terms are determined using image frames 802 to which previous terms have already been applied. As a result, the overall process of FIG. 8 may repeatedly update and apply such terms to continuously reduce the noise in image frames 830 to be used by host device 102.

Referring again to FIG. 10, further implementation details are illustrated for various blocks of FIGS. 5 and 8 in relation to pipeline 800. For example, blocks 525, 535, and 540 are shown as operating at the normal frame rate of image frames 802 received by pipeline 800. In the embodiment shown in FIG. 10, the determination made in block 525 is represented as a decision diamond used to determine whether a given image frame 802 has sufficiently changed such that it may be considered an image frame that will enhance the blur if added to other image frames and is therefore accumulated (block 535 is represented by an arrow in this embodiment) and averaged (block 540).

Also in FIG. 10, the determination of column FPN terms 820 (block 550) is shown as operating at an update rate that in this example is 1/32 of the sensor frame rate (e.g., normal frame rate) due to the averaging performed in block 540. Other update rates may be used in other embodiments. Although only column FPN terms 820 are identified in FIG. 10, row FPN terms 824 may be implemented in a similar fashion at the reduced frame rate.

FIG. 10 also illustrates further implementation details in relation to the NUC determination process of block 570. In this regard, the blurred image frame may be read to a line buffer 1030 (e.g., implemented by a block of RAM provided by any appropriate component of infrared imaging module 100 and/or host device 102). The flat field correction technique 700 of FIG. 7 may be performed on the blurred image frame.

In view of the present disclosure, it will be appreciated that techniques described herein may be used to remove various types of FPN (e.g., including very high amplitude FPN) such as spatially correlated row and column FPN and spatially uncorrelated FPN.

Other embodiments are also contemplated. For example, in one embodiment, the rate at which row and column FPN terms and/or NUC terms are updated can be inversely proportional to the estimated amount of blur in the blurred image frame and/or inversely proportional to the magnitude of local contrast values (e.g., determined in block 560).

In various embodiments, the described techniques may provide advantages over conventional shutter-based noise correction techniques. For example, by using a shutterless process, a shutter (e.g., such as shutter 105) need not be provided, thus permitting reductions in size, weight, cost, and mechanical complexity. Power and maximum voltage supplied to, or generated by, infrared imaging module 100 may also be reduced if a shutter does not need to be mechanically operated. Reliability will be improved by removing the shutter as a potential point of failure. A shutterless process also eliminates potential image interruption caused by the temporary blockage of the imaged scene by a shutter.

Also, by correcting for noise using intentionally blurred image frames captured from a real world scene (not a uniform scene provided by a shutter), noise correction may be performed on image frames that have irradiance levels similar to those of the actual scene desired to be imaged. This can improve the accuracy and effectiveness of noise correction terms determined in accordance with the various described techniques.

As discussed, in various embodiments, infrared imaging module 100 may be configured to operate at low voltage levels. In particular, infrared imaging module 100 may be implemented with circuitry configured to operate at low power and/or in accordance with other parameters that permit infrared imaging module 100 to be conveniently and effectively implemented in various types of host devices 102, such as mobile devices and other devices.

Figure 12:
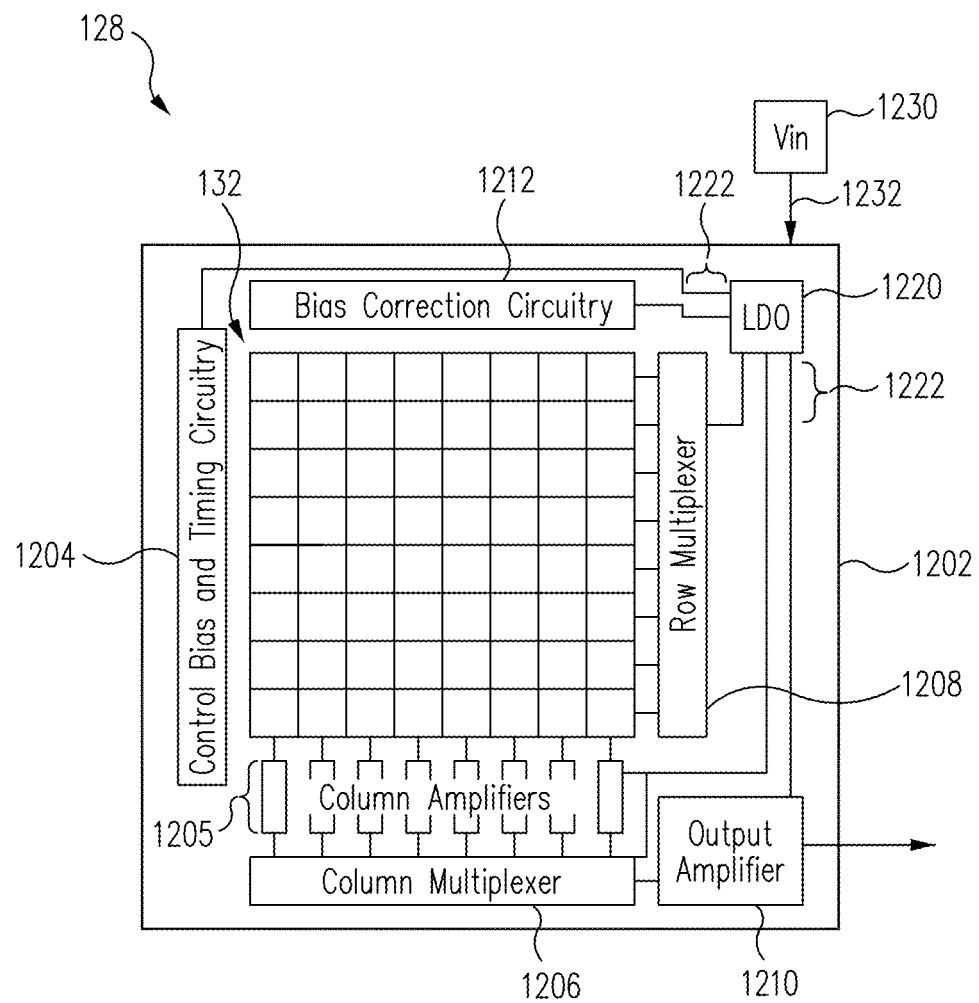
FIG. 12 illustrates a block diagram of another implementation of an infrared sensor assembly including an array of infrared sensors and a low-dropout regulator in accordance with an embodiment of the disclosure.

For example, FIG. 12 illustrates a block diagram of another implementation of infrared sensor assembly 128 including infrared sensors 132 and an LDO 1220 in accordance with an embodiment of the disclosure. As shown, FIG. 12 also illustrates various components 1202, 1204, 1205, 1206, 1208, and 1210 which may implemented in the same or similar manner as corresponding components previously described with regard to FIG. 4. FIG. 12 also illustrates bias correction circuitry 1212 which may be used to adjust one or more bias voltages provided to infrared sensors 132 (e.g., to compensate for temperature changes, self-heating, and/or other factors).

In some embodiments, LDO 1220 may be provided as part of infrared sensor assembly 128 (e.g., on the same chip and/or wafer level package as the ROIC). For example, LDO 1220 may be provided as part of an FPA with infrared sensor assembly 128. As discussed, such implementations may reduce power supply noise introduced to infrared sensor assembly 128 and thus provide an improved PSRR. In addition, by implementing the LDO with the ROIC, less die area may be consumed and fewer discrete die (or chips) are needed.

LDO 1220 receives an input voltage provided by a power source 1230 over a supply line 1232. LDO 1220 provides an output voltage to various components of infrared sensor assembly 128 over supply lines 1222. In this regard, LDO 1220 may provide substantially identical regulated output voltages to various components of infrared sensor assembly 128 in response to a single input voltage received from power source 1230.

For example, in some embodiments, power source 1230 may provide an input voltage in a range of approximately 2.8 volts to approximately 11 volts (e.g., approximately 2.8 volts in one embodiment), and LDO 1220 may provide an output voltage in a range of approximately 1.5 volts to approximately 2.8 volts (e.g., approximately 2.5 volts in one embodiment). In this regard, LDO 1220 may be used to provide a consistent regulated output voltage, regardless of whether power source 1230 is implemented with a conventional voltage range of approximately 9 volts to approximately 11 volts, or a low voltage such as approximately 2.8 volts. As such, although various voltage ranges are provided for the input and output voltages, it is contemplated that the output voltage of LDO 1220 will remain fixed despite changes in the input voltage.

The implementation of LDO 1220 as part of infrared sensor assembly 128 provides various advantages over conventional power implementations for FPAs. For example, conventional FPAs typically rely on multiple power sources, each of which may be provided separately to the FPA, and separately distributed to the various components of the FPA. By regulating a single power source 1230 by LDO 1220, appropriate voltages may be separately provided (e.g., to reduce possible noise) to all components of infrared sensor assembly 128 with reduced complexity. The use of LDO 1220 also allows infrared sensor assembly 128 to operate in a consistent manner, even if the input voltage from power source 1230 changes (e.g., if the input voltage increases or decreases as a result of charging or discharging a battery or other type of device used for power source 1230).

The various components of infrared sensor assembly 128 shown in FIG. 12 may also be implemented to operate at lower voltages than conventional devices. For example, as discussed, LDO 1220 may be implemented to provide a low voltage (e.g., approximately 2.5 volts). This contrasts with the multiple higher voltages typically used to power conventional FPAs, such as: approximately 3.3 volts to approximately 5 volts used to power digital circuitry; approximately 3.3 volts used to power analog circuitry; and approximately 9 volts to approximately 11 volts used to power loads. Also, in some embodiments, the use of LDO 1220 may reduce or eliminate the need for a separate negative reference voltage to be provided to infrared sensor assembly 128.

Figure 13:
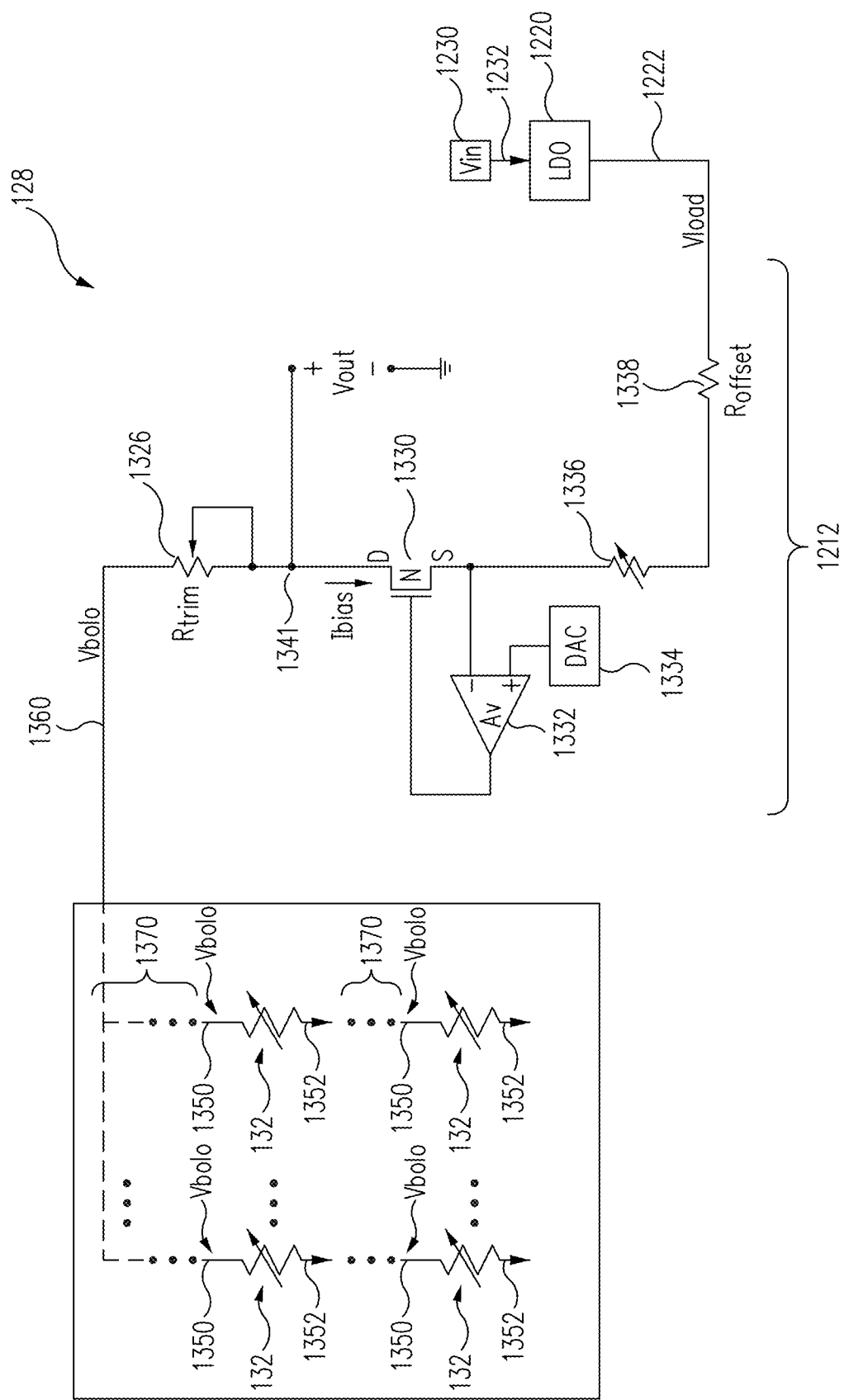
FIG. 13 illustrates a circuit diagram of a portion of the infrared sensor assembly of FIG. 12 in accordance with an embodiment of the disclosure.

Additional aspects of the low voltage operation of infrared sensor assembly 128 may be further understood with reference to FIG. 13. FIG. 13 illustrates a circuit diagram of a portion of infrared sensor assembly 128 of FIG. 12 in accordance with an embodiment of the disclosure. In particular, FIG. 13 illustrates additional components of bias correction circuitry 1212 (e.g., components 1326, 1330, 1332, 1334, 1336, 1338, and 1341) connected to LDO 1220 and infrared sensors 132. For example, bias correction circuitry 1212 may be used to compensate for temperature-dependent changes in bias voltages in accordance with an embodiment of the present disclosure. The operation of such additional components may be further understood with reference to similar components identified in U.S. Pat. No. 7,679,048 issued Mar. 16, 2010 which is hereby incorporated by reference in its entirety. Infrared sensor assembly 128 may also be implemented in accordance with the various components identified in U.S. Pat. No. 6,812,465 issued Nov. 2, 2004 which is hereby incorporated by reference in its entirety.

In various embodiments, some or all of the bias correction circuitry 1212 may be implemented on a global array basis as shown in FIG. 13 (e.g., used for all infrared sensors 132 collectively in an array). In other embodiments, some or all of the bias correction circuitry 1212 may be implemented an individual sensor basis (e.g., entirely or partially duplicated for each infrared sensor 132). In some embodiments, bias correction circuitry 1212 and other components of FIG. 13 may be implemented as part of ROIC 1202.

As shown in FIG. 13, LDO 1220 provides a load voltage Vload to bias correction circuitry 1212 along one of supply lines 1222. As discussed, in some embodiments, Vload may be approximately 2.5 volts which contrasts with larger voltages of approximately 9 volts to approximately 11 volts that may be used as load voltages in conventional infrared imaging devices.

Based on Vload, bias correction circuitry 1212 provides a sensor bias voltage Vbolo at a node 1360. Vbolo may be distributed to one or more infrared sensors 132 through appropriate switching circuitry 1370 (e.g., represented by broken lines in FIG. 13). In some examples, switching circuitry 1370 may be implemented in accordance with appropriate components identified in U.S. Pat. Nos. 6,812,465 and 7,679,048 previously referenced herein.

Each infrared sensor 132 includes a node 1350 which receives Vbolo through switching circuitry 1370, and another node 1352 which may be connected to ground, a substrate, and/or a negative reference voltage. In some embodiments, the voltage at node 1360 may be substantially the same as Vbolo provided at nodes 1350. In other embodiments, the voltage at node 1360 may be adjusted to compensate for possible voltage drops associated with switching circuitry 1370 and/or other factors.

Vbolo may be implemented with lower voltages than are typically used for conventional infrared sensor biasing. In one embodiment, Vbolo may be in a range of approximately 0.2 volts to approximately 0.7 volts. In another embodiment, Vbolo may be in a range of approximately 0.4 volts to approximately 0.6 volts. In another embodiment, Vbolo may be approximately 0.5 volts. In contrast, conventional infrared sensors typically use bias voltages of approximately 1 volt.

The use of a lower bias voltage for infrared sensors 132 in accordance with the present disclosure permits infrared sensor assembly 128 to exhibit significantly reduced power consumption in comparison with conventional infrared imaging devices. In particular, the power consumption of each infrared sensor 132 is reduced by the square of the bias voltage. As a result, a reduction from, for example, 1.0 volt to 0.5 volts provides a significant reduction in power, especially when applied to many infrared sensors 132 in an infrared sensor array. This reduction in power may also result in reduced self-heating of infrared sensor assembly 128.

In accordance with additional embodiments of the present disclosure, various techniques are provided for reducing the effects of noise in image frames provided by infrared imaging devices operating at low voltages. In this regard, when infrared sensor assembly 128 is operated with low voltages as described, noise, self-heating, and/or other phenomena may, if uncorrected, become more pronounced in image frames provided by infrared sensor assembly 128.

For example, referring to FIG. 13, when LDO 1220 maintains Vload at a low voltage in the manner described herein, Vbolo will also be maintained at its corresponding low voltage and the relative size of its output signals may be reduced. As a result, noise, self-heating, and/or other phenomena may have a greater effect on the smaller output signals read out from infrared sensors 132, resulting in variations (e.g., errors) in the output signals. If uncorrected, these variations may be exhibited as noise in the image frames. Moreover, although low voltage operation may reduce the overall amount of certain phenomena (e.g., self-heating), the smaller output signals may permit the remaining error sources (e.g., residual self-heating) to have a disproportionate effect on the output signals during low voltage operation.

To compensate for such phenomena, infrared sensor assembly 128, infrared imaging module 100, and/or host device 102 may be implemented with various array sizes, frame rates, and/or frame averaging techniques. For example, as discussed, a variety of different array sizes are contemplated for infrared sensors 132. In some embodiments, infrared sensors 132 may be implemented with array sizes ranging from 32 by 32 to 160 by 120 infrared sensors 132. Other example array sizes include 80 by 64, 80 by 60, 64 by 64, and 64 by 32. Any desired array size may be used.

Advantageously, when implemented with such relatively small array sizes, infrared sensor assembly 128 may provide image frames at relatively high frame rates without requiring significant changes to ROIC and related circuitry. For example, in some embodiments, frame rates may range from approximately 120 Hz to approximately 480 Hz.

In some embodiments, the array size and the frame rate may be scaled relative to each other (e.g., in an inversely proportional manner or otherwise) such that larger arrays are implemented with lower frame rates, and smaller arrays are implemented with higher frame rates. For example, in one embodiment, an array of 160 by 120 may provide a frame rate of approximately 120 Hz. In another embodiment, an array of 80 by 60 may provide a correspondingly higher frame rate of approximately 240 Hz. Other frame rates are also contemplated.

By scaling the array size and the frame rate relative to each other, the particular readout timing of rows and/or columns of the FPA array may remain consistent, regardless of the actual FPA array size or frame rate. In one embodiment, the readout timing may be approximately 63 microseconds per row or column.

As previously discussed with regard to FIG. 8, the image frames captured by infrared sensors 132 may be provided to a frame averager 804 that integrates multiple image frames to provide image frames 802 (e.g., processed image frames) with a lower frame rate (e.g., approximately 30 Hz, approximately 60 Hz, or other frame rates) and with an improved signal to noise ratio. In particular, by averaging the high frame rate image frames provided by a relatively small FPA array, image noise attributable to low voltage operation may be effectively averaged out and/or substantially reduced in image frames 802. Accordingly, infrared sensor assembly 128 may be operated at relatively low voltages provided by LDO 1220 as discussed without experiencing additional noise and related side effects in the resulting image frames 802 after processing by frame averager 804.

Other embodiments are also contemplated. For example, although a single array of infrared sensors 132 is illustrated, it is contemplated that multiple such arrays may be used together to provide higher resolution image frames (e.g., a scene may be imaged across multiple such arrays). Such arrays may be provided in multiple infrared sensor assemblies 128 and/or provided in the same infrared sensor assembly 128. Each such array may be operated at low voltages as described, and also may be provided with associated ROIC circuitry such that each array may still be operated at a relatively high frame rate. The high frame rate image frames provided by such arrays may be averaged by shared or dedicated frame averagers 804 to reduce and/or eliminate noise associated with low voltage operation. As a result, high resolution infrared images may be obtained while still operating at low voltages.

In various embodiments, infrared sensor assembly 128 may be implemented with appropriate dimensions to permit infrared imaging module 100 to be used with a small form factor socket 104, such as a socket used for mobile devices. For example, in some embodiments, infrared sensor assembly 128 may be implemented with a chip size in a range of approximately 4.0 mm by approximately 4.0 mm to approximately 5.5 mm by approximately 5.5 mm (e.g., approximately 4.0 mm by approximately 5.5 mm in one example). Infrared sensor assembly 128 may be implemented with such sizes or other appropriate sizes to permit use with socket 104 implemented with various sizes such as: 8.5 mm by 8.5 mm, 8.5 mm by 5.9 mm, 6.0 mm by 6.0 mm, 5.5 mm by 5.5 mm, 4.5 mm by 4.5 mm, and/or other socket sizes such as, for example, those identified in Table 1 of U.S. Provisional Patent Application No. 61/495,873 previously referenced herein.

One or more embodiments of the disclosure are directed to a measurement device that may be conveniently carried by electricians or other users to work sites, and utilized by such users in performing measurements and inspections in an integrated manner without requiring users to use multiple different devices. For example, electricians or other users working on an electrical installation job may use one or more embodiments of the measurement device to precisely measure various distances or spans of electrical wire installation locations to determine the length of wires required, inspect a wire spool to check whether there is a wire long enough remaining on the spool, and check the length of cut wires before installing them at the installation locations. After installing the wires and/or other electrical components, users may also use the measurement device to check various electrical parameters associated with the wires and/or other electrical components to detect and/or diagnose electrical faults. In addition, electricians or other users may utilize the measurement device to view a thermal image of a scene to conveniently locate and/or identify potential electrical faults, for example.

Figure 14A:
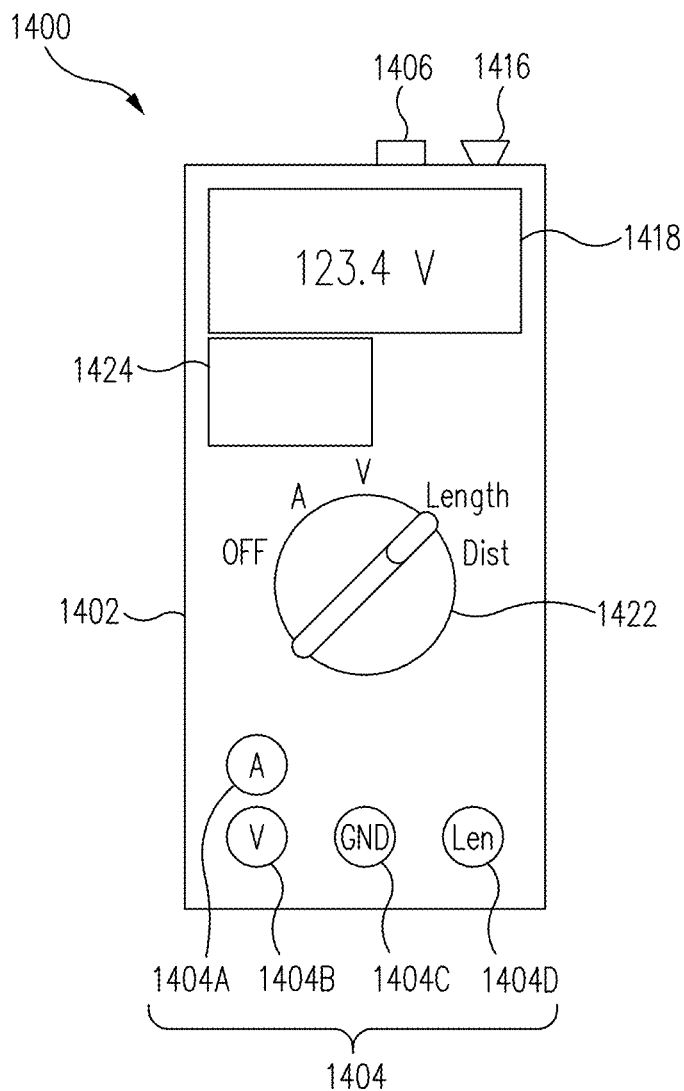
FIG. 14A illustrates a front exterior view of a measurement device in accordance with an embodiment of the disclosure.
Figure 14B:
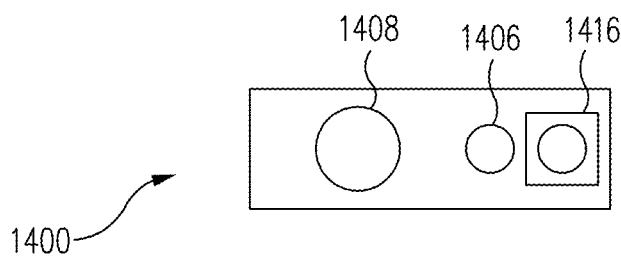
FIG. 14B illustrates a top exterior view of the measurement device of FIG. 14A, in accordance with an embodiment of the disclosure.
Figure 15:
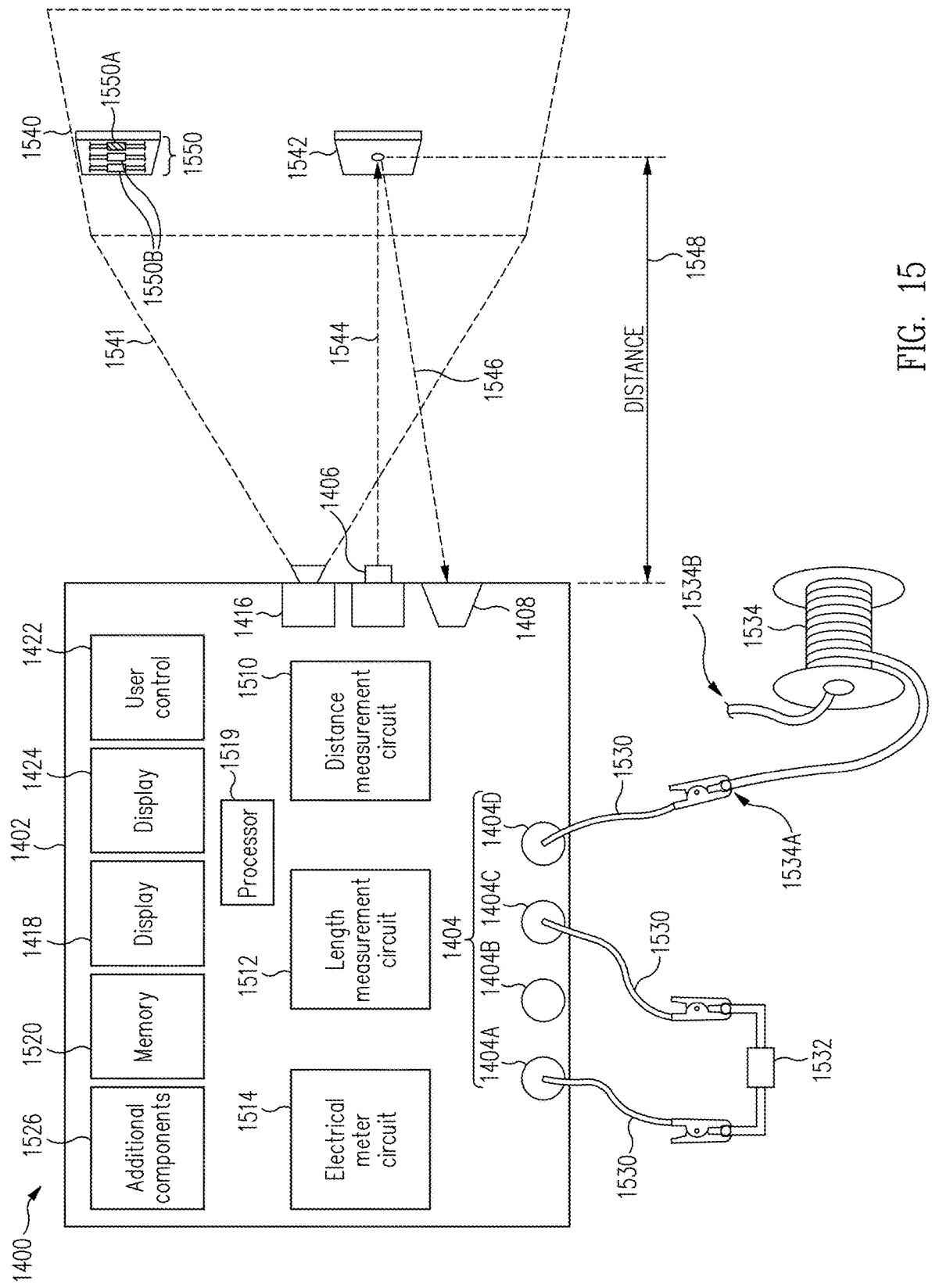
FIG. 15 illustrates a block diagram of the measurement device of FIG. 14A, in accordance with an embodiment of the disclosure.

Turning to FIGS. 14A-15, a measurement device 1400 (e.g., a measuring apparatus, meter, or instrument) according to various embodiments of the disclosure will now be described. For example, measurement device 1400 may be used by electricians and other persons to perform various tasks while working in the field. Such tasks may include, for example, installing electrical systems, inspecting electrical systems, and/or other tasks in performing a series of electrical measurement, installation, and inspection tasks. One or more embodiments of measurement device 1400 may beneficially aid such electricians and other persons by providing, in a convenient form factor, various integrated and cooperative measurement and inspection capabilities such as distance measurement, wire length measurement, electrical parameter measurement, and/or thermal imaging capabilities.

FIGS. 14A-14B illustrate various exterior views of measurement device 1400 in accordance with embodiments of the disclosure. More specifically, FIG. 14A shows a front side view and FIG. 14B shows a top side view, respectively, of measurement device 1400. Various components of measurement device 1400 may be disposed in (e.g., completely enclosed within, substantially enclosed within, and/or partially enclosed within) and/or otherwise disposed on a housing 1402. Housing 1402 may be adapted to be handheld or otherwise conveniently handled by a user (e.g., an electrician) when being carried or used, such as during field operation. As shown, housing 1402 in one embodiment may be of a size and shape generally similar to a conventional multimeter typically carried to a work site by an electrician. In another embodiment, housing 1402 may include a handle or other protrusion (e.g., a pistol grip) that permits a user to comfortably hold housing 1402. It should be noted, however, that housing 1402 may in general be of any size and/or shape adapted for comfortable field use, and need not be limited to shapes that permit one-hand use.

In one embodiment, measurement device 1400 may include, disposed in or on housing 1402, a plurality of electrical terminals 1404 (e.g., including one or more electrical terminals identified as 1404A-1404D), an optical emitter 1406, a sensor 1408, an infrared imaging module 1416, a display 1418, a user control 1422, and/or a display 1424. The locations of the various components illustrated in FIGS. 14A-14B are provided only for purposes of exposition, and the various components identified herein may be disposed in or on any other location on housing 1402 as desired or suitable for particular applications of measurement device 1400. For example, in other embodiments, all or some of the plurality of terminals 1404 may be disposed on a side or bottom surface of housing 1404 if such locations are more convenient in the use and/or manufacture of measurement device 1400. It will also be appreciated that one or more components of measurement device 1400 may be combined with each other and/or omitted as desired depending on particular applications of measurement device 1400, without departing from the scope and spirit of the disclosure.

Referring now to FIG. 15, a block diagram of measurement device 1400 is illustrated in accordance with an embodiment of the disclosure. Measurement device 1400 may include a distance measurement circuit 1510, a length measurement circuit 1512, an electrical meter circuit 1514, a memory 1520, and/or additional components 1526. Distance measurement circuit 1510, length measurement circuit 1512, and electrical meter circuit 1514 may be implemented with any appropriate combination of analog and/or digital circuits configured to perform various operations described herein.

In one embodiment, various measurement operations may be performed by analog circuits. In another embodiment, some operations may be performed by analog circuits, with analog signals being converted to digital signals (e.g., using analog-to-digital converters (DACs) or other sampling techniques) for further processing by digital circuits. In yet another embodiment, output from digital circuits may be converted back to analog signals (e.g., using digital-to-analog converters or DACs) for yet further processing.

In some embodiments, digital circuit portions of distance measurement circuit 1510, length measurement circuit 1512, or electrical meter circuit 1514 may be implemented as application-specific integrated circuits (ASICs) specifically configured to perform measurement operations described herein with high performance and/or high efficiency. In other embodiments, digital circuit portions may be implemented with a general purpose central processing unit (CPU), a microcontroller, a digital signal processing (DSP) device, or other processor, which may be configured to execute appropriate software instructions to perform various operations described herein.

In some embodiments, distance measurement circuit 1510, length measurement circuit 1512, and electrical meter circuit 1514 may be implemented in a single chip, module, packaging, or circuit board, and/or may share some common subcomponents. For example, distance measurement circuit 1510, length measurement circuit 1512, and electrical meter circuit 1514 may all be provided in a single chip, and share common subcomponents such as ADCs, DACs, or I/O logic. In another example, a single general purpose processor may be utilized to implement digital circuit portions of all three components, and may be configured to selectively execute three different software modules each configured to cause the processor to perform appropriate processing for corresponding measurement operations. In other embodiments, at least one of distance measurement circuit 1510, length measurement circuit 1512, and electrical meter circuit 1514 may be implemented in a chip, module, or packaging that is separate from the others.

Distance measurement circuit 1510 may be communicatively coupled (e.g., connected via appropriate circuit board traces, buses, wires, cables, ribbon connectors, and/or other connections suitable for transmitting analog and/or digital signals) to optical emitter 1406 and sensor 1408. Distance measurement circuit 1510 may be configured to determine a distance 1548 from measurement device 1400 to a target 1542 by transmitting an optical beam using optical emitter 1406 and detecting, using sensor 1408, the optical beam reflected by target 1542. For example, FIG. 15 shows a path 1544 that may be taken by the transmitted optical beam to target 1542 and a path 1546 that may be taken by the reflected optical beam back to sensor 1408. Optical beam may be transmitted as one or more pulses, a continuous beam, a beam that is modulated to encode pulses, and/or other optical transmissions suitable for determining distance 1546 based on the reflected optical beam from the target. In some embodiments, distance 1548 may be determined using a conventional time-of-flight distance calculation technique or phase-shift detection technique. Accordingly, distance measurement circuit 1510 may include any suitable combination of analog and digital circuits, and/or any suitable combination of hardware and software configured to implement appropriate distance calculation techniques. Optical beams may be transmitted periodically or in response to a user input (e.g., when user presses a button on user control 1422).

In one embodiment, optical emitter 1406 may be implemented using a laser (e.g., a laser diode) adapted to operate in response to an appropriate control signal from distance measurement circuit 1510. In this embodiment, sensor 1408 may be implemented using an optical detector that is sensitive to laser light in a band of wavelengths corresponding to that of the laser. In other embodiments, other optical light sources may be used to implement optical emitter 1406, with sensor 1408 being implemented using optical detectors appropriate for the type of optical light source being used. Such optical light sources may include, for example, visible light sources; near, midrange, and/or far infrared light sources; and/or other non-visible light sources. Accordingly, optical emitter 1406 may be implemented using a light emitter that may be appropriate and/or desired for particular applications of measurement device 1400. Non-optical emitters and detectors are also contemplated and within the scope and spirit of the disclosure. For example, instead of an optical emitter and detector, an ultrasound emitter and a corresponding ultrasonic detector, which may be sufficient for short range distance measurement applications, may be utilized for distance measurement.

In one embodiment, optical emitter 1406 may be configured to transmit a continuous optical beam while measurement device 1400 is being used for distance measurement (e.g., put into a distance measurement mode). Such a beam may produce a visible indication of where the optical pulse and/or beam would hit (e.g., a laser dot designating the point of impingement), thereby aiding a user in aiming the optical pulse and/or beam on a desired target. In such an embodiment, the optical beam may be appropriately modulated or otherwise altered to encode optical pulses, amplitude modulations, frequency modulations, or other modulations of the optical beam. In another embodiment, a separate optical emitter may be utilized to provide a visible indication of the point of impingement.

Length measurement circuit 1512 may be electrically coupled (e.g., using circuit board traces, cables, wires, and/or other appropriate electrical paths with sufficient power ratings for desired applications of measurement device 1400) to one or more of terminals 1404, and configured to determine an approximate length of a wire or cable electrically connected thereto via the one or more of terminals 1404. Similarly, electrical meter circuit 1514 may be electrically coupled to one or more of terminals 1404, and configured to determine various electrical parameters (e.g., voltage, current, resistance, capacitance, or other parameters) of an external article (e.g., electrical/electronic devices, components, circuit boards, wires, cables, traces, and/or other electrical/electronic articles) electrically connected thereto via the one or more of terminals 1404.

In this regard, in one or more embodiments terminals 1404 may be adapted to form an electrical connection to external wires, cables, or other articles. For example, in one or more embodiments, terminals 1404 may include appropriate connection mechanisms (e.g., receptacles, sockets, plugs, pins, clips, screws, or other suitable electrical/electronic connectors) for electrically connecting to external wires, cables, or other articles. In one embodiment, terminals 1404 may include suitable connection mechanisms configured to insertably and/or releasably receive appropriate test leads 1530. In some embodiments, test leads 1530 may include a standard plug or other type of connector at one end, and/or a clip (e.g., an alligator clip) or a probe at the other end. Test leads 1530 having a proprietary design are also contemplated.

In one embodiment, each of terminals 1404 may be wired and configured for a specific type of input. For example, terminal 1404A may be used to measure voltage, terminal 1404B may be used to measure current, and terminal 1404D may be used to measure a wire length, with terminal 1404C used to provide a ground connection. In another example, terminals 1404A-1404D may be further differentiated based on voltage ranges, current ranges, resistance ranges, or other measurement ranges. In another embodiment, terminals 1404 may be switchable (e.g., by automatic sensing and/or receiving manual selection to adjust an appropriate switching circuit) to selectably receive different types of inputs. Thus, length measurement circuit 1512 and electrical meter circuit 1514 may be electrically connected to an external article (e.g., external article 1532) or a wire (e.g., wire 1534 on a spool) via one or more terminals 1404. A test lead (e.g., test lead 1530) may be utilized to electrically connect to the external article or wire if desired.

Returning to description of length measurement circuit 1512, a length of a wire (e.g., wire 1534) may be determined, in one embodiment, using a time-domain reflectometry (TDR) technique. More specifically, for example, length measurement circuit 1512 may include an appropriate analog circuit, digital circuit, and/or software module configured to generate and transmit an electrical pulse (e.g., a voltage change having a short rise time) from a connected end 1534A of wire 1534, to receive the pulse reflected back from an open end 1534B of wire 1534, and to determine the length of wire 1534 based on a total propagation time of the pulse. That is, the length may be determined from the time difference between the transmission of the pulse and the receipt of the reflected pulse. Because the propagation speed of an electrical signal is constant for a given type of wire, the length of wire 1534 may be calculated from the time it takes for an electrical signal to travel from connected end 1534A to open end 1534B and back.

In this regard, length measurement circuit 1512 in one embodiment may include a lookup table (e.g., in an appropriate data structure and/or a hardware memory device) associating various standardized wire gauges (e.g., American wire gauge (AWG) standard) with a corresponding propagation speed therethrough. In this embodiment, a user may input or otherwise select (e.g., using user control 1422) a wire gauge value for the wire to be measured. In another embodiment, length measurement circuit 1512 may be configured to derive an appropriate propagation speed to base the length calculation on, by measuring a total propagation time through a wire of a known length. For example, a user may cut a small wire segment of a certain length from a spool of wire to be measured, and connect the segment to measurement device 1400 to allow length measurement circuit 1512 to automatically determine the propagation speed. Such an embodiment may allow a user to measure a length of a wire when the gauge of the wire is not known or when the wire is of a non-standard gauge. In another embodiment, an appropriate propagation speed for determining a length of the wire may be provided by a user (e.g., input using user control 1422), without a need for a lookup table.

In one embodiment, length measurement circuit 1512 may include an appropriate analog circuit, digital circuit, and/or software module configured to determine an approximate length of a wire based on a cumulative resistance through the length of the wire. Because a resistance through a wire is proportional to the length of the wire, an approximate length may be calculated by high-precision measurement of a cumulative resistance through the length of the wire. In this regard, length measurement circuit 1512 in one embodiment may include another lookup table associating various standardized wire gauges with a unit resistance value (e.g., milliohms per feet). In another embodiment, length measurement circuit 1512 may be configured to derive a unit resistance value by measuring the resistance of a wire of a known length supplied by a user. In another embodiment, an appropriate unit resistance value for determining a length of the wire may be provided by a user (e.g., input using user control 1422), without a need for a lookup table.

Electrical meter circuit 1514 may include an appropriate analog circuit, digital circuit, and/or software module to measure various electrical parameters such as voltage, current, resistance, capacitance, and/or other parameters associated with an external article connected thereto. For example, electrical meter circuit 1514 may be configured to generate and transmit through the external article a reference electrical signal (e.g., a reference voltage or a reference current), and to determine an electrical parameter (e.g., a resistance) based on changes observed in the electrical signal (e.g., a voltage drop). In various embodiments, electrical meter circuit 1514 may be configured to determine one or more selected electrical parameters in response to a user selection at user control 1422. In some embodiments, electrical meter circuit 1514 may be configured to provide auto-ranging and/or auto-sensing of electrical parameters.

Display 1418 may be communicatively coupled to distance measurement circuit 1510, length measurement circuit 1512, and electrical meter circuit 1514. Display 1418 may be configured to present, indicate, or otherwise convey information indicative of the distance, the length, and/or the electrical parameters determined by the respective circuits. In this regard, display 1418 may include a display processor configured to convert signals or data from the respective circuits into appropriate forms for presentation. The display processor may be implemented using any appropriate combination of analog circuits, digital circuits, and/or software modules. For example, in some embodiments, a general-purpose microcontroller or a general-purpose processing core may be utilized as the display processor. In other embodiments, dedicated hardware logic or an ASIC may be utilized to implement the display processor. In some embodiments, the display processor may not be implemented as part of display 1418, but rather as part of distance measurement circuit 1510, length measurement circuit 1512, electrical meter circuit 1514, and/or other portions of measurement device 1400.

In some embodiments, the display processor may be implemented as part of a processor 1519 that is utilized to implement various circuits of measurement device 1400. In addition to implementing the display processor, processor 1519 may be adapted to implement processors for distance measurement circuit 1510, length measurement circuit 1512, electrical meter circuit 1514, and/or other portions of measurement device 1400 as desired for particular embodiments.

In various embodiments, display 1418 may be implemented using an alpha-numeric readout panel (e.g., a segmented LED panel, a vacuum fluorescent display (VFD) panel, a liquid crystal display (LCD) panel, or other multi-segment, multi-element, or dot-matrix panels) and/or an electronic display screen (e.g., a cathode ray tube (CRT), a LCD screen, or other types of video displays and monitors). In some embodiments, display 1418 may be configured to display numbers, letters, and/or symbols suitable for presenting the information generated by measurement device 1400. For example, display 1418 may be configured to display the measured distance, length, and/or electrical parameters in numerical digits, with appropriate letters or symbols displayed to indicate the type of information (e.g., whether the numbers indicate a distance, wire length, voltage, current, resistance, or capacitance, or other parameter) and the applicable unit (e.g., meters, inches, feet, volts, amperes, ohms, farads, or other units). In other embodiments, display 1418 may be configured to present, in addition to or instead of a numerical presentation, a graphical presentation of the information generated by measurement device 1400. Such graphical presentation may include, for example, bar graphs, pie graphs, dials, line graphs, images, graphics or other suitable presentation of corresponding measurement values. In yet another example, display 1418 may be implemented using a pointer (e.g., a needle) moving over on a dial calibrated for the various measurements that may be presented. It is also contemplated that combinations of display implementations described above may be utilized for display 1418.

Memory 1520 may include one or more memory devices to store data and information, including the information indicative of the distance measurements, the length measurements, and the electrical parameter measurements determined by the respective circuits. The one or more memory devices may include various types of memory including volatile and non-volatile memory devices, such as RAM (Random Access Memory), flash memory, EEPROM (Electrically-Erasable Read-Only Memory), ROM (Read Only Memory), a hard disk drive, other suitable memory devices. In some embodiments, memory 1520 may be configured to store software instructions that may be accessed and executed by display processors of display 1418/1424, measurement circuit 1510, length measurement circuit 1512, electrical meter circuit 1514, processor 1519, and/or other components of measurement device 1400. In some embodiments, such instructions may also be stored in a computer-readable medium, such as a compact disc, a digital video disc, a flash drive, or other suitable medium, for downloading or otherwise transferring such instructions to measurement device 1400.

In one or more embodiments, measurement device 1600 may include a logic device 1601 which encompasses one or more of electrical meter circuit 1514, processor 1519, memory 1520, and/or additional measurement components 1611. Logic device 1601 may, for example, be used to determine one or more physical parameters associated with an external article (e.g., in response to one or more signals received from sensors and/or other components as appropriate) in accordance with any of the various techniques described herein. In some embodiments, logic device 1601 may be implemented as described herein with regard to processing module 160 and/or processor 195.

In one embodiment, memory 1520 may be implemented as a separate component communicatively coupled to other components of measurement device 1400. In other embodiments, memory 1520 may be implemented as part of (e.g., embedded, distributed throughout, or otherwise implemented) measurement circuit 1510, length measurement circuit 1512, electrical meter circuit 1514, display 1418, processor 1519, and/or other components of measurement device 1400.

In some embodiments, measurement circuit 1510, length measurement circuit 1512, electrical meter circuit 1514, display 1418, and/or other components of measurement device 1400 may be configured to store in memory 1520 the information indicative of the distance measurements, the length measurements, and the electrical parameter measurements determined by the respective circuits. The stored information may be recalled or otherwise accessed by various components of measurement device 1400. For example, in one embodiment, the display processor of display 1418 or processor 1519 may be configured to store in memory 1520 one or more measurement values as determined by the measurement circuits, and to access the previously stored measurement values so that display 1418 may present both current and previous measurements for convenient comparison by a user. In other embodiments, measurement circuit 1510, length measurement circuit 1512, electrical meter circuit 1514, and/or other components of measurement device 1400 may be configured to perform the storing and recalling.

Thus, for example, when an electrician is installing an electrical wire, measurement device 1400 may beneficially allow the electrician to conveniently compare a previously obtained distance measurement of an installation location (e.g., the span or height of the installation location) with a currently measured length of a wire to be used for the location. The electrician may conveniently view the two different measurements on display 1418, for example, to verify whether the wire is long enough for the location without having to separately write down or memorize the span of the location. In some embodiments, one or more previously stored measurements (e.g., distance measurements) may be displayed simultaneously with a currently obtained measurement (e.g., wire length measurements). In other embodiments, a user may be able to switch or flip between (e.g., using a key or button provided by user control 1422) the previous and current measurements to view them in an alternating manner.

In some embodiments, the stored measurements and the currently obtained measurements may be further managed or processed by distance measurement circuit 1510, length measurement circuit 1512, electrical meter circuit 1514, display 1418, and/or other components of measurement device 1400. In one embodiment, the display processor of display 1418 or other components may be configured to obtain an aggregate value of two or more measurements, an average value of two or more measurements, or other derivations from two or more values. Thus, for example, when multiple distance measurements are required for a wire installation location (e.g., when a wire installation has bends and turns rather than a straight-line connection), measurement device 1400 may beneficially provide an electrician with an aggregate span (e.g., a sum of multiple distance measurements) of the installation location so that the electrician does not have to write down and add up multiple measurements to figure out how long a wire is needed.

In another embodiment, the display processor of display 1418 or other components may be configured to compare the previously stored measurements with the currently obtained measurements. An alarm, message, or other notification may optionally be generated based on the comparison. Thus, for example, measurement device 1400 may beneficially perform a comparison of a stored distance measurement and a currently obtained wire length measurement, and provide an electrician with an indication (e.g., through a beep, a flashing light, or other notification tones and/or lights) of whether or not the wire is long enough for the distance. As such, measurement device 1400 may allow the electrician to check whether there is enough wire left on a spool to cover an installation location without having to read and compare measured values on display 1418. In another example situation, measurement device 1400 may indicate whether or not a wire is cut to a correct length by comparing a current measurement of the length of the wire to previously measured distances. As may be appreciated, the comparison operations may be performed on aggregate values or other derived values as well.

Infrared imaging module 1416 may be a small form factor infrared camera or a small form factor infrared imaging device suitable for capturing thermal images. For example, infrared imaging module 1416 may be implemented using infrared imaging module 100 of FIG. 1 or other embodiments disclosed herein with respect to FIGS. 1-13. Infrared imaging module 1416 may include an FPA implemented, for example, in accordance with various embodiments disclosed herein or others where appropriate.

Infrared imaging module 1416 may be configured to capture, process, and/or otherwise manage infrared images (e.g., including thermal images) of a scene (e.g., a scene 1540) associated with an environment of a user. In this regard, infrared imaging module 1416 may be attached, mounted, installed, plugged in or otherwise disposed at any suitable location on or in housing 1402 to allow a desired portion of the user's environment to be placed within a field of view (FOV) 1541 of infrared imaging module 1416 when the user points measurement device 1400 generally toward the desired portion of the user's environment. Also, as discussed above in connection with infrared imaging module 100 of FIG. 1, infrared imaging module 1416 and/or associated components may be configured to perform various NUC processes described herein.

The captured thermal images of the scene may be presented as user-viewable thermal images (e.g., thermograms) for viewing by the user. In one embodiment, display 1418 (e.g., implemented using an electronic display screen) may be configured to display the user-viewable thermal images. In another embodiment, measurement device 1400 may include another display 1424 fixed relative to the housing (e.g., attached thereto, disposed therein, disposed thereon, and/or otherwise fixed) and configured to display the user-viewable thermal images. Display 1424 may be implemented with an electronic display screen, such as a LCD, a LED, a cathode ray tube (CRT), or other types of generally known electronic displays suitable for showing images and/or videos. Although two displays 1418 and 1424 are shown in the example of FIGS. 14 and 15, it is contemplated that any number of such displays 1418/1424 may be included in measurement device 1400 depending on desired applications of measurement device 1400.

According to various embodiments, infrared imaging module 1416, processor 1519, and/or display 1418/1424 may be configured to perform suitable conversion operations to generate the user-viewable thermal images from the thermal images captured at an FPA of infrared imaging module. For example, the temperature data contained in the pixels of the thermal images may be converted into appropriate gray-scaled or color-scaled pixels to construct images that can be viewed by a person. In some embodiments, the user-viewable images may optionally include a temperature scale or legend that indicates the approximate temperature of corresponding pixel color and/or intensity.

By viewing such user-viewable thermal images, a user may be able to perform various electrical inspections. For example, user-viewable thermal images may quickly reveal hot spots 1550A and/or cold spots 1550B in electrical installations 1550, which may indicate failures such as poor connections, corroded connections, incorrectly secured connections, internal damage, unbalanced loads, and other various electrical faults. In another example, cold spots 1550B may indicate moisture, which may be a cause for electrical failure. Thus, for example, using infrared imaging module 1416 of measurement device 1400, an electrician working at an electrical installation location may quickly scan the installation location after measuring and installing (e.g., utilizing measurement device 1400 as described above) electrical wires and components to inspect for any fault in the installation. It should be appreciated that the thermal images captured and presented by measurement device 1400 may also be utilized for various other purposes, such as inspecting and detecting water and gas leaks and other applications of thermal imaging.

In some embodiments, the user-viewable thermal images may provide visual guidance for aiming the optical beam transmitted from optical emitter 1406 to measure distances. For example, in one embodiment, infrared imaging module 1416 may be positioned and oriented relative to optical emitter 1406 such that the optical beam reflected off target 1542 may be placed within FOV 1541 of infrared imaging module 1416. Further, in this embodiment, infrared imaging module 1416 may be configured to be sensitive to IR radiation generated by the optical beam. Alternatively, optical emitter 1406 may be configured to generate an optical beam in IR wavelengths which infrared imaging module 1416 may be sensitive to. In either implementation, infrared imaging module 1416 may capture thermal images that include images of the reflected optical beam. Thus, by conveniently viewing the user-viewable images, a user may be able to aim the optical beam from optical emitter 1406 toward a desired spot or target for distance measurement.

In another embodiment, infrared imaging module 1416, display 1418/1424, and/or processor 1519 may be configured to overlay onto the user-viewable thermal images a reticle, a crosshair, or other mark suitable for indicating the impingement point of the optical beam from optical emitter 1406. Such a reticle or crosshair on the user-viewable screens may provide an additional or alternative visual guidance in aiming the optical beam for distance measurement. User control 1422 may include one or more rotary knobs, buttons, keypads, sliders, and/or other user-activated mechanisms configured to interface with a user and receive user input. For example, FIG. 14A shows one embodiment having user control 1422 implemented at least in part using a rotary knob. In some embodiments, user control 1422 may be implemented as part of display 1418 or display 1424 configured to function as both a user input device and a display device. For example, user control 1422 may be implemented as a graphical user interface (GUI) presented on display 1418 (e.g., a touch screen).

In various embodiments, user control 1422 may receive a user selection of an operating mode for measurement device 1400, such as a distance measurement mode, a wire length measurement mode, or an electrical meter mode provided by the respective circuits as described above. In various embodiments, user control 1422 may further receive various types of user input described above in connection with various components of measurement device 1400, such input including a selection of electrical parameter type to be measured (e.g., a voltage, a current, a resistance, a capacitance, or other parameter that may be determined by electrical meter circuit 1514), a selection of a wire gauge number, a reference propagation speed of a wire, a unit resistance value of a wire, a trigger for distance measurement, a control input for thermal imaging, and/or other inputs as desired for particular applications of measurement device 1400.

Additional components 1526 may include any other device or component as may be desired for various applications of measurement device 1400. In some embodiments, additional components 1526 may include motion sensors implemented in the same or similar manner as described with regard to motion sensors 194 in FIG. 1. Such motion sensors may be monitored by and provide information to infrared imaging module 1416 and/or other relevant components to perform various NUC techniques described herein.

In some embodiments, additional components 1526 may include a positioning component such as a global positioning system (GPS) module adapted to generate geopositional information. The geopositional information obtained through the GPS module may be utilized to annotate the obtained measurement information and/or thermal images with the location of the associated electrical inspection or installation site, for example.

In some embodiments, additional components 1526 may include one or more sensors that may be utilized to detect one or more physical parameters associated with electrical inspection or installation sites. For example, in one embodiment, additional components 1526 may include a moisture sensor (e.g., digital hygrometer) that can measure humidity or moisture level and convert the measured humidity into suitable signals that may be further processed by processor 1519 and/or other suitable components of measurement device 1400. Similarly, the motion sensor, GPS module, and other sensors described herein for measurement device 1400 may generate suitable sensor signals indicative of the sensed physical parameters. The sensor signals may be received and further processed by logic device 1601 of measurement device, according to some embodiments of the disclosure.

In some embodiments, additional components 1526 may include an indicator light (e.g., an LED indicator, a colored light bulb, or other conventional light sources used to implement indicators), a beeper, a chime, a speaker with associated circuitry for generating a tone, or other appropriate devices that may be used to generate an audible and/or visible notification. Such audible and/or visible indicators may be utilized to inform a user as to a result of measurement or a test, for example, whether or not a wire is long enough for an installation location as described above with respect to display 1418 and memory 1520.

In some embodiments, additional components 1526 may include a visible light camera implemented with a charge-coupled device (CCD) sensor, a complementary metal-oxide semiconductor (CMOS) sensor, an electron multiplying CCD (EMCCD), a scientific CMOS (sCMOS) sensor and/or other appropriate image sensor to capture visible light images of the scene. Depending on the sensor type, visible light camera may be adapted to capture electromagnetic radiation in other wavelengths in addition to or instead of visible light. For example, in some embodiments, the visible light camera may be adapted to capture images of near infrared (NIR) and/or short-wave infrared (SWIR) radiation from the electrical installation or inspection site (e.g., scene 1540). NIR and SWIR are generally referred to as non-thermal infrared. In contrast, some implementations of infrared imaging module 1416 are adapted to capture MWIR and/or LWIR images (i.e., thermal IR images) as discussed above in connection with infrared sensors 132. Thus, for some embodiments, images of visible light, NIR, and/or SWIR radiation captured by the visible light camera may be used to complement MWIR and/or LWIR images captured by infrared imaging module 1416 as further described herein.

In one embodiment, the visible light camera may be co-located with infrared imaging module 1416 to form a dual-camera module. In one example, infrared imaging module 1416 and the visible light camera may be implemented as a dual sensor module sharing a common substrate according to various techniques described in U.S. Provisional Patent Application No. 61/748,018 previously referenced herein. Such a dual sensor module implementation may include common circuitry and/or common restraint devices for infrared imaging and visible light imaging, thereby potentially reducing an overall size of measurement device 1400 as compared to embodiments where infrared imaging module 1416 and the visible light camera are implemented as individual modules. Additionally, the dual sensor module implementation may be adapted to reduce a parallax error between images captured by infrared imaging module 1416 and the visible light camera by spacing them closer together.

In another embodiment, the visible light camera may be attached, mounted, installed, plugged in or otherwise disposed at a suitable location separate from infrared imaging module 1416. In some embodiments, visible light images captured by the visible light camera may be fused, superimposed, or otherwise combined with the thermal images captured by infrared imaging module 1416 to generate user-viewable thermal images with higher definition, clarity, and/or contrast using appropriate techniques as further described herein with reference to FIG. 19 and elsewhere.

In some embodiments, measurement device 1400 described above may be conveniently carried by electricians or other users to work sites, and utilized by such users to perform various measurements and inspections in an integrated manner without requiring users to use multiple different devices or write down intermediate measurements. Further, the thermal images captured and presented by measurement device 1400 may advantageously aid users in quickly scanning the work site for electrical and other faults, as well as in accurately and conveniently aiming optical beams to perform distance measurement.

Figure 16:
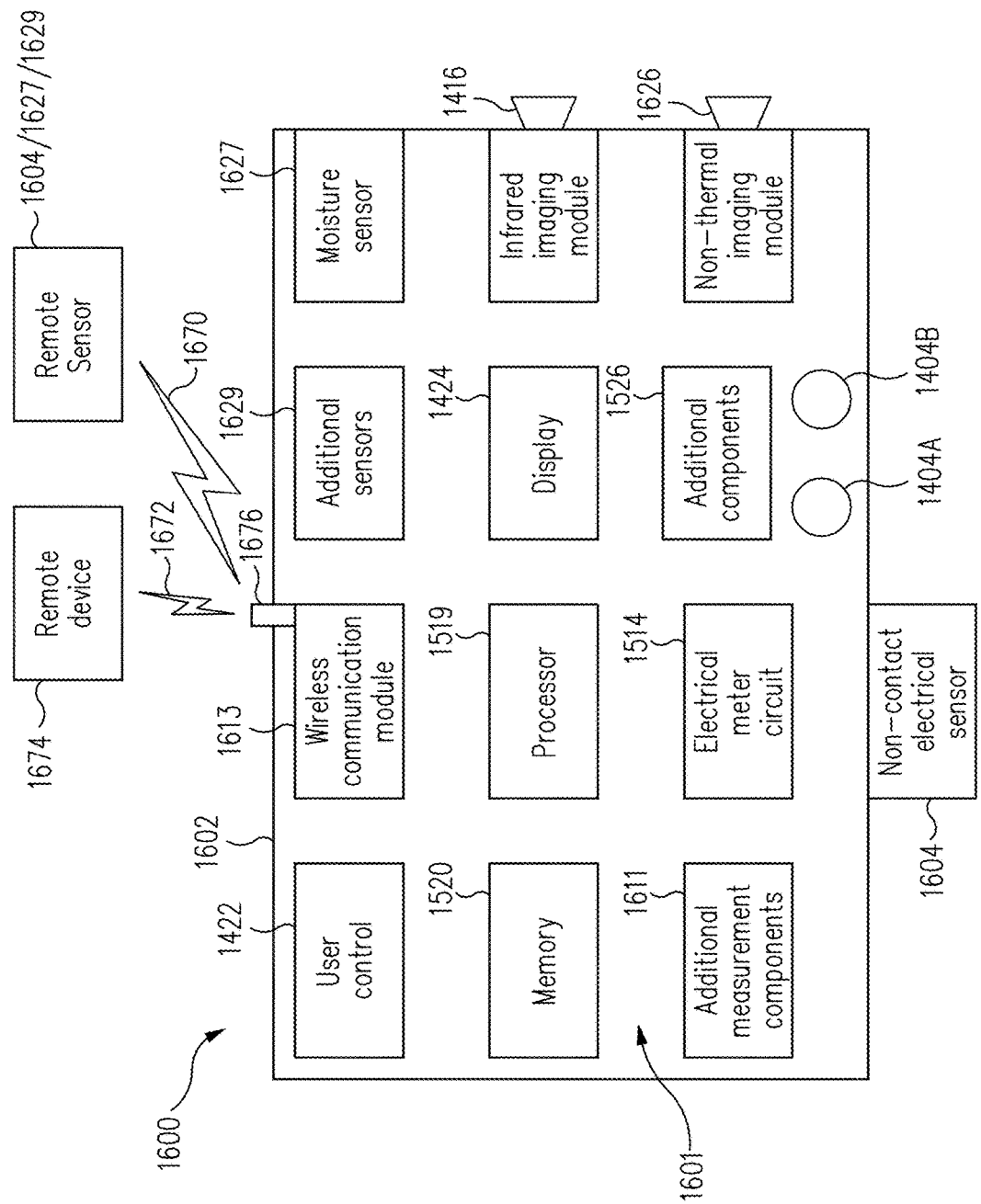
FIG. 16 illustrates a block diagram of a measurement device in accordance with another embodiment of the disclosure.

FIG. 16 illustrates a block diagram of another embodiment of a measurement device 1600. As shown, measurement device 1600 may include various components described above for measurement device 1400 and denoted by like reference numerals. Measurement device 1600 may also include a housing 1602, a non-contact electrical sensor 1604, additional measurement components 1611, a wireless communication module 1613, a non-thermal imaging module 1626, a moisture sensor 1627, and/or additional sensors 1629.

Non-contact electrical sensor 1604 may be adapted to sense electrical current, voltage, and/or other electrical parameters associated with a conductor without making a physical electrical contact with the conductor. For example, non-contact electrical sensor 1604 may be implemented with an inductive sensor comprising a Rogowski coil, an iron (or ferrite) core current transformer, or other appropriate transducer capable of sense AC current. In some embodiments, non-contact electrical sensor 1604 may comprise a Hall effect sensor that allows both AC and DC sensing. In some embodiments, non-contact electrical sensor 1604 may comprise a coil or transducer configured for sensing voltage associated the conductor via a capacitive coupling technique known in the art. Thus, non-contact electrical sensor 1604 may be provided in addition to or instead of electrical terminals 1404, to sense electrical parameters without a need for electrical terminals 1404 and test leads 1530. For embodiments having non-contact electrical sensor 1604, processor 1519 and/or electrical meter circuit 1514 may be adapted to convert the parameters sensed via non-contact electrical sensor 1604 into appropriate measurement values.

In some embodiments, non-contact electrical sensor 1604 may be provided in a clamp that can be opened and closed by a user of measurement device 1600, so that the conductor can be at least partially encircled by the clamp for measuring. In some embodiments, non-contact electrical sensor 1604 may be provided in a flexible loop having at least one end that is detachable to allow the loop to encircle the conductor to be measured. It is also contemplated that non-contact electrical sensor 1604 may be provided in other forms and/or structures suitable for non-contact sensing of various electrical parameters associated with the conductor.

In some embodiments, the clamp, flexible loop, or other structure comprising the non-contact electrical sensor 1604 may be detachable or separate from housing 1602. Non-contact electrical sensor 1604 for such embodiments may be placed at a distance from a user holding housing 1602 that contains other components of measurement device 1600, thereby permitting the user to remain at a safe stand-off distance while obtaining electrical measurements from potentially dangerous components. In such embodiments, the clamp, flexible loop, or other structure comprising the non-contact electrical sensor 1604 may be further adapted to wirelessly transmit sensed or measured electrical parameters to other components (e.g., processor 1519) of measurement device 1600 for further processing and/or displaying to the user.

It is contemplated that other components of measurement device 1600 may also be configured to allow remote measurement in a similar manner. For example, moisture sensor 1627 and its supporting circuitry if any may be provided in their own housing that is detachable or separate from housing 1602, and configured to wirelessly transmit sensed or measured moisture level. In another example, all or part of electrical meter circuit 1514 and electrical terminals 1404 may be provided in their own housing detachable or separate from housing 1602, and configured to wirelessly transmit sensed or measured electrical parameters associated with a component electrically connected to terminals 1404 via test leads 1530.

In this regard, measurement device 1600 in some embodiments may include wireless communication module 1613 adapted to handle, manage, or otherwise facilitate wireless communication (e.g., via wireless link 1670) between such detachable or separate sensors and other components of measurement device 1600. For example, wireless communication module may include components to implement the IEEE 802.11 WiFi standards, the Bluetooth™ standard, the ZigBee™ standard, or other appropriate short range wireless communication standards. Wireless communication module 1613 may also be configured for a proprietary wireless communication protocol and interface based on radio frequency (RF), microwave frequency (MWF), infrared frequency (IRF), and/or other appropriate wireless transmission technologies. Wireless communication module 1613 may include an antenna 1676 coupled thereto for wireless communication purposes.

In some embodiments, wireless communication module 1613 may be adapted to handle, manage, or otherwise facilitate wireless communication (e.g., via wireless link 1672) between measurement device 1600 and a remote device 1674. Remote device 1674 may represent, for example, a workstation computer, a server computer, a tablet computer, a laptop computer, a smartphone, another measurement device 1600, or any other suitable device with wireless communication and data processing capabilities. In such embodiments, one or more components (e.g., processor 1519 and/or electric meter circuit 1514) of measurement device 1600 may be adapted to wirelessly transmit measurement information, thermal images, non-thermal images, and/or other data (e.g., time and location, user notes, or other annotations) generated by measurement device 1600 via wireless communication module 1613 to remote device 1674, where such measurement information, images, and/or other data may be further processed and/or stored.

Additional measurement components 1611 may represent optical emitter 1406, sensor 1408, distance measurement circuit 1510, and/or length measurement circuit 1512 described above with reference to FIGS. 14 and 15. In various embodiments, one or more of additional measurement components 1611 may optionally be provided in measurement device 1600.

Non-thermal imaging module 1626 may be implemented in a same or similar manner as the visible light camera of measurement device 1400 described above for additional components 1526 of measurement device 1400. As such, non-thermal imaging module 1626 may be adapted to capture visible light, NIR, and/or SWIR images that may be fused, superimposed, or otherwise combined with the thermal images captured by infrared imaging module 1416 to generate user-viewable thermal images with higher definition, clarity, and/or contrast using appropriate techniques as further describe herein with reference to FIG. 19 and elsewhere.

Moisture sensor 1627 may be provided in some embodiments, and implemented in a same or similar manner as the moisture sensor of measurement device 1400 described above for additional components 1526 of measurement device 1400. Humidity or moisture level measurement obtained with moisture sensor 1627 may be used to verify presence of water or moisture in various spots of electrical installation or inspection sites. As discussed above with respect to cold spots 1550B in FIG. 15, a user of measurement device 1600 may scan electrical installation or inspection sites to locate cold spots, and then verify presence of water or moisture in the located cold spots from moisture level measurements obtained via moisture sensor 1627. As also discussed above, moisture sensor 1627 according to some embodiments may be adapted to wirelessly transmit sensed data to permit remote measurement of moisture levels.

Additional sensors 1629 represent one or more other types of sensor that may be optionally provided in measurement device 1600. Additional sensors 1629 may include, for example, an acoustic sensor adapted to detect sound (e.g., sounds from electric arcing) and/or locate sound. In other examples, additional sensors 1629 may include a vibration sensor and/or a temperature sensor. As discussed above with reference to additional components 1526 of FIG. 15, sensor signals generated by moisture sensor 1627 and additional sensors 1429 may be received and further processed by logic device 1601 of measurement device, according to some embodiments of the disclosure.

As described with reference to FIG. 15, display 1424 may be adapted to display user-viewable thermal images from thermal images captured by infrared imaging module 1416 and/or from images generated by combining the thermal images with non-thermal images captured by non-thermal imaging module 1626. In some embodiments, display 1424 may be further adapted to display numbers, letters, and/or symbols suitable for presenting the information generated by measurement device 1600.

For example, processor 1519 and/or display 1424 may be adapted to generate for display the measured distance, length, and/or electrical parameters in numerical digits, with appropriate letters or symbols displayed to indicate the type of information (e.g., whether the numbers indicate a distance, wire length, voltage, current, resistance, or capacitance, or other parameter) and the applicable unit (e.g., meters, inches, feet, volts, amperes, ohms, farads, or other units). For further example, processor 1519 and/or display 1424 may be configured to generate for display, in addition to or instead of a numerical presentation, a graphical presentation of the information generated by measurement device 1600. Such graphical presentation may include, for example, bar graphs, pie graphs, dials, line graphs, images, graphics or other suitable presentation of corresponding measurement values. In such embodiments, processor 1519 and/or display 1424 may be adapted to overlay the generated letters, numbers, symbols, graphics, and/or other representation of measurement information onto the user-viewable thermal images when the user-viewable thermal images are also displayed on display 1424.

Figure 17:
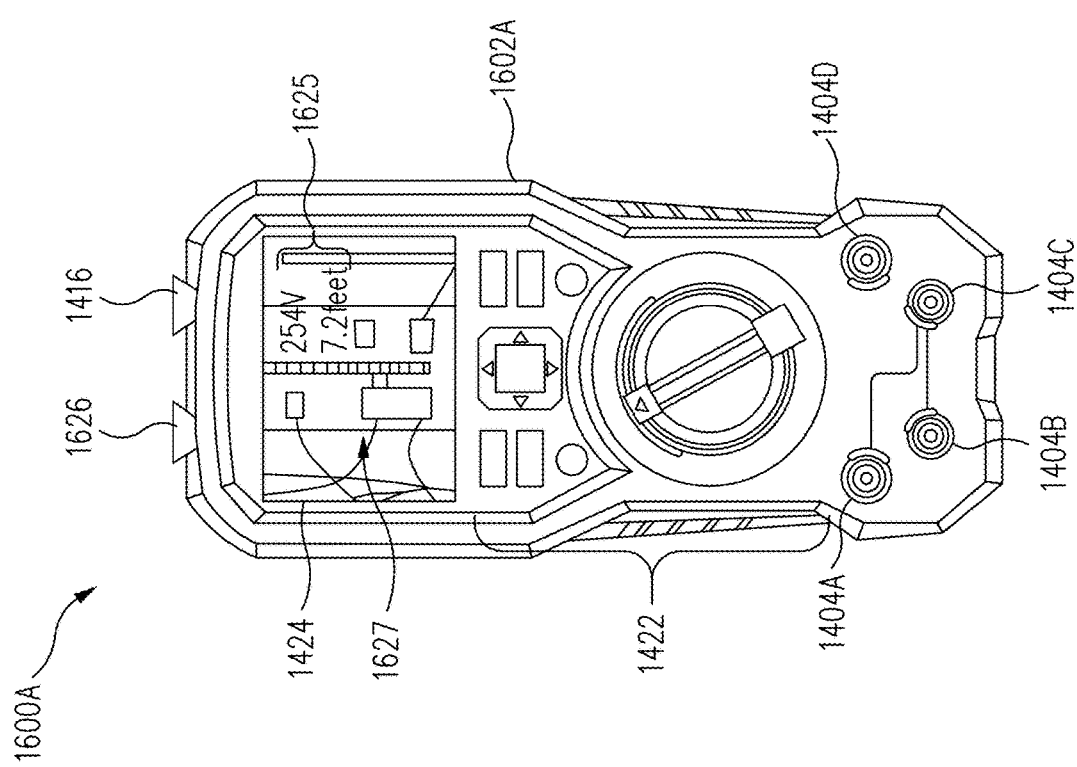
FIG. 17 illustrates a front exterior view of a measurement device in accordance with an embodiment of the disclosure.

Turning to FIG. 17, a front exterior view is illustrated of a measurement device 1600A implemented in accordance with an embodiment of measurement device 1600 of FIG. 16. Measurement device 1600A may include display 1424, where letters, numbers, symbols, graphics, and/or other representation of measurement information may be displayed and/or overlaid user-viewable thermal images as discussed above. In the example illustration of FIG. 17, display 1424 is showing measurement information 1625 overlaid onto a user-viewable thermal image 1637. In another aspect, measurement device 1600A may include both infrared imaging module 1416 and non-thermal imaging module 1626. As such, various components of measurement device 1600A may be configured to generate enhanced user-viewable thermal images for display by combining thermal and non-thermal images as further described herein.

Figure 18:
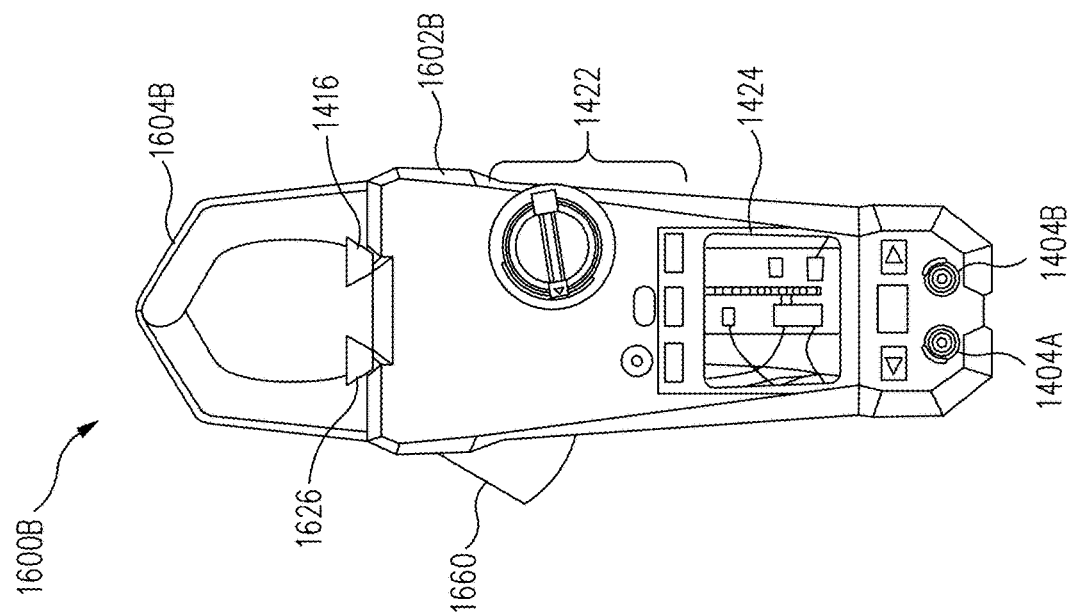
FIG. 18 illustrates a front exterior view of a measurement device in accordance with another embodiment of the disclosure.

FIG. 18 illustrates a front exterior view of a measurement device 1600B implemented in accordance with another embodiment of measurement device 1600 of FIG. 16. As shown, measurement device 1600B may include a clamp 1604B implementing non-contact electrical sensor 1604. As described above for non-contact electrical sensor 1604, clamp 1604B may be opened by a user of measurement device 1600B to at least partially encircle electrical components (e.g., a conducting wire) for measuring electrical parameters. Measurement device 1600B may include a lever 1660 adapted to open clamp 1604B when pushed down by a user (e.g., by a lever action). A motorized actuator, pneumatic actuator, hydraulic actuator, and other suitable means for opening clamp 1604 are also contemplated for other embodiments.

Figure 19:
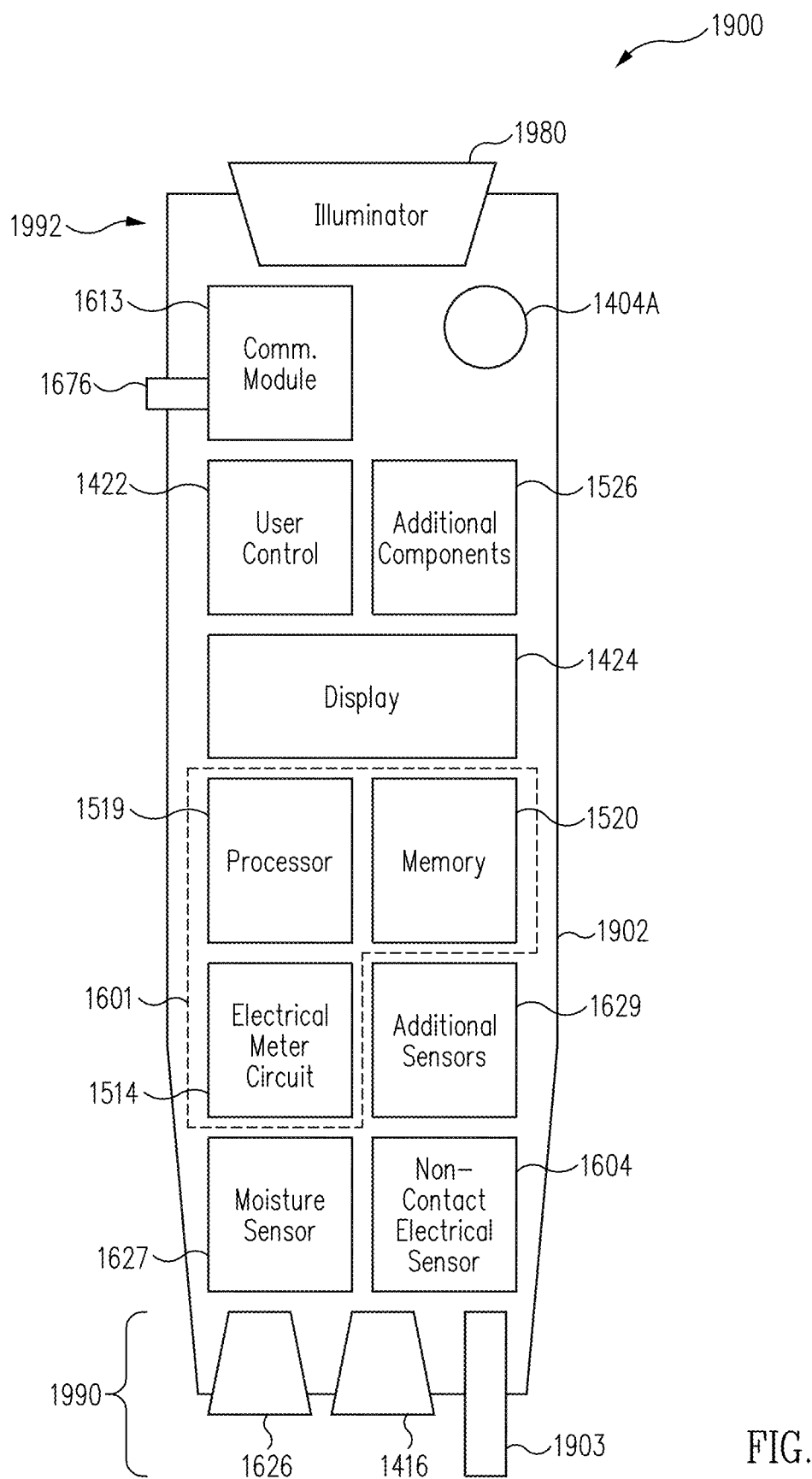
FIG. 19 illustrates a block diagram of a measurement device in accordance with another embodiment of the disclosure.

Turning to FIG. 19, a block diagram is illustrated of yet another embodiment of a measurement device 1900. Measurement device 1900 may include various components that may be implemented in a same or similar manner (e.g., with appropriate modifications for particular embodiments of device 1900) as corresponding components described for measurement device 1400/1600 and denoted by like reference numerals. For example, in various embodiments, measurement device 1900 may include infrared imaging module 1416, non-thermal imaging module 1626, display 1424, processor 1519, memory 1520, electrical meter circuit 1514, non-contact electrical sensor 1604, moisture sensor 1627, additional sensors 1629, wireless communication module 1613, electrical terminal 1404A, user control 1422, and/or additional components 1526, which may be modified for embodiments of measurement device 1900 where applicable.

Measurement device 1900 according to various embodiments may comprise an elongated housing 1902 having a proximal end 1990 and a distal end 1992. Elongated housing 1902 may also have a relatively compact dimension compared with housing 1402 or 1602 of measurement device 1400 or 1600, thereby permitting measurement device 1900 to be packaged in a compact form factor for improved portability. Such a form factor may be referred to as a "pen-type," "tester pen," or "test pen" form factor, which allows for convenient carrying by a user, for example in a pocket of the user's clothing. In one or more embodiments, elongated housing 1902 may taper toward proximal end 1990, so that it may be easier for a user to grip by wrapping fingers around.

Measurement device 1900 may comprise a probe tip 1903 provided on and/or partially embedded in (e.g., integrated into) proximal end 1990 of elongated housing 1902. In some embodiments, probe tip 1903 may comprise electrically conductive material and may be electrically connected to non-contact electrical sensor 1604 and/or electrical meter circuit 1514 to facilitate measurement and/or detection of electrical properties via non-contact electrical sensor 1604 and/or electrical meter circuit 1514. In some embodiments, both probe tip 1903 and a test lead (e.g., test lead 1530) plugged into electrical terminal 1404A may be used to contact an external article to form a circuit for measurement of electrical properties. In some embodiments, probe tip 1903 may be retractably provided, so that probe tip 1903 may at least partially be retracted into housing 1902, for example, to protect it from damage when it does not need to protrude from housing 1902 (e.g., when performing non-contact measurement, when measurement device 1900 is not in use, or in other situations). In such embodiments, a slider, a screw, or other appropriate mechanical actuator connected to probe tip 1903 may be provided to allow a user to selectively retract or extend probe tip 1903.

In some embodiments, probe tip 1903 may additionally or alternatively be electrically connected to moisture sensor 1627 to facilitate measurement and/or detection of moisture. For embodiments that measure moisture associated with a surface based on resistivity changes, probe tip 1903 may comprise a plurality of pins to make contact with the surface. For embodiments that measure moisture based on an electrical field, probe tip 1903 may not need a plurality of such contact pins but instead comprise a larger surface area (e.g., in the shape of a pad, a sphere, or other sizes and forms). In some embodiments, contact pins or pads for moisture measurement may be provided in a separate hand-held probe (not shown in FIG. 19) that may be plugged into measurement device 1900 (e.g., plugged into terminal 1404A).

As described above, non-contact electrical sensor 1604 may be adapted to sense electrical current, voltage, and/or other electrical parameters associated with a conductor without making a physical electrical contact with the conductor. For example, in one or more embodiments of measurement device 1900, non-contact electrical sensor 1604 may be configured to detect presence of voltage and/or current via capacitive coupling, inductive coupling, magnetic field, and/or other appropriate techniques based on electrical or magnetic field sensing. In some embodiments, non-contact electrical sensor 1604 may be configured to measure a magnitude or sense an approximate magnitude of voltage and/or current associate with a conductor without making a physical electrical contact. In some embodiments, non-contact electrical sensor 1604 may comprise appropriate analog and/or digital components configured to convert the detected presence and/or magnitude of voltage and/or current into a signal format suitable for processing by processor 1519. In other embodiments, non-contact electrical sensor 1604 may comprise appropriate analog and/or digital components configured to signal the detected presence and/or magnitude of voltage and/or current via an indicator light, a beeper, a chime, a speaker, a vibrator, or other appropriate device described in connection with additional components 1526.

For one or more embodiments of measurement device 1900, electrical meter circuit 1514 may be configured to measure and/or detect various electrical parameters such as voltage, current, resistance, capacitance, and/or other parameters associated with an external article connected thereto via probe tip 1903 and/or a test lead plugged into electrical terminal 1404A. For example, electrical meter circuit 1514 may be configured to detect a presence of voltage or current via probe tip 1903 as a single contact point with an external article or circuit. In other examples, electrical meter circuit 1514 may be configured to utilize both probe tip 1903 and electrical terminal 1404A as two terminals for measuring various electrical parameters in a manner similar to measurement device 1400 described above.

As briefly described above, moisture sensor 1627 for measurement device 1900 according to some embodiments may be based on a resistive-type moisture sensor known in the art, and configured to measure and/or detect moisture by sensing changes in resistance between two or more contact pins of probe tip 1903 contacting a surface. In other embodiments, moisture sensor 1627 may be configured to measure and/or detect moisture by sensing changes in an electric field generated by moisture sensor 1627 via probe tip 1903, based on known techniques in the art.

Similar to measurement devices 1400 and 1600, measurement device 1900 may provide on display 1426 user-viewable thermal images of a scene (e.g., an electrical work site) captured by infrared imaging module 1416. As described herein, in some embodiments processor 1519 may be configured to combine thermal images captured by infrared imaging module 1416 with non-thermal images captured by non-thermal imaging module 1626 to provide user-viewable thermal images having improved contrast, details, clarity, and/or resolution. User-viewable thermal images may be generated in various ways as described above for measurement devices 1400 and 1600. In some embodiments, thermal images captured by infrared imaging module 1416 may be further processed by processor 1519 to provide information relating to moisture content, humidity, or dampness associated with a surface in a scene captured in the thermal images. In such embodiments, processor 1519 may be configured to process the captured thermal images to determine moisture content, humidity, or dampness associated with a surface based on suitable techniques known in the art, for example according to various techniques described in U.S. Pat. No. 7,237,946 entitled "Use of IR Camera" and incorporated herein by reference.

In various embodiments, measurement device 1900 may include an illuminator 1980 implemented using a light source such as an LED, incandescent light bulb, high intensity discharge (HID) lamp, or other suitable light source. In some embodiments, illuminator 1980 may be provided on distal end 1992 of housing 1902. However, embodiments comprising illuminator 1980 that may additionally or alternatively be provided on proximal end 1990 or other portions of housing 1902 are also contemplated. Thus, for example, a user may utilize measurement device 1900 as a flashlight to illuminate a component or work site while obtaining a measurement of an associated physical parameter or for other purposes, without having to carry a separate flashlight to the work site or hold a separate flashlight while performing a measurement.

Measurement device 1900 according to some embodiments may include additional sensors 1629 for measuring and/or detecting various physical parameters other than those obtained using non-contact electrical sensor 1604, electrical meter circuit 1514, and/or moisture sensor 1627. As discussed above with reference to measurement device 1600, such additional sensors 1629 may include, for example, an acoustic sensor, a light sensor, a vibration sensor and/or a temperature sensor. One or more of such additional sensors may be utilized, for example, to detect and/or locate a presence of live electricity (e.g., by detecting and/or locating sound and light from electrical arcing).

Figure 20:
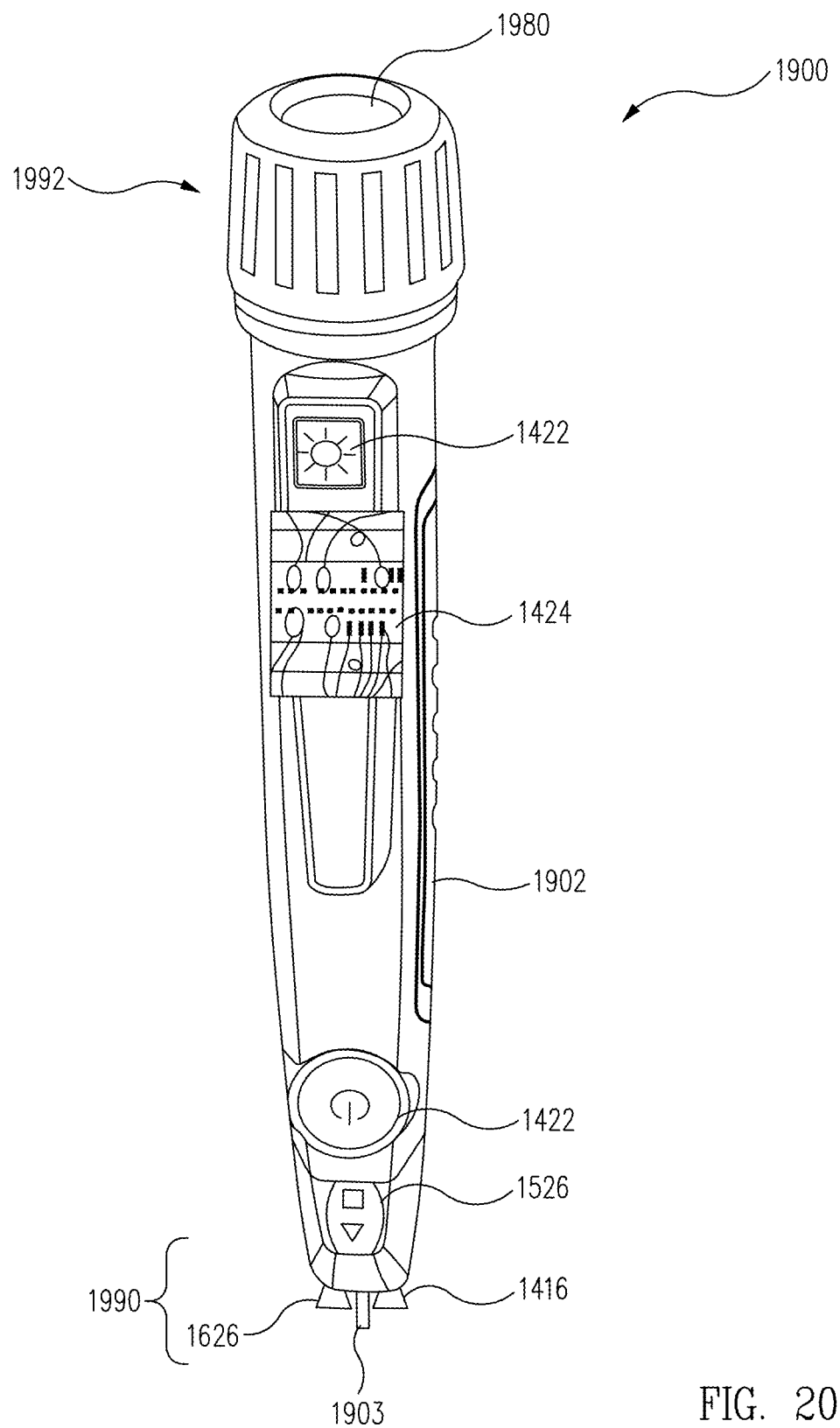
FIG. 20 illustrates a front exterior view of a measurement device in accordance with another embodiment of the disclosure.

FIG. 20 shows a front exterior view of one or more embodiments of measurement device 1900. In the example shown in FIG. 20, probe tip 1903, infrared imaging module 1416, and non-thermal imaging module 1626 may be found at or near proximal end 1990 of housing 1902, whereas illuminator 1980 is provided on distal end 1992. Display 1424 and one or more switches and/or buttons implementing user control 1422 may be provided on an exterior surface of housing 1902. In the illustrated example of FIG. 20, display 1424 is implemented using a small form factor color screen (e.g., based on TFT-LCD, LED, or other suitable technology) to provide user-viewable thermal images in color according to a color palette, as would be understood by one skilled in the art. In other examples, display 1424 may be a monochromatic display (e.g., a black-and-white display) to provide user-viewable thermal images according to a monochromatic palette (e.g., a gray scale palette mapping the intensity of thermal radiation into luminance of displayed pixels).

In some embodiments, measurement device 1900 may include additional components 1526 to convey detected and/or measured physical parameters to a user. In the example shown in FIG. 20, additional components 1526 representing one or more indicator lights are provided on an exterior surface of housing 1902 to indicate a presence and/or magnitude of a physical parameter. According to one non-limiting example, non-contact electrical sensor 1604 and/or other logic device 1601 of measurement device 1900 may be configured to turn on an indicator light if a voltage above a certain threshold is detected. According to another non-limiting example, non-contact electrical sensor 1604 and/or other logic device 1601 of measurement device 1900 may be configured to vary the intensity (e.g., brightness) of an indicator light in response to the detected magnitude of a voltage. As discussed above, additional components 1526 in various embodiments may include a bell, chime, speaker, vibrator, and/or other appropriate component to generate a sound and/or vibration to indicate a presence and/or magnitude of a physical parameter, in addition to or in place of one or more indicator lights.

Various embodiments of measurement device 1900 described above with reference to FIGS. 19 and 20 may therefore provide thermal imaging capabilities and various physical parameter detection and/or measurement capabilities integrated in a highly portable pen-type or tester pen form factor. As such, measurement device 1900 may allow for convenient carrying by a user and for quick inspection of electrical faults, water damage, gas leaks, or other problems through thermal imaging and physical parameter measurement in an integrated manner.

Figure 21:
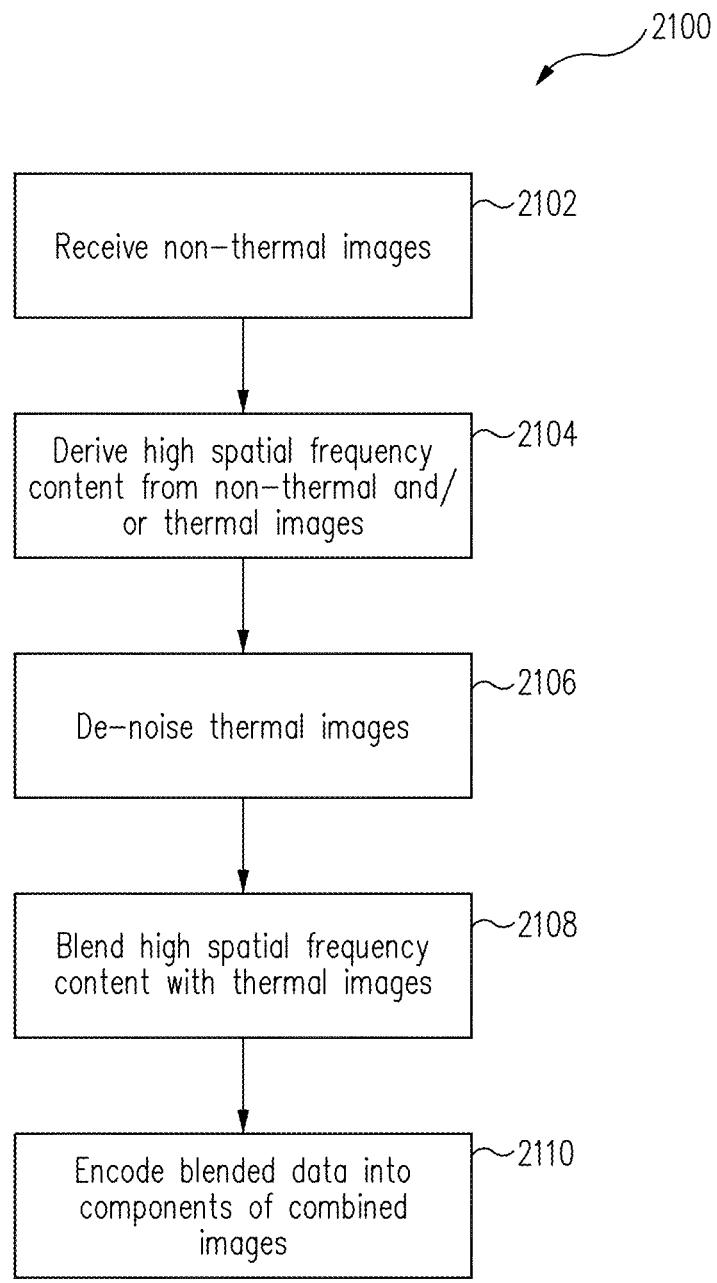
FIG. 21 illustrates a flowchart of a process to combine thermal images and non-thermal images in accordance with an embodiment of the disclosure.

Referring now to FIG. 21, a flowchart of a process 2100 to combine or fuse thermal images and non-thermal (e.g., visible light) images is illustrated in accordance with an embodiment of the disclosure. The combined images may include radiometric data and/or other thermal characteristics corresponding to radiation from electrical inspection or installation sites (e.g., scene 1540), but with significantly more object detail (e.g., contour or edge detail) and/or contrast than typically provided by the thermal or non-thermal images alone. Thus, for example, the combined images generated in these examples may beneficially provide sufficient radiometric data, detail, and contrast to allow easier recognition and/or interpretation of various electrical components (e.g., wires, circuit breakers, or other electrical components at inspection or installation sites) and potential faults associated with them.

Although the process described herein in connection with FIG. 21 discusses fusing or combining thermal images with visible light images as an example, it should be appreciated that the process may be applied to combining thermal images with any suitable non-thermal images (e.g., visible light images, near infrared images, short-wave infrared images, EMCCD images, ICCD images, or other non-thermal images captured by non-thermal imaging module 1626). Process 2100 may be performed by various components of measurement device 1400, 1600, or 1900, for example by processor 1519, display 1424, infrared imaging module 1416, and/or non-thermal imaging module 1626.

At block 2102, visible light images and infrared images such as thermal images may be received. For example, visible light images of scene 1540 may be captured by non-thermal imaging module 1626 and the captured visible light images may be received by processor 1519. For example, thermal images of scene 1540 may be captured by infrared imaging module 1416 and the captured thermal images may be received by processor 1519. Processor 1519 may perform various operations of process 2100 using both thermal images and non-thermal images, for example.

At block 2104, high spatial frequency content from one or more of the visible light and thermal images may be derived from one or more of the visible light and thermal images received in block 2102. High spatial frequency content derived according to various embodiments may include edge/contour details and/or high contrast pixels extracted from the one or more of the visible light and thermal images, for example.

In one embodiment, high spatial frequency content may be derived from the received images by performing a high pass filter (e.g., a spatial filter) operation on the images, where the result of the high pass filter operation is the high spatial frequency content. In an alternative embodiment, high spatial frequency content may be derived from the received images by performing a low pass filter operation on the images, and then subtracting the result from the original images to get the remaining content, which is the high spatial frequency content. In another embodiment, high spatial frequency content may be derived from a selection of images through difference imaging, for example, where one image is subtracted from a second image that is perturbed from the first image in some fashion, and the result of the subtraction is the high spatial frequency content. For example, optical elements of infrared imaging module 1416 and/or optical elements of non-thermal imaging module 1626 may be configured to introduce vibration, de-focusing, and/or movement artifacts into a series of images captured by one or both of infrared imaging module 1416 and non-thermal imaging module 1626. High spatial frequency content may be derived from subtractions of images such as adjacent images in the series.

In some embodiments, high spatial frequency content may be derived from only the visible light images or the thermal images. In other embodiments, high spatial frequency content may be derived from only a single visible light or thermal image. In further embodiments, high spatial frequency content may be derived from one or more components of the visible light and/or thermal mages, such as a luminance component of visible light images, for example, or a radiometric component of thermal images. Resulting high spatial frequency content may be stored temporarily (e.g., in memory 1520) and/or may be further processed according to block 2108.

At block 2106, one or more thermal images may be de-noised. For example, processor 1519 may be configured to de-noise, smooth, or blur one or more thermal images of scene 1540 using a variety of image processing operations. In one embodiment, removing high spatial frequency noise from the thermal images allows the processed thermal images to be combined with high spatial frequency content derived according to block 2104 with significantly less risk of introducing double edges (e.g., edge noise) to objects depicted in combined images of scene 1540.

In one embodiment, removing noise from the thermal mages may include performing a low pass filter (e.g., a spatial and/or temporal filter) operation on the images, where the result of the low pass filter operation is de-noised or processed thermal images. In a further embodiment, removing noise from one or more thermal images may include down-sampling the thermal images and then up-sampling the images back to the original resolution.

In another embodiment, processed thermal images may be derived by actively blurring thermal images of scene 1540. For example, optical elements of infrared imaging module 1416 may be configured to slightly de-focus one or more thermal images captured by infrared imaging module 1416. The resulting intentionally blurred thermal images may be sufficiently de-noised or blurred so as to reduce or eliminate a risk of introducing double edges into combined images of scene 1540, as further described below. In other embodiments, blurring or smoothing image processing operations may be performed by processor 1519 on the received thermal images as an alternative or supplement to using optical elements to actively blur thermal images of scene 1540. Resulting processed thermal images may be stored temporarily (e.g., in memory 1520) and/or may be further processed according to block 2108.

At block 2108, high spatial frequency content may be blended with one or more thermal images. For example, processor 1519 may be configured to blend high spatial frequency content derived in block 2104 with one or more thermal images of scene 1540, such as the processed thermal images provided in block 2106.

In one embodiment, high spatial frequency content may be blended with thermal images by superimposing the high spatial frequency content onto the thermal images, where the high spatial frequency content replaces or overwrites those portions of the thermal images corresponding to where the high spatial frequency content exists. For example, the high spatial frequency content may include edges of objects depicted in images of scene 1540, but may not exist within the interior of such objects. In such embodiments, blended image data may simply include the high spatial frequency content, which may subsequently be encoded into one or more components of combined images, as described in block 2110.

For example, a radiometric component of thermal images may be a chrominance component of the thermal images, and the high spatial frequency content may be derived from the luminance and/or chrominance components of visible light images. In this embodiment, combined images may include the radiometric component (e.g., the chrominance component of the thermal images) encoded into a chrominance component of the combined images and the high spatial frequency content directly encoded (e.g., as blended image data but with no thermal image contribution) into a luminance component of the combined images. By doing so, a radiometric calibration of the radiometric component of the thermal images may be retained. In similar embodiments, blended image data may include the high spatial frequency content added to a luminance component of the thermal images, and the resulting blended data encoded into a luminance component of resulting combined images.

In other embodiments, high spatial frequency content may be derived from one or more particular components of one or a series of visible light and/or thermal images, and the high spatial frequency content may be encoded into corresponding one or more components of combined images. For example, the high spatial frequency content may be derived from a luminance component of visible spectrum images, and the high spatial frequency content, which in this embodiment is all luminance image data, may be encoded into a luminance component of combined images.

In another embodiment, high spatial frequency content may be blended with thermal images using a blending parameter and an arithmetic equation. For example, in one embodiment, the high spatial frequency content may be derived from a luminance component of visible light images. In such an embodiment, the high spatial frequency content may be blended with a corresponding luminance component of thermal image according to a blending parameter and a blending equation to produce blended image data. The blended image data may be encoded into a luminance component of combined images, for example, and the chrominance component of the thermal images may be encoded into the chrominance component of the combined images. In embodiments where the radiometric component of the infrared images may be their chrominance component, the combined images may retain a radiometric calibration of the thermal images. In other embodiments, portions of the radiometric component may be blended with the high spatial frequency content and then encoded into combined images.

More generally, the high spatial frequency content may be derived from one or more components of visible light images and/or thermal image. In such an embodiment, the high spatial frequency content may be blended with one or more components of the thermal images to produce blended image data (e.g., using a blending parameter and a blending equation), and resulting combined images may include the blended image data encoded into corresponding one or more components of the combined images. In some embodiments, the one or more components of the blended data do not have to correspond to the eventual one or more components of the combined images (e.g., a color space/format conversion may be performed as part of an encoding process).

A blending parameter value may be selected by a user or may be automatically determined by processor 1519 according to context or other data, for example, or according to an image enhancement level expected by measurement device 1400/1600/1900. In some embodiments, the blending parameter may be adjusted or refined while combined images are being displayed (e.g., by display 1424). In some embodiments, a blending parameter may be selected such that blended image data includes only thermal characteristics, or, alternatively, only visible light characteristics. A blending parameter may also be limited in range, for example, so as not to produce blended data that is out-of-bounds with respect to a dynamic range of a particular color space/format or a display.

In addition to or as an alternative to the processing described above, processing according to the high contrast mode may include one or more processing steps, ordering of processing steps, arithmetic combinations, and/or adjustments to blending parameters as disclosed in U.S. patent application Ser. No. 13/437,645 previously referenced herein. For example, the following equations may be used to determine the components Y, Cr and Cb for the combined images with the Y component from the high pass filtered visible light images and the Cr and Cb components from the thermal images.

hp_y_vis=highpass(y_vis)

(y_ir, cr_ir, cb_ir)=colored(lowpass(ir_signal_linear))

In the above equations, highpass(y_vis) may be high spatial frequency content derived from high pass filtering a luminance component of visible light images.

Colored(lowpass(ir_signal_linear)) may be the resulting luminance and chrominance components of the thermal images after the thermal images are low pass filtered. In some embodiments, the thermal images may include a luminance component that is selected to be 0.5 times a maximum luminance (e.g., of a display and/or a processing step). In related embodiments, the radiometric component of the thermal images may be the chrominance component of the thermal images. In some embodiments, the y_ir component of the thermal images may be dropped and the components of the combined images may be (hp_vis, cr_ir, cb_ir), using the notation above.

In another embodiment, the following equations may be used to determine the components Y, Cr and Cb for combined images with the Y component from the high pass filtered visible light images and the Cr and Cb components from the thermal images.

comb_y=y_ir+alpha×hp_y_vis
comb_cr=cr_ir
comb_cb=cb_ir

The variation of alpha thus gives the user an opportunity to decide how much contrast is needed in the combined images. With an alpha of close to zero, the thermal images alone will be shown, but with a very high alpha, very sharp contours/edges can be seen in the combined images. Theoretically, alpha can be an infinitely large number, but in practice a limitation will probably be necessary, to limit the size of alpha that can be chosen to what will be convenient in the current application.

Once the high spatial frequency content is blended with one or more thermal images, processing may proceed to block 1610, where blended data may be encoded into components of the combined images in order to form the combined images.

At block 2110, the blended data may be encoded into one or more components of the combined images. For example, processor 1519 may be configured to encode blended data derived or produced in accordance with block 2110 into combined images that increases, refines, or otherwise enhances the information conveyed by either the visible light or thermal images viewed by themselves. In some embodiments, encoding blended image data into a component of combined images may include additional image processing operations, for example, such as dynamic range adjustment, normalization, gain and offset operations, noise reduction, and color space conversions, for instance.

In addition, processor 1519 may be configured to encode other image data into combined images. For example, if blended image data is encoded into a luminance component of combined images, a chrominance component of either visible light images or thermal images may be encoded into a chrominance component of combined images. Selection of source images may be made through user input, for example, or may be determined automatically based on context or other data. More generally, in some embodiments, a component of combined images that is not encoded with blended data may be encoded with a corresponding component of visible light images or thermal images. By doing so, a radiometric calibration of thermal images and/or a color space calibration of visible light images may be retained in the resulting combined images.

In some embodiments, at least some part or some functionalities of processor 1519 described herein may be implemented as part of infrared imaging modules 1416, for example, at processing module 160 described above in connection with FIG. 3. In some embodiments, at least some part or some functionalities of processor 1519 may be part of or implemented with processing components of display 1418 and/or display 1424.

Figure 22:
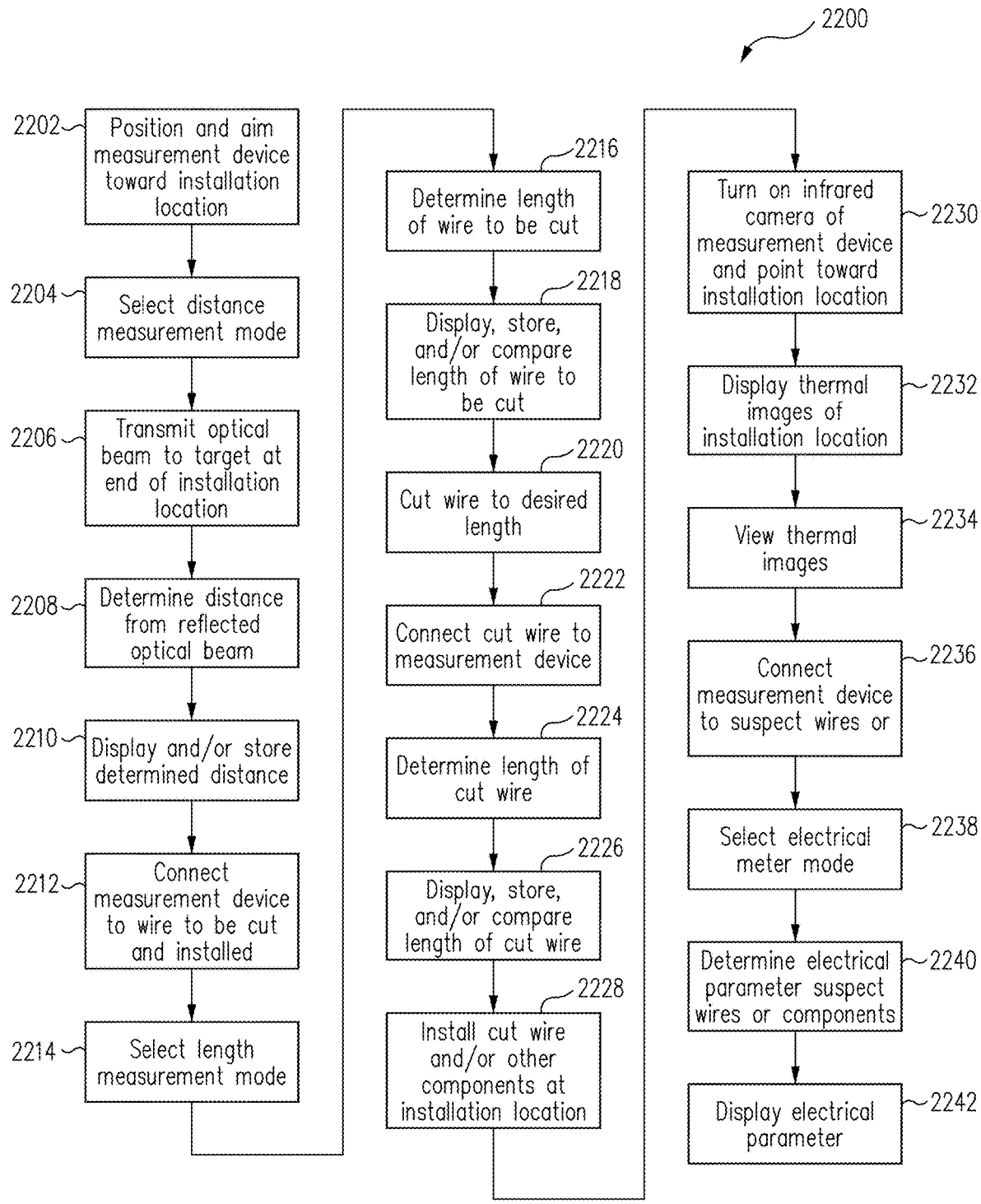
FIG. 22 illustrates a flowchart of a process to perform measurements and inspections using a measurement device in accordance with an embodiment of the disclosure.

Referring now to FIG. 22, a flowchart of a process 2200 to perform measurements and inspections using a measurement device is illustrated in accordance with an embodiment of the disclosure. For example, process 2200 may be performed by in part by various embodiments of measurement device 1400 and in part by a user utilizing various embodiments of measurement device 1400. Although certain portions of process 2200 are described below with respect to measuring, installing, and inspecting operations in electrical wire installation tasks, it should be noted that various operations of process 2200 may be reordered, omitted, and/or combined to perform other tasks as well.

At block 2202, measurement device 1400 is suitably positioned and aimed to measure a distance associated with an installation location. For example, a user may position (e.g., while held by a hand of the user) measurement device 1400 at one end of an installation location and aim optical emitter 1406 toward the other end of the installation location so that the distance between the two ends may be measured. In one embodiment, thermal images including visual guidance information may be captured and generated by performing operations described above with respect to infrared imaging module 1416. In such an embodiment, a user may view user-viewable thermal images, which may include an aiming reticle/cross-hair and/or an image of a reflected optical beam, to accurately aim the optical beam from optical emitter 1406 to the other end of the installation location.

At block 2204, a distance measurement mode is selected as an operating mode of measurement device 1400. For example, the user may input or otherwise provide a selection of a distance measurement mode on user control 1422 of measurement device 1400. Appropriate components of measurement device 1400 may determine a distance as described for blocks 2206-2208 below. Selection of a distance measurement mode may be performed prior to performing operations of block 2202, as needed or desired for particular applications of process 2200.

At block 2206, an optical beam may be transmitted to and reflected from the other end of the installation location. For example, if aimed correctly at block 2202, distance measurement circuit may transmit an optical beam to the other end of the installation location using optical emitter 1406. As described above, the optical beam may be transmitted in various forms, patterns and/or wavelengths. If there is no suitable surface or target from which the optical beam may reflect off at the other end of the installation location, a suitable target object (e.g., any object that sufficiently reflects the optical beam) may be placed at the other end of the installation location by the user.

At block 2208, the distance between the two ends of the installation location may be determined based on the reflected optical beam. For example, based on a detection signal generated by sensor 1408, distance measurement circuit 1510 may determine the distance by performing a time-of-flight distance calculation or phase-shift detection operation as described above with respect to optical emitter 1406, sensor 1408, and distance measurement circuit 1510. The determined distance may then be displayed and/or stored at block 2210. For example, the determined distance may be presented on display 1418 or display 1424 for viewing by the user. In some embodiments, the determined distance may be stored in memory 1520 for displaying and/or further processing as described above in connection with display 1418 and memory 1520. In some embodiments, blocks 2202, 2206, 2208, and 2210 may be repeated to obtain an aggregate span of the installation location, for example, when there are bends and turns in the installation location. As described above, various components of measurement device 1400 may calculate a sum of multiple measurements to provide an aggregate span.

At block 2212, a wire to be cut and installed at the installation location may be connected to measurement device 1400 to determine the length of the wire. For example, the user may connect one or both ends of wire 1534 to appropriate ones of terminals 1404 to electrically connect wire 1534 to length measurement circuit 1512. As discussed, some implementations of length measurement circuit 1512 may operate using electrical connections to both ends 1534A and 1534B of wire 1534, whereas other implementations may operate using only one electrical connection to end 1534A of wire 1534. Wire 1534 may be connected to the appropriate ones of terminals 1404 with or without test leads 1530 as desired.

At block 2214, a length measurement mode is selected as the operating mode of measurement device 1400. For example, the user may input or otherwise provide a selection of a length measurement mode on user control 1422 of measurement device 1400. In some embodiments, a wire gauge number or a propagation speed of the wire to be cut may be input, for example, via user control 1422. Alternatively, a wire segment of a known length may be connected to the measurement device to obtain an appropriate propagation speed on which to base the wire length calculation as described in connection with length measurement circuit 1512.

At block 2216, the length of the wire may be determined. For example, in one embodiment, the length of the wire may be determined using a TDR technique as described above with respect to length measurement circuit 1512. That is, at block 2216, an electrical pulse may be transmitted through wire 1534 via connected end 1534A, and then the electrical pulse reflected at unconnected end 1534B may be detected to determine the length of the wire. In another embodiment, the length of the wire may be determined by measuring a cumulative resistance through wire 1534 with high precision, as also described above with respect to length measurement circuit 1512.

The determined length of the wire to be cut may then be displayed, stored, and/or compared at block 2210. For example, the determined length may be presented on display 1418 or display 1424 for viewing by the user. For example, the determined length may be stored in memory 1520 for displaying and/or further processing as described above in connection with display 1418 and memory 1520. In one embodiment, the user may compare the determined length of the wire with the determined span of the installation location to verify whether the wire is long enough to be cut and installed at the location. In another embodiment, various components of measurement device 1400 may perform the comparison and generate an indication (e.g., using a beep and/or a light) as to whether the wire is long enough, as described above with respect to memory 1520 and display 1418 of measurement device 1400.

If the wire is long enough for the location, the user may cut the wire to the desired length, at block 2220. If not, the user may repeat blocks 2212, 2216, and 2218 with other wires. Once a wire that is long enough for the location is found and cut to the desired length, the length of the cut wire may be verified by connecting the cut wire to the measurement device at block 2222, determining the length of the cut wire at block 2224, and displaying, storing, and/or comparing the length of the cut wire at block 2226. Blocks 2222-2226 may be performed in a similar manner as blocks 2212, 2216, and 2218, except that blocks 2222-2226 may be performed with the cut wire, and the comparison performed by the user or measurement device 1400 may be to verify that the wire is cut to a correct length (e.g., within a certain range relative to the correct length) rather than simply check whether the wire is long enough for the installation location.

At block 2228, the cut wire and/or other electrical components may be installed at the installation location. For example, the user may, after verifying that the wire is cut to a correct length at block 2228, install the cut wire along with other electrical components such as switches, fuses, circuit breakers, distributors, and/or other components if desired. Blocks 2202-2228 may be repeated to perform as many wiring tasks as needed.

After the installation of one or more cut wires and/or other components, an infrared camera of measurement device 1400 (e.g., infrared imaging module 1416) may be turned on and pointed toward the installation location to scan for any abnormal condition, at block 2230. For example, if infrared imaging module 1416 is not already turned on for other purposes (e.g., to aim the optical beam at block 2202), the user may turn on or otherwise activate infrared imaging module 1416 via user control 1422 and point measurement device 1400 toward the installation location so that at least a portion of the installation location is within scene 1540 captured by infrared imaging module 1416. The user may point, position, and/or orient measurement device 1400 to capture any other scene associated with the user's environment if desired.

At block 2232, thermal images of the installation location or other scenes associated with the user's environment may be captured, converted into user-viewable thermal images, and presented for viewing by the user. Capturing of the thermal images, as well as generating and displaying of the user-viewable thermal images, may be performed using techniques described above for infrared imaging module 1416. For example, the user-viewable thermal images may be presented on display 1418 or display 1424 of measurement device 1400 for viewing by the user, after being converted from the thermal images captured by infrared imaging module 1416. If the measurement device includes a visible light camera, visible light images of the installation location or other scenes may be captured, and suitable operations may be performed on the thermal images and the visible light images to generate combined or fused user-viewable thermal images having a higher definition and/or clarity. Suitable operations for generating fused user-viewable thermal images may include, for example, resolution and contrast enhancing fusion operations disclosed in U.S. patent application Ser. No. 13/105,765, entitled "Infrared Resolution and Contrast Enhancement with Fusion" and filed May 11, 2011, which is incorporated herein by reference in its entirety.

At block 2234, the thermal images may be viewed. For example, the user may view the user-viewable thermal images of the installation location or other scenes on display 1418 or display 1424 of measurement device 1400 to scan for hot spots 1550A, cold spots 1550B, or any other indication of faults. Because poor connections, corroded connections, incorrectly secured connections, internal damages, unbalanced loads, and other various electrical faults typically exhibit higher or lower temperature than normally operating wires and/or components, likely faulty wires and/or components may be quickly detected by viewing the user-viewable thermal images. Such suspect wires, components, and/or other external articles may be connected to the measurement device at block 2236 to check various electrical parameters (e.g., voltage, current, resistance, capacitance, and/or other parameter) associated with the wires, components, and/or other external articles. For example, the user may connect external article 1532 to appropriate ones of terminals 1404 to electrically connect external article 1532 to electrical meter circuit 1514. Test leads 1530 may be selectively used as desired.

At block 2238, an electrical meter mode is selected as the operating mode of measurement device 1400. For example, the user may input or otherwise provide a selection of an electrical meter mode on user control 1422 of measurement device 1400. In some embodiments, the user may further select one of a voltage, a current, a resistance, a capacitance, or other electrical parameter to be measured, for example, via user control 1422. Selection of an electrical meter mode may be performed prior to connecting wires, components, and/or other external articles at block 2236. At block 2240, an electrical parameter associated with the suspect wires, components, and/or other external articles may be determined using conventional techniques. At block 2242, the determined electrical parameter may be presented for viewing by the user, for example, on display 1418 by performing operations described above with respect to display 1418 of measurement device 1400. The user may view the presented electrical parameter to verify or further diagnose any fault that may be present in the suspect wires, components, and/or other external articles. If measurement of more than one electrical parameter is needed or desired, the user may select another electrical parameter, for example, on user control 1422, and blocks 2240-2242 may be repeated.

While process 2200 is described above with regard to measurement device 1400 as an example, it should be appreciated that various operations of process 2200 may be carried out by or with embodiments of measurement device 1600 or 1900 as well. For example, one skilled in the art will recognize that measurement device 1600/1900 or a user utilizing measurement device 1600/1900 may carry out various operations of blocks 2230-2242 above with appropriate modifications where applicable.

Figure 23:
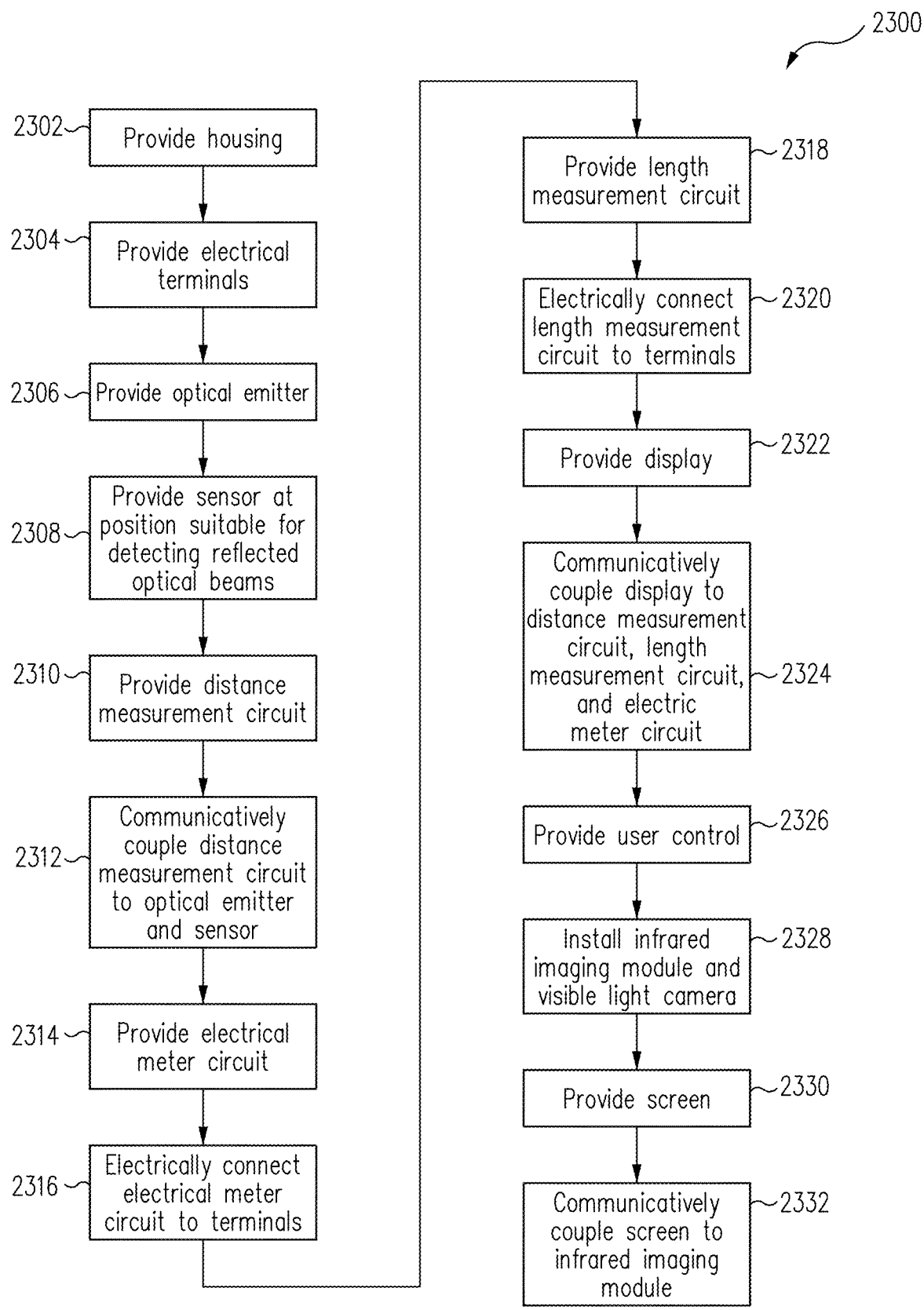
FIG. 23 illustrates a flowchart of a process to manufacture a measurement device in accordance with an embodiment of the disclosure.

Referring now to FIG. 23, a flowchart of a process 2300 to manufacture a measurement device is illustrated in accordance with an embodiment of the disclosure. For example, measurement device 1400/1600/1900 or other similar devices may be constructed by performing all or part of process 2300. In various embodiments, various operations of process 2300 may be reordered, combined, modified and/or omitted as desired for particular applications of process 2300, such as to manufacture various embodiments of measurement device 1400/1600/1900 or other similar devices. Although particular locations, placements, and orientations are described for various components of measurement device 1400/1600/1900, these may be adjusted in other embodiments as may be desired for various implementations.

At block 2302, housing 1402/1602/1902 for measurement device 1400/1600/1900 may be provided. Housing 1402/1602/1902 may be shaped and sized to be hand-held or otherwise conveniently handled by a user (e.g., an electrician) when being carried or used in field operation. For example, in one embodiment, housing 1402/1602 may be of a similar size and shape as illustrated for housing 1602A or 1602B in FIGS. 17 and 18. In another example, housing 1902 may have an elongated shape suitable for implementing measurement device 1900 in a pen-type or test pen form factor for convenience of carrying and use. In some embodiments, a handle or other protrusion (e.g., a pistol grip) may be provided on housing 1402/1602, so as to allow the user to comfortably hold housing 1402/1602. Housing 1402/1602/1902 may be made of any material suitable to protect internal components in field use. In one embodiment, housing 1402/1602/1902 may be made of a combination of durable polymer and metal. Housing 1402/1602/1902 may be manufactured by any suitable combination of molding, assembling, forging, and other applicable construction techniques.

At block 2304, electrical terminals 1404 may be provided. For example, electrical terminals 1404 may be arranged on any one or more of the exterior surfaces of housing 1402/1602/1902, at any location that allows convenient electrical connection to wires and/or external articles, as described above with respect to FIGS. 14A-15. In one embodiment, receptacles, sockets, plugs, pins, clips, screws, or other structures used to implement electrical terminals 1404 may be mounted, installed, or otherwise placed in apertures may be formed at appropriate locations on housing 1402/1602/1902. Such structures may be made of conductive material, so that electrical terminals 1404 may form an electrical connection to external wires, cables, or articles when received in the connection mechanisms. In one embodiment, such structures may insertably and/or releasably receive a test lead (e.g., test lead 1530) which may include a standard or proprietary connector. In some embodiments, probe tip 1903 may be provided on and/or partially embedded in (e.g., integrated into) proximal end 1990 of elongated housing 1902. In other embodiments, clamp 1604B or a flexible loop may be provided and electrically connected to non-contact electrical sensor 1604. Claim 1604B or the flexible loop may be provided to substantially enclose non-contact electrical sensor 1604, if desired for particular embodiments. Clamp 1604B, the flexible loop, or other structure substantially enclosing non-contact electrical sensor 1604 may be detachably provided depending on the embodiments.

At block 2306, optical emitter 1406 may be provided. In various embodiments, optical emitter 1406 may be mounted on, installed in, attached to, or otherwise fixed relative to housing 1402, such that optical emitter 1406 may transmit an optical beam without being covered or blocked by housing 1402. Optical emitter 1406 may be oriented relative to housing 1402 such that the optical beam may be aimed by a user holding and pointing housing 1402 toward a desired direction. For example, in one embodiment, at least a portion of optical emitter 1406 may be exposed and positioned on a top side of housing 1402 as illustrated in FIGS. 14A-14B, such that a user may point the top side of housing 1402 toward a desired direction to aim an optical beam transmitted from optical emitter 1406.

At block 2308, sensor 1408 may be provided at a location suitable for detecting a reflected optical beam. In various embodiments, sensor 1408 may be mounted on, installed in, attached to, or otherwise fixed on housing 1402 at a location that may be reached by the optical beam reflected from an external target (e.g., target 1542). For example, in one embodiment, at least a portion of sensor 1408 may be exposed and positioned on the same top side of housing 1402 as optical emitter 1406, as illustrated in FIG. 14B. As may be appreciated, sensor 1408 need not be perfectly aligned with optical emitter 1406, since the reflected optical beam may typically be diffused in all directions. As such, sensor 1408 may be positioned at any suitable location that may be reached by the reflected optical beam.

At block 2310, distance measurement circuit 1510 may be provided. In various embodiments, distance measurement circuit 1510 may be provided on a circuit board or other packaging, which may be substantially enclosed within, placed substantially in an interior of, or otherwise fixed relative to housing 1402, such that housing 1402 may provide to distance measurement circuit 1510 at least some protection from an external environment. Thus, for example, an appropriate combination of analog circuits, digital circuits, and/or memory devices (e.g., memory 1520) implementing distance measurement circuit 1510 may be provided on a circuit board or other suitable packaging that is substantially enclosed within, placed substantially in an interior of, or otherwise fixed relative to the housing.

At block 2312, distance measurement circuit 1510 may be communicatively coupled to optical emitter 1406 and sensor 1408. In various embodiments, suitable circuit board traces, buses, wires, cables, ribbon connectors, and/or other connectors may be provided and utilized to form signal paths suitable for transmitting analog and/or digital signals (e.g., including electric transmissions, optical transmissions, or other appropriate carriers for signals) between distance measurement circuit 1510 and optical emitter 1406, and between distance measurement circuit 1510 and sensor 1408.

At block 2314, electrical meter circuit 1514 may be provided. In various embodiments, electrical meter circuit 1514 may be provided on a circuit board or other packaging, which may be substantially enclosed within, placed substantially in an interior of, or otherwise fixed relative to housing 1402/1602/1902, such that housing 1402/1602/1902 may provide to electrical meter circuit 1514 at least some protection from an external environment. In some embodiments, electrical meter circuit 1514 may be provided on the same circuit board or other packaging as distance measurement circuit 1510, and may also share some components with distance measurement circuit 1510 depending on the embodiment. Electrical meter circuit 1514 may be implemented using an appropriate combination of analog circuits, digital circuits, and/or memory devices (e.g. memory 1520), as described above with respect to FIGS. 14A-15.

At block 2316, electrical meter circuit 1514 may be electrically connected to one or more of electrical terminals 1404 and/or non-contact electrical sensor 1604. In various embodiments, circuit board traces, cables, wires, and/or suitable other connection may be provided between electrical meter circuit 1514 and the appropriate ones of electrical terminals 1404, such that electrical paths may be formed with sufficient power ratings for desired applications of measurement device 1400/1600/1900. In some embodiments, the electrical connections may be non-switchable, such that electrical terminals 1404 may each be assigned a specific type of input (e.g., a terminal for voltage measurement, a terminal for current measurement, a terminal for ground connection, or a terminal for other type of input). In other embodiments, the electrical connections may be routed to an automatic or manual switch circuit, which may be provided as part of electrical meter circuit 1514, as part of user control 1422, or as a separate component. In such embodiments, electrical terminals 1404 may be switchable (e.g., by automatic sensing and/or receiving manual selection to adjust a switching circuit) to selectably receive different types of inputs. In yet other embodiments, some of electrical terminals 1404 may be switchable, while other may not be. In various embodiments, corresponding markings or letterings may be printed, embossed, engraved, or otherwise provided adjacent to each of electrical terminals 1404 on an exterior of housing 1402/1602/1902, so as to indicate what type of input each of electrical terminals 1404 is wired for. In some embodiments, wireless communication module 1613 may be provided where non-contact electrical sensor 1604 is detachably provided.

At block 2318, length measurement circuit 1512 may be provided. In various embodiments, length measurement circuit 1512 may be provided on a circuit board or other packaging, which may be substantially enclosed within, placed substantially in an interior of, or otherwise fixed relative to housing 1402, such that housing 1402 may provide to length measurement circuit 1512 at least some protection from an external environment. In some embodiments, length measurement circuit 1512 may be provided on the same circuit board or other packaging as distance measurement circuit 1510 and/or electrical meter circuit 1514. In some embodiments, length measurement circuit 1512 may also share some components with distance measurement circuit 1510 and/or electrical meter circuit 1514. Length measurement circuit 1512 may be implemented using an appropriate combination of analog circuits, digital circuits, and/or memory devices (e.g., memory 1520), as described above with respect to FIGS. 14A-15.

At block 2320, length measurement circuit 1512 may be electrically connected to one or more of electrical terminals 1404. In various embodiments, circuit board traces, cables, wires, and/or suitable other connection may be provided between length measurement circuit 1512 and the appropriate ones of electrical terminals 1404, such that electrical paths may be formed with sufficient power ratings for desired applications of measurement device 1400. In various embodiments, the electrical connections may be wired, routed, or otherwise formed to be non-switchable or switchable, in a similar manner as described for block 2316. In some embodiments, the electrical connections may be wired, routed, or otherwise formed to share at least one of electrical terminals 1404 with electrical meter circuit 1514.

At block 2322, display 1418 may be provided. In various embodiments, display 1418 may be mounted on, installed in, attached to, or otherwise fixed on housing 1402/1602, and may have at least a readout panel (e.g., a VFD panel, LED panel, or other multi-segment or dot-matrix panel) or an electronic display screen (e.g., a LCD screen) portion exposed on an exterior surface of housing 1402. For example, in one embodiment, display 1418 may be positioned or otherwise fixed relative to housing 1402/1602, such that the readout panel portion is exposed on the front surface of housing 1402/1602 for viewing by a user, as illustrated in FIG. 14A, 17, or 18. Display 1418 may be implemented using a readout panel or electronic screen, a display processor, and/or a memory device (e.g., memory 1520), as described above with respect to FIGS. 14A-15.

At block 2324, display 1418 may be communicatively coupled to distance measurement circuit 1510, electrical meter circuit 1514, length measurement circuit 1512, and/or other components of measurement device 1400/1600. In various embodiments, suitable circuit board traces, buses, wires, cables, ribbon connectors, and/or other connectors may be provided between display 1418 and various components of measurement device 1400/1600 to form signal paths suitable for transmitting analog and/or digital signals that may encode information indicative of the various measurements determined by the respective circuits. In some embodiments, blocks 2322 and 2324 may be omitted where display 1424 may be configured to present both measurement information and user-viewable thermal images.

At block 2326, user control 1422 may be provided. In various embodiments, user control 1422 may be disposed on, mounted on, or otherwise fixed relative to housing 1402/1602/1902, such that rotary knobs, buttons, keypads, sliders, and/or other user-activated input mechanisms may be exposed on an exterior surface of housing 1402/1602/1902 to receive interface with and receive input from a user. For example, a rotary knob or other user-activate input mechanism of user control 1422 may be exposed on the front exterior of housing 1402/1602/1902 with appropriate letterings or markings, as illustrated in FIG. 14A, 17, 18, or 20. In various embodiments, user control 1422 may be communicatively coupled (e.g., connected using appropriate circuit board traces, buses, wires, cables, ribbon connectors, and/or other connections suitable for transmitting analog and/or digital signals) to various components including distance measurement circuit 1510, electrical meter circuit 1514, and/or length measurement circuit 1512. In some embodiments, block 2326 may be omitted where user control 1422 may be implemented as a GUI present on display 1418 or display 1424.

At block 2328, infrared imaging module 1416 may be installed. In various embodiments, infrared imaging module 1416 may be mounted on, installed in, or attached to housing 1402/1602/1902 at a location that suitably provides infrared imaging module 1416 with an unobstructed view to a scene (e.g., scene 1540). In some embodiments, infrared imaging module 1416 may be oriented relative to optical emitter 1406 such that the impingement point of the optical beam from optical emitter may be placed within FOV 1541 of infrared imaging module 1416. For example, in one embodiment, at least a lens or other aperture to an FPA of infrared imaging module 1416 may be exposed and positioned on a top side of housing 1402 next to optical emitter 1406, as illustrated in FIGS. 14A-14B. In one embodiment, infrared imaging module 1416 may be received and secured in place by a socket, such as socket 104 described above with respect to FIGS. 1-2. In one embodiment, appropriate pins, tabs, plugs, or other fasteners may be provided to releasably attach infrared imaging module 1416 implemented as a plug-in unit (e.g., an add-on module). In some embodiments, non-thermal imaging module 1626 may be installed in a manner similar to infrared imaging module 1416. In some embodiments, infrared imaging module 1416 and non-thermal imaging module 1626 may be provided together in a dual sensor module and installed together.

At block 2330, a display screen (e.g., display 1424) may be provided. In various embodiments, display 1424 may be mounted on, installed in, attached to, or otherwise fixed on housing 1402/1602/1902, and may have at least an electronic display screen (e.g., a LCD screen) portion exposed on an exterior surface of housing 1402/1602/1902. For example, in one embodiment, display 1424 may be positioned or otherwise fixed relative to the housing, such that the electronic display screen portion is exposed on the front surface of housing 1402/1602/1902 for viewing by a user, as illustrated in FIG. 14A, 17, 18, or 20. In some embodiments, block 2330 may be omitted where only one display 1418 is provided.

At block 2332, the display screen (e.g., display 1424) may be communicatively coupled to processor 1519, infrared imaging module 1416, and/or other components of measurement device 1400/1600/1900. In various embodiments, suitable circuit board traces, buses, wires, cables, ribbon connectors, and/or other connectors may be provided between screen and infrared imaging module 1416 to form signal paths suitable for transmitting analog and/or digital signals that may encode raw or user-viewable thermal images captured and/or generated by infrared imaging module 1416. In embodiments where display 1418 may be configured to present user-viewable thermal images, display 1418 may also be communicatively coupled to infrared imaging module 1416.

Figure 24:
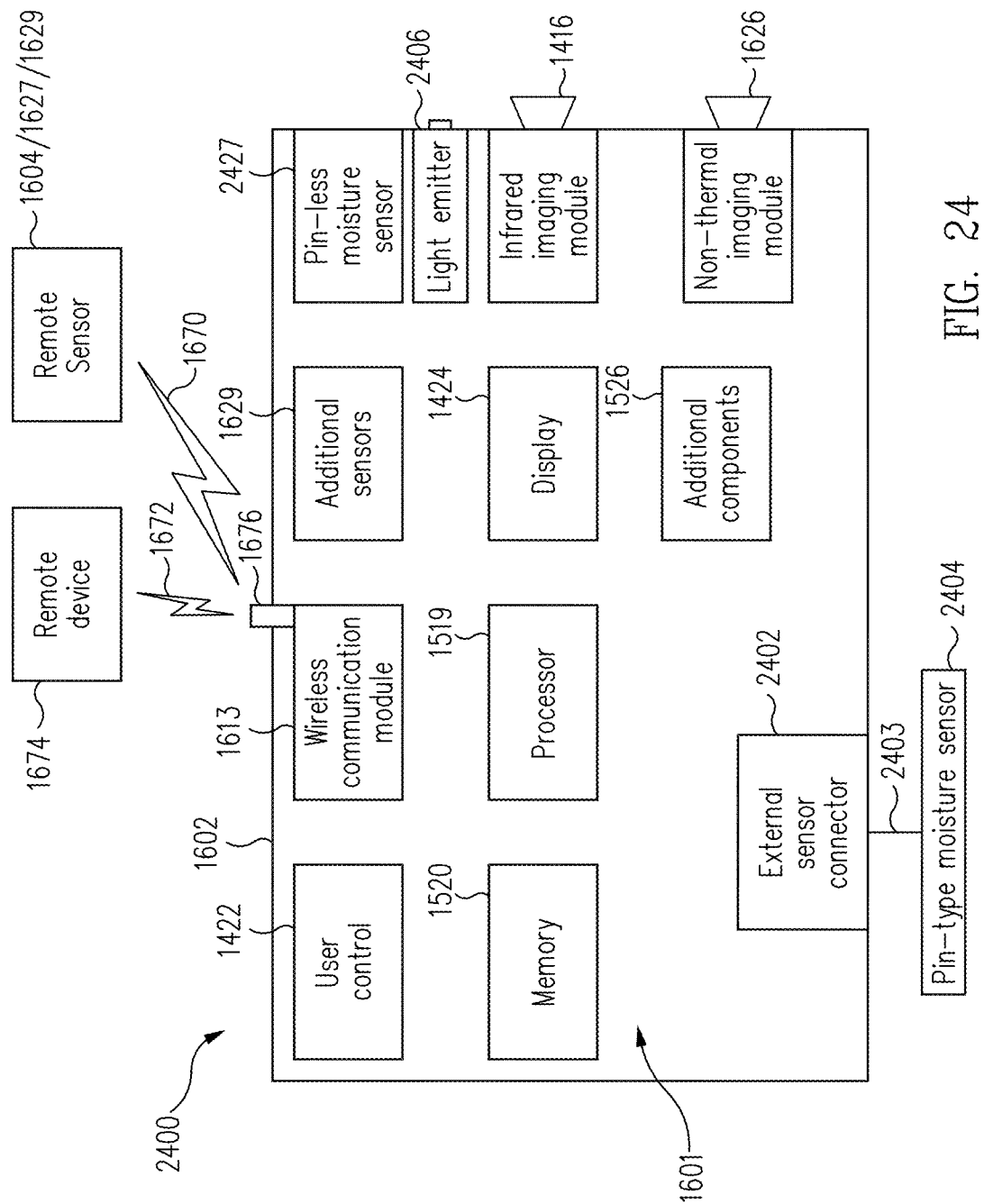
FIG. 24 illustrates a block diagram of another embodiment of a measurement device in accordance with an embodiment of the disclosure.

FIG. 24 illustrates a block diagram of another embodiment of a measurement device 2400, in accordance with an embodiment of the disclosure. As shown, measurement device 2400 may include various components described above for measurement device 1400 and measurement device 1600 and denoted by like reference numerals. Measurement device 2400 may also include an external sensor connector 2402, a cable or wire 2403, a pin-type moisture sensor 2404, a light emitter 2406, a pin-less moisture sensor 2427, and/or.

Pin-less moisture sensor 2427 may be configured to take moisture readings when measurement device 2400 is placed up to, against, or otherwise in proximity to the material, for example solid materials such as wood. In some embodiments, pin-less moisture sensor 2427 is an integral contact pad-type moisture measuring device, as described in U.S. Pat. No. 8,727,608 entitled "Moisture meter with non-contact infrared thermometer," issued May 20, 2014, which is incorporated by reference in its entirety. Pin-less moisture sensor 2427 may measure moisture based on an electric field. Pin-less moisture sensor 2427 may be located on the rear of housing 1602 so that the housing may be placed directly on a material whose moisture is to be measured. Pin-less moisture sensor 2427 may be an implementation of moisture sensor 1627.

Pin-type moisture sensor 2404 may be removably coupled to external sensor connector 2402 by cable 2403. Pin-type moisture sensor 2404 may be a pin-type moisture-sensing device as described in U.S. Pat. No. 8,727,608 entitled "Moisture meter with non-contact infrared thermometer," issued May 20, 2014. Pin-type moisture sensor 2404 may comprise a plurality of pins to make contact with or penetrate a surface of the material. Pin-type moisture sensor 2404 may be configured to measure moisture based on resistivity changes.

Pin-less moisture sensor 2427, pin-type moisture sensor 2404, or both, may be an implementation of moisture sensor 1627.

Light emitter 2406 may be a laser beam emitter, such as a laser pointer, configured to emit a laser beam to produce a visible dot on the surface of the material. Light emitter 2406 may be aligned or substantially aligned with infrared imaging module 1416 such that the visible dot is produced on the surface of the material within the FOV, such as FOV 1541, of infrared imaging module 1416. For example, the visible dot may be produced on a surface that is centrally located relative to FOV 1541. Light emitter 2406 may be, for example, an implementation of optical emitter 1406, or a separate component.

Additional sensors 1629 may include an ambient relative humidity and/or ambient temperature (RH/T) sensors, as described in U.S. Pat. No. 8,727,608 entitled "Moisture meter with non-contact infrared thermometer," issued May 20, 2014. The RH/T sensors may be located internally or in a probe that extends from and is coupled to the housing by a cable. In some embodiments, the RH/T sensors are removable and replaceable.

As described with reference to FIG. 15 and FIG. 16, display 1424 may be adapted to display user-viewable thermal images from thermal images captured by infrared imaging module 1416 and/or from images generated by combining the thermal images with non-thermal images captured by non-thermal imaging module 1626. In some embodiments, display 1424 may be further adapted to display numbers, letters, and/or symbols suitable for presenting the information generated by measurement device 2400.

For example, processor 1519 and/or display 1424 may be adapted to generate for display the measured moisture property/parameter information. The measured moisture property/parameter information may include numerical digits, with appropriate letters or symbols displayed to indicate the type of information and the applicable unit. For further example, processor 1519 and/or display 1424 may be configured to generate for display, in addition to or instead of a numerical presentation, a graphical presentation of the information generated by measurement device 2400. Such graphical presentation may include, for example, bar graphs, pie graphs, dials, line graphs, images, graphics or other suitable presentation of corresponding measurement values. In such embodiments, processor 1519 and/or display 1424 may be adapted to overlay the generated letters, numbers, symbols, graphics, and/or other representation of measurement information onto the user-viewable thermal images when the user-viewable thermal images are also displayed on display 1424.

Processor 1519 and/or display 1424 may be adapted to overlay a crosshair image indicating impingement point of beam line emitted by light emitter 1416 over a user viewable thermal image. Accordingly, the crosshair image overlaid onto the user-viewable thermal image may be aligned with the beam line.

Processor 1519 and/or display 1424 may be adapted to freeze or hold the user-viewable thermal image (e.g., a frame of user-viewable thermal images), generate moisture parameter information in response to moisture sensor 2427 or 2404 determining the moisture parameter, overlay the moisture parameter information over the frozen user-viewable thermal image, generate updated moisture parameter information in response to moisture sensor 2427 or 2404 determining the moisture parameter, and updating the overlaid moisture parameter information with the updated moisture parameter information. Processor 1519 and/or display 1424 may be adapted to. Further, processor 1519 and/or display 1424 may be adapted to capture a displayed image that includes the frozen user-viewable thermal image and the overlaid information, such as the crosshair and moisture parameter information. The captured image may be stored in a memory, such as memory 1520.

The image freezing/holding feature with moisture reading and/or crosshair overlay advantageously allows the user-viewable thermal image to be frozen and the moisture reading to be continuously updated while measurement device 2400 is moved closer to the surface of the material being measured, such as when using pin-less (pad-type) sensor 2427 for the moisture reading. Moreover, the user-viewable thermal image and moisture measurements may be conveniently captured for storing and review.

Figure 25B:
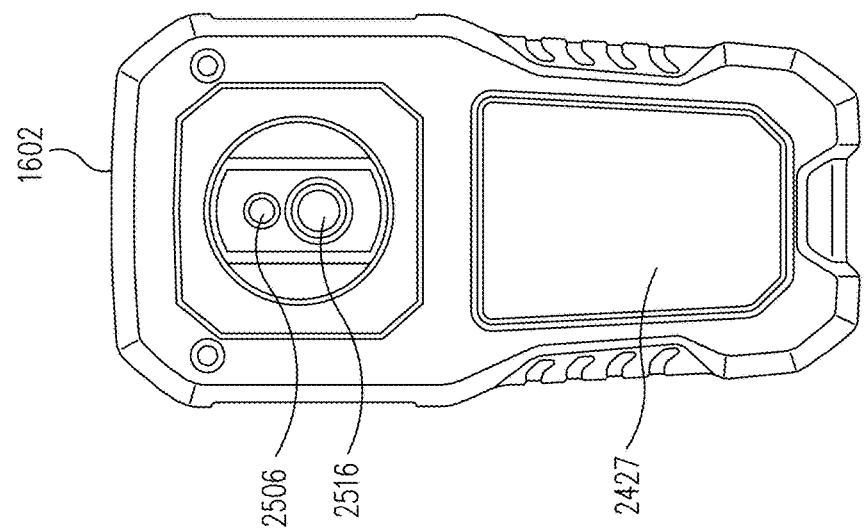
FIGS. 25A and 25B respectively illustrate an exterior front and back side view of the moisture meter of FIG. 24 implemented in accordance with an embodiment of the disclosure.
Figure 25A:
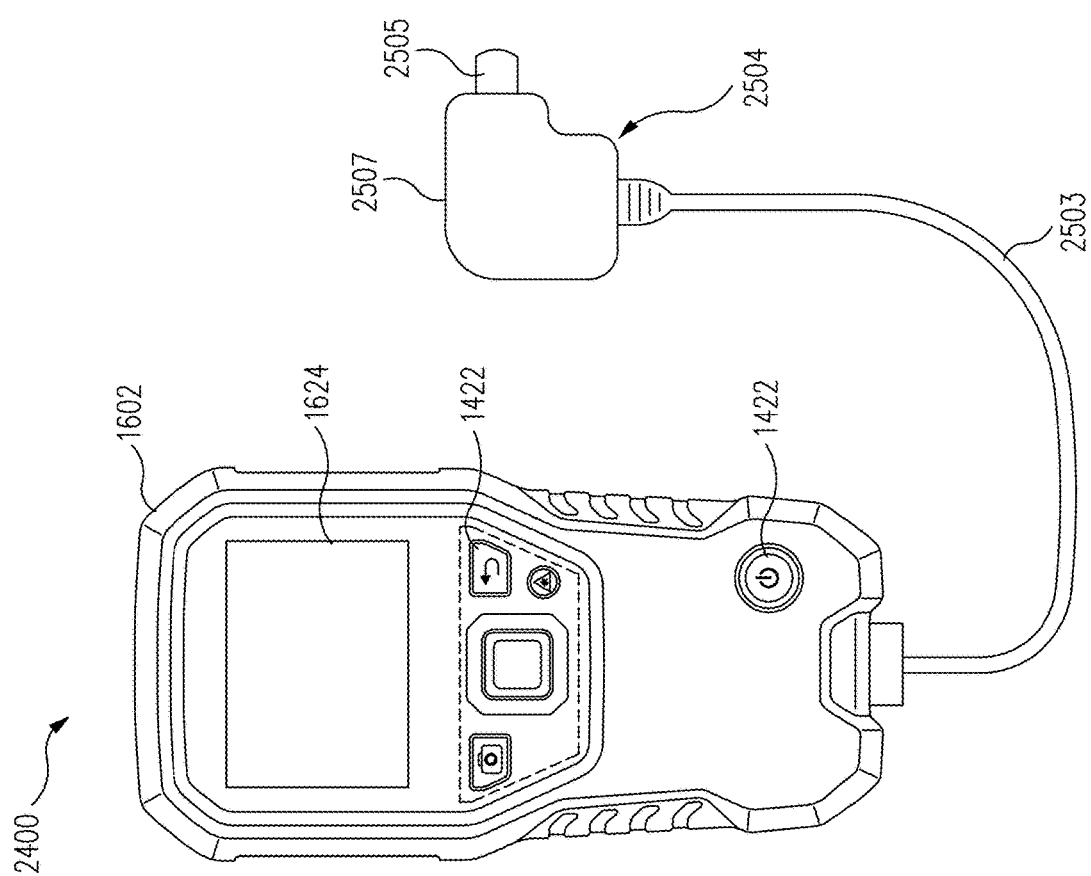

FIGS. 25A and 25B respectively illustrate an exterior front and back side view of measurement device 2400 implemented in accordance with an embodiment of the disclosure. Housing 1602 is provided that protectively contain various components of measurement device 2400, and may be of shape and size for convenient hand-held use by a user. In various embodiments, housing 1602 may be ruggedized, for example, by an overmolding process or other fabrication techniques using durable rubber and/or other composite material.

Display 1424 is disposed relative to housing 1602 for viewing by the user, for example on the front side of housing 1602 as shown in the embodiment illustrated by FIGS. 25A and 25B, or on other suitable exterior side of housing 1602 as desired for other embodiments. In the illustrated embodiment, various user control components 1422 are also disposed on the front side of housing 1602, but all or some of user control components 1422 may be disposed on one or more other exterior side of housing 1602 as suitable for convenient access during hand-held use by user according to various embodiments. User control components 1422 may include, for example, buttons for freezing thermal images, menu navigation, optical emitter and cross-hair activation, power, or other functionalities described herein for moisture meter 1602. As discussed above, slide switches, rotary switches, keypad, touchscreen, or other user input mechanism may be used in addition to or in place of buttons according to various embodiments.

FIG. 25A also shows an external pin-type moisture sensor 2504 (e.g., pin-type moisture sensor 2404) plugged into an external sensor connector (e.g., external sensor connector 2402) provided on housing 1602. In one embodiment, external pin-type moisture sensor 2504 may include one or more pins 2505 that can be driven into (e.g., penetrate) a surface (e.g., a wall or ceiling) for resistivity-base moisture sensing. External pin-type moisture sensor 2504 may include circuitry (e.g., logic device) that is configured to transmit signals indicative of moisture level sensed using pins 2505 to measurement device 2400 via a connector cord 2503 and the external sensor connector. Connector cord 2503 may be extended to a suitable length (e.g., about 2 meters) such that a thermal image of an area being measured for moisture by external pin-type moisture sensor 2504 may be captured together with the measured moisture level on a same image as further discussed herein. In some embodiments, external pin-type moisture sensor 2504 may not include connector cord 2503 but instead wirelessly transmit the signals for moisture level. The logic circuitry of external pin-type moisture sensor 2504 may be at least partially enclosed in a housing 2507, which may be ruggedized in various embodiments to withstand hammering to drive pins 2505 into a surface.

An aperture 2516 (e.g., may include a lens or other optical element) for infrared imaging module 1416 and an aperture 2506 (e.g., may include a lens or other optical element) for light emitter 2406 are disposed on the same side of housing 1602, such as for example on the back side as shown in the embodiment illustrated by FIGS. 25A and 25B. In addition, apertures 2516 and 2506 are in close proximity to each other and mechanically and/or optically aligned such that the impingement point of the light beam from light emitter 2406 corresponds to a particular area in the thermal image captured by infrared imaging module 1416 at least approximately (e.g., accounting for parallax error). Thus, for example, a cross-hair, reticle, or other visual aiming guide that at least approximately indicates the impingement point of the light beam can be overlaid by processor 1519 onto a user-viewable thermal image presented on display 1424, which may beneficially guide accurate aiming and pinpointing of a desired location for moisture measurement.

Pin-less moisture sensor 2427 (e.g., pad-type moistures sensor) may be disposed on (e.g., at least partially enclosed by) a side of housing 1602, for example on the back side as shown in the embodiment illustrated by FIGS. 25A and 25B or other sides in other embodiments, such that moisture measurements taken by placing housing 1602 near or on a surface to be measured. Although not shown for the example embodiment illustrated by FIGS. 25A and 25B, an aperture for non-thermal imaging module 1626 may be provided and substantially aligned with aperture 2516 for other embodiments that include non-thermal imaging module 1626.

Figure 26:
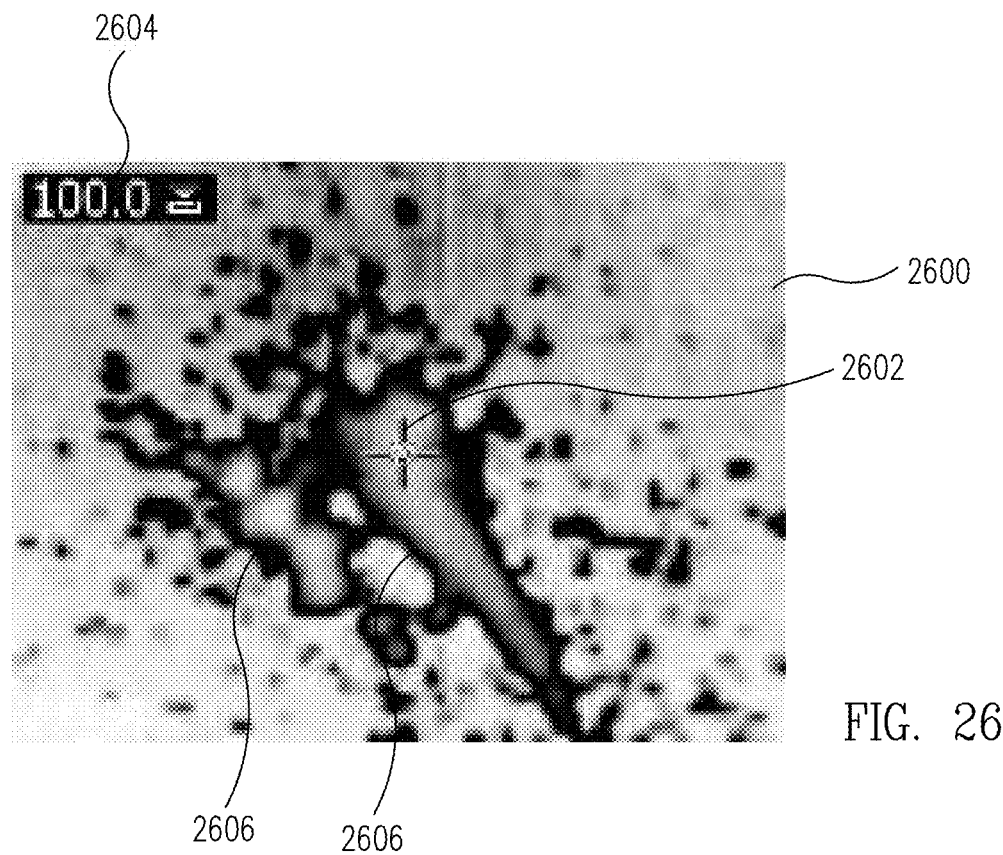
FIG. 26 is an example screenshot of a user-viewable thermal image with a visual aiming guide and a moisture reading overlaid and displayed for viewing by a user in accordance with an embodiment of the disclosure.

FIG. 26 is an example screenshot of a user-viewable thermal image 2600 with a visual aiming guide 2602 (e.g., a cross-hair or reticle) and a measurement reading 2604 (e.g., text, number, and/or graphics indicative of a measurement) overlaid and displayed (e.g. on display 1424) for viewing by a user, in accordance with an embodiment of the disclosure. In the example user-viewable thermal image 2600, a thermal anomaly (e.g., having a different temperature than other areas of a surface) may be distinguishable by a different shade or color (e.g., according to a palette or other visualization scheme for generating user-viewable images from thermal images captured by infrared imaging module 1416), as indicated for an area 2606.

Thus, by viewing user-viewable thermal image 2600, a user can, for example, "thermally target" one or more localized areas of interest with accuracy and efficiency just by quickly scanning a large site (e.g., an entire building, roof, ceiling, wall, or other sites for building inspection) with infrared imaging module 1416 of measurement device 2400. Because visual aiming guide 2602 is substantially aligned (e.g., registered) with the impingement point of the light beam from light emitter 2406, a user can further pinpoint a location to place pin-type moisture sensor 2404/2504 or pinless moisture sensor 2427 to measure moisture parameters for the exact location of interest by aiming measurement device 2400, and hence the light impingement point aligned with visual aiming guide 2602, while viewing visual aiming guide 2602 overlaid onto user-viewable thermal image 2600. Furthermore, user-viewable thermal image 2600 can be frozen (e.g., maintain the same frame of image) by processor 1519 in response to a user input via user control 1422 while measurement reading 2604 based on the determined moisture parameter is updated and overlaid onto the frozen user-viewable thermal image, thereby advantageously allowing the user to obtain and capture a user-viewable thermal image of a problem area together with a live moisture reading of a pinpoint area of interest (e.g., which may substantially coincide with the overlaid visual aiming guide 2602 depending on the user's aiming) in one screen.

Figure 27:
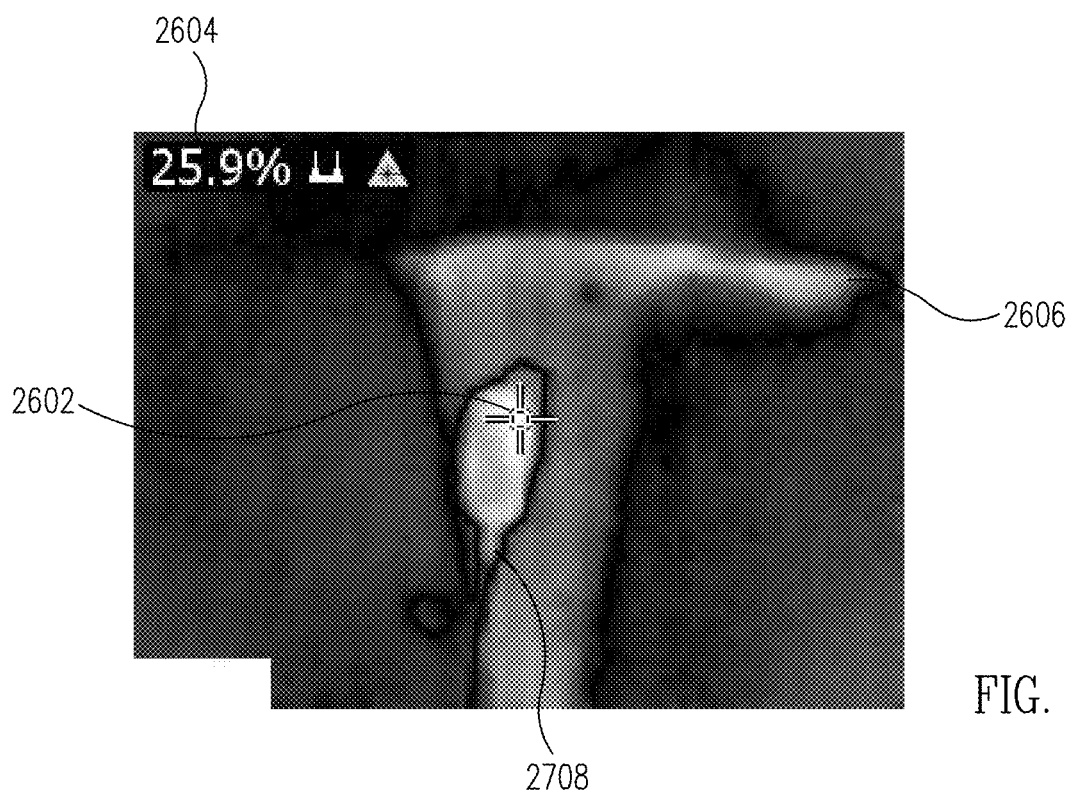
FIG. 27 is another example screenshot of a user-viewable thermal image with visual aiming guide and measurement reading overlaid and displayed for viewing by a user in accordance with an embodiment of the disclosure.

FIG. 27 is another example screenshot of a user-viewable thermal image 2700 with visual aiming guide 2602 and measurement reading 2604 overlaid and displayed for viewing by a user, in accordance with an embodiment of the disclosure. As shown in this example screenshot, external pin-type moisture sensor 2504 placed at a desired location for moisture measurement may also be visible (e.g., as indicated for an area 2708 in this example) in user-viewable thermal image 2700, together with the overlaid visual aiming guide 2602 and measurement reading 2604. Thus, when using external pin-type moisture sensor 2504, the user may advantageously obtain and capture a user-viewable thermal image of a problem area and the specific location of measurement by external pin-type moisture sensor 2504 together in one screen, along with a live moisture reading.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as non-transitory instructions, program code, and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the invention. Accordingly, the scope of the invention is defined only by the following claims.

What is claimed is:

1. An apparatus comprising:
    an infrared (IR) imaging module configured to capture thermal images of a scene;
    a moisture sensor configured to detect a moisture parameter associated with an external article;
    a housing configured to be hand-held by a user and at least partially enclosing the IR imaging module;
    a display fixed relative to the housing and configured to display user-viewable thermal images; and
    a logic device configured to:
        freeze a user-viewable thermal image on the display;
        overlay information regarding a value of the moisture parameter to indicate a first detection of the moisture parameter onto the frozen user-viewable thermal image on the display; and
        update the overlaid information to indicate a second detection of the moisture parameter.

2. The apparatus of claim 1, the logic device further configured to:
    generate the information indicating the first detection of the moisture parameter;
    generate updated information indicating the second detection of the moisture parameter; and
    update the overlaid information with the updated information.

3. The apparatus of claim 1, wherein:
    the moisture parameter comprises a presence and/or amount of moisture; and
    the moisture sensor is configured to detect the presence and/or the amount of moisture in the external article.

4. The apparatus of claim 3, wherein the moisture sensor is configured to detect the presence and/or the amount of moisture by generating an electrical field and sensing a change in the electrical field due to the presence and/or the amount of moisture in the external article.

5. The apparatus of claim 3, wherein the moisture sensor comprises a plurality of contact pins and is configured to detect the presence and/or the amount of moisture by sensing a change in electrical resistance between the contact pins contacting the external article due to the presence and/or the amount of moisture.

6. The apparatus of claim 3, wherein the moisture sensor comprises an external pin-type moisture sensor configured to transmit via wired or wireless connection a signal indicative of the presence and/or the amount of moisture.

7. The apparatus of claim 1, wherein the logic device is further configured to process the thermal images captured by the IR imaging module to generate the user-viewable thermal image.

8. The apparatus of claim 1, wherein the IR imaging module comprises an array of microbolometers.

9. The apparatus of claim 1, further comprising a memory, wherein the logic device is further configured to capture a displayed image comprising the frozen user-viewable thermal image on the display and the overlaid information and store the captured image in the memory.

10. The apparatus of claim 1, further comprising a laser pointer configured to emit a beam line, wherein the logic device is further configured to overlay a crosshair image aligned with the beam line onto the user-viewable thermal image on the display.

11. A method comprising:
    capturing a thermal image of a scene;
    generating a user-viewable thermal image based on the thermal image;
    displaying the user-viewable thermal image;
    freezing the user-viewable thermal image;
    determining a first measurement of a moisture parameter associated with an external article;
    overlaying information regarding a value of the moisture parameter to indicate the first measurement onto the frozen user-viewable thermal image;
    determining a second measurement of the moisture parameter associated with the external article; and
    updating the overlaid information to indicate the second measurement.

12. The method of claim 11, further comprising:
    generating the information indicating the first measurement; and
    generating updated information indicating the second measurement;
    wherein the updating comprises updating the overlaid information with the updated information.

13. The method of claim 11, wherein:
    the moisture parameter comprises a presence and/or amount of moisture; and
    the determining of the first measurement and the determining of the second measurement each comprises detecting the presence and/or the amount of moisture in the external article.

14. The method of claim 13, wherein the detecting of the presence and/or the amount of moisture comprises generating an electrical field and sensing a change in the electrical field due to the presence and/or the amount of moisture in the external article.

15. The method of claim 13, wherein the detecting of the presence and/or the amount of moisture comprises sensing a change in electrical resistance between contact pins contacting the external article due to the presence and/or the amount of moisture.

16. The method of claim 11, further comprising processing the thermal image to generate the user-viewable thermal image.

17. The method of claim 16, wherein the processing of the thermal image comprises indicating a thermal anomaly in the user-viewable thermal image by a distinguishable shade or color.

18. The method of claim 11, further comprising:
    determining a first measurement of a physical parameter and/or another moisture parameter associated with the external article; and
    determining a second measurement of the physical parameter and/or the other moisture parameter associated with the external article;
    wherein the overlaying of the information is further to indicate the first measurement of the physical parameter or the other moisture parameter onto the frozen user-viewable thermal image, and wherein the updating of the overlaid information is further to indicate the second measurement of the physical parameter and/or the other moisture parameter.

19. The method of claim 11, further comprising:
    capturing a displayed image comprising the frozen user-viewable thermal image on the display and the overlaid information; and
    storing the captured image in a memory.

20. The method of claim 11, further comprising:
    emitting a beam line; and
    overlaying a crosshair image aligned with the beam line onto the user-viewable thermal image on the display.

* * * * *